US011872230B2

United States Patent
Wang et al.

(10) Patent No.: US 11,872,230 B2
(45) Date of Patent: *Jan. 16, 2024

(54) METHOD OF TREATING A METHIONINE-DEPENDENT CANCER

(71) Applicant: Agency for Science, Technology and Research, Singapore (SG)

(72) Inventors: Zhenxun Wang, Singapore (SG); Wai Leong Tam, Singapore (SG); Lian Yee Yip, Singapore (SG); Ying Swan Ho, Singapore (SG); Zhengwei Wu, Singapore (SG); Bing Lim, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/745,292

(22) Filed: May 16, 2022

(65) Prior Publication Data

US 2022/0280520 A1 Sep. 8, 2022

Related U.S. Application Data

(63) Continuation of application No. 16/039,916, filed on Jul. 19, 2018, now Pat. No. 11,376,256.

(51) Int. Cl.
*C12Q 1/6886* (2018.01)
*A61K 31/52* (2006.01)
*A61P 35/04* (2006.01)
*A61K 31/7105* (2006.01)
*A61K 31/67* (2006.01)

(52) U.S. Cl.
CPC .............. *A61K 31/52* (2013.01); *A61K 31/67* (2013.01); *A61K 31/7105* (2013.01); *A61P 35/04* (2018.01); *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 9,132,102 B2 | 9/2015 | Watt et al. | |
| 11,376,256 B2 | 7/2022 | Wang et al. | |
| 2014/0249161 A1* | 9/2014 | Watt ..................... | A61K 31/03 514/645 |
| 2016/0374971 A1 | 12/2016 | Rabinowitz et al. | |
| 2022/0280520 A1 | 9/2022 | Wang et al. | |

FOREIGN PATENT DOCUMENTS

WO WO-2017/096165 A1 6/2017

OTHER PUBLICATIONS

Jolivet (The New England Journal of Medicine Nov. 3, 1983 pp. 1094-1104).*
Chan (G&P magazine 2006 vol. 6 No. 3 pp. 20-26).*
Zhang (Acta Histochemica 115 (2013) vol. 48-55).*
Cavuoto (Cancer Treatment Reviews 38 2012 726-736).*
Dana (Journal of Stem Cell Research and Therapeutics vol. 1 Issue 6 2016).*
Basu (Journal of Biological Chemistry vol. 286 No. 6 Feb. 2011).*
Banks et al., Inhibition of cobalamin-dependent methionine synthase by substituted benzo-fused heterocycles. FEBS J. Jan. 2007;274(1):287-99.
Basu et al., Growth and metastases of human lung cancer are inhibited in mouse xenografts by a transition state analogue of 5'-methylthioadenosine phosphorylase. J Biol Chem. Feb. 11, 2011;286(6):4902-11.
Bataille et al., Strong expression of methylthioadenosine phosphorylase (MTAP) in human colon carcinoma cells is regulated by TCF1/[beta]-catenin. Lab Invest. Jan. 2005;85(1):124-36.
Borrego et al., Metabolic changes associated with methionine stress sensitivity in MDA-MB-468 breast cancer cells. Cancer Metab. May 2, 2016;4:9. 17 pages.
Breillout et al., Methionine dependency of malignant tumors: a possible approach for therapy. J Natl Cancer Inst. Oct. 17, 1990;82(20):1628-32.
Cavuoto et al., A review of methionine dependency and the role of methionine restriction in cancer growth control and life-span extension. Cancer Treat Rev. Oct. 2012;38(6):726-36.
Cellarier et al., Methionine dependency and cancer treatment. Cancer Treat Rev. Dec. 2003;29(6):489-99.
Chan et al., Integrating Transcriptomics and Proteomics. G & P Magazine. Apr. 2006;6(3):20-26.
Dana et al., CD166 as a Stem Cell Marker? A Potential Target for Therapy Colorectal Cancer? Journal of Stem Cell Research & Therapeutics. 2016;1(6):00041, 4 pages.
Ducker et al., Human SHMT inhibitors reveal defective glycine import as a targetable metabolic vulnerability of diffuse large B-cell lymphoma. Proc Natl Acad Sci U S A. Oct. 24, 2017;114(43):11404-11409.
Hao et al., Characterization of human S-adenosyl-homocysteine hydrolase in vitro and identification of its potential inhibitors. J Enzyme Inhib Med Chem. Dec. 2017;32(1):1209-1215.
Hu et al., Mechanisms of drug resistance in colon cancer and its therapeutic strategies. World J Gastroenterol. Aug. 14, 2016;22(30):6876-89.
Jolivet et al., The pharmacology and clinical use of methotrexate. N Engl J Med. Nov. 3, 1983;309(18):1094-104.
Khoury et al., Acquisition of anticancer drug resistance is partially associated with cancer stemness in human colon cancer cells. Int J Oncol. Dec. 2016;49(6):2558-2568.
Mosley et al., Carbocyclic pyrimidine nucleosides as inhibitors of S-adenosylhomocysteine hydrolase. Bioorg Med Chem. Dec. 1, 2006;14(23):7967-71.

(Continued)

*Primary Examiner* — Amanda Haney
(74) *Attorney, Agent, or Firm* — McCarter & English, LLP; Maria Laccotripe Zacharakis; Miao Yu

(57) ABSTRACT

The present invention relates generally to a therapeutic protocol for treating a subject having cancer. Taught herein is a method of treating cancer or reducing the risk of recurrence of cancer in a subject following an anti-cancer therapy.

4 Claims, 64 Drawing Sheets

Specification includes a Sequence Listing.

(56) References Cited

OTHER PUBLICATIONS

Poirson-Bichat et al., Methionine depletion enhances the antitumoral efficacy of cytotoxic agents in drug-resistant human tumor xenografts. Clin Cancer Res. Feb. 2000;6(2):643-53.

Stankova et al., Antisense inhibition of methylenetetrahydrofolate reductase reduces cancer cell survival in vitro and tumor growth in vivo. Clin Cancer Res. Mar. 1, 2005;11(5):2047-52.

Wiiger et al., A novel human recombinant single-chain antibody targeting CD166/ALCAM inhibits cancer cell invasion in vitro and in vivo tumour growth. Cancer Immunol Immunother. Nov. 2010;59(11):1665-74.

Yamada et al., Regulation of human methylenetetrahydrofolate reductase by phosphorylation. Proc Natl Acad Sci U S A. Jul. 26, 2005;102(30):10454-9.

Zhang et al., Fluorinated N,N-dialkylaminostilbenes repress colon cancer by targeting methionine S-adenosyltransferase 2A. ACS Chem Biol. Apr. 19, 2013;8(4):796-803.

Zhang et al., Overexpression of methionine adenosyltransferase II alpha (MAT2A) in gastric cancer and induction of cell cycle arrest and apoptosis in SGC-7901 cells by shRNA-mediated silencing of MAT2A gene. Acta Histochem. Jan. 2013;115(1):48-55.

\* cited by examiner

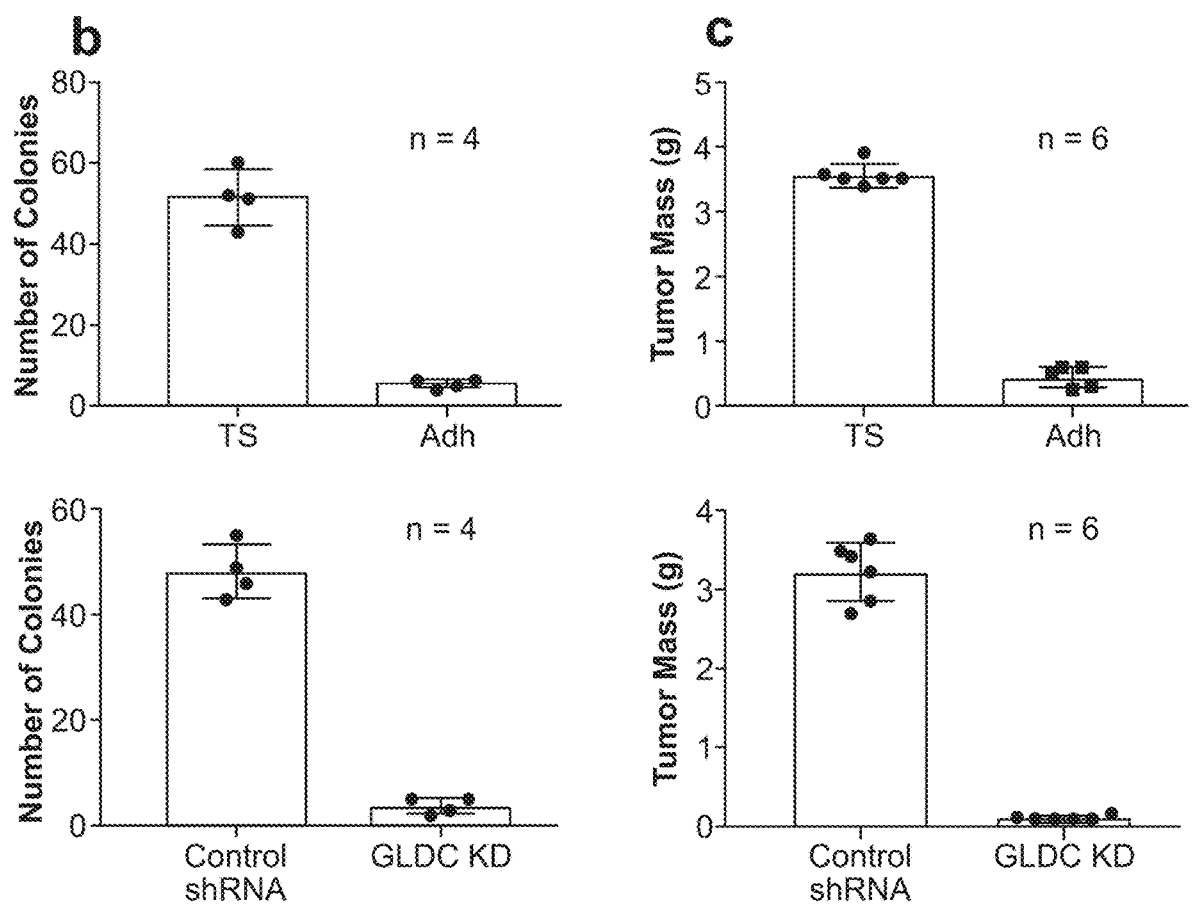
Figure 1(b)–(c)

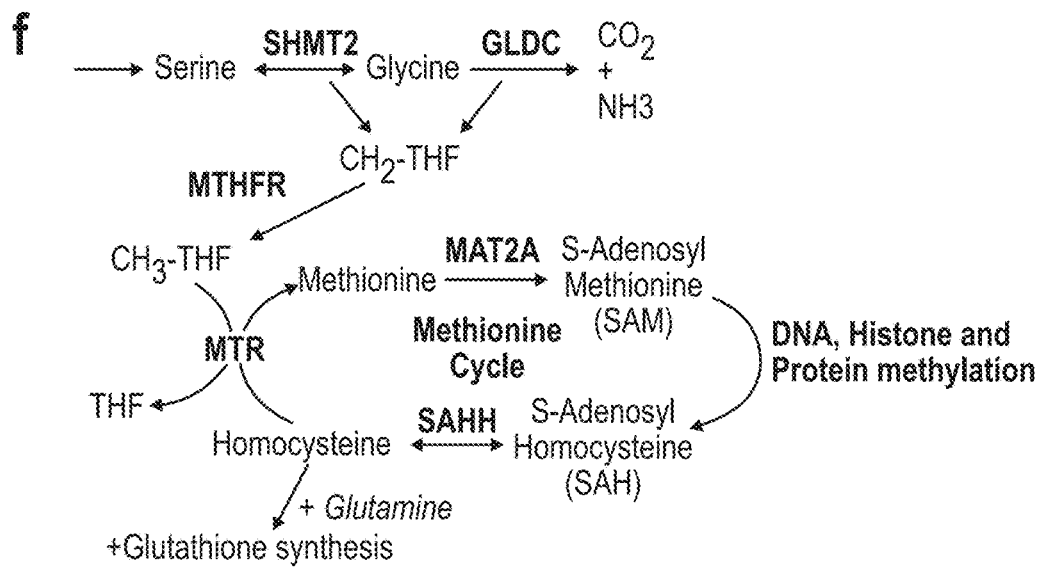
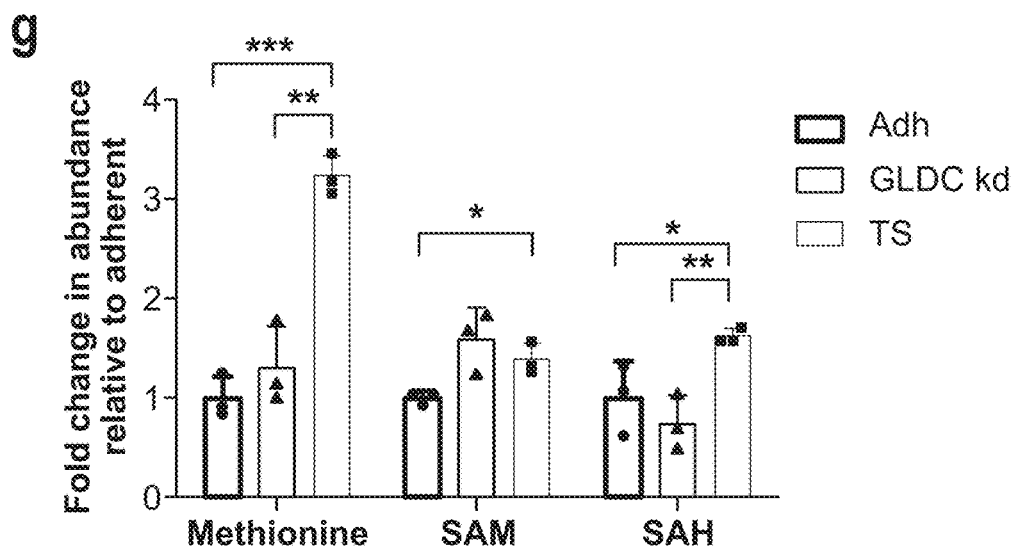
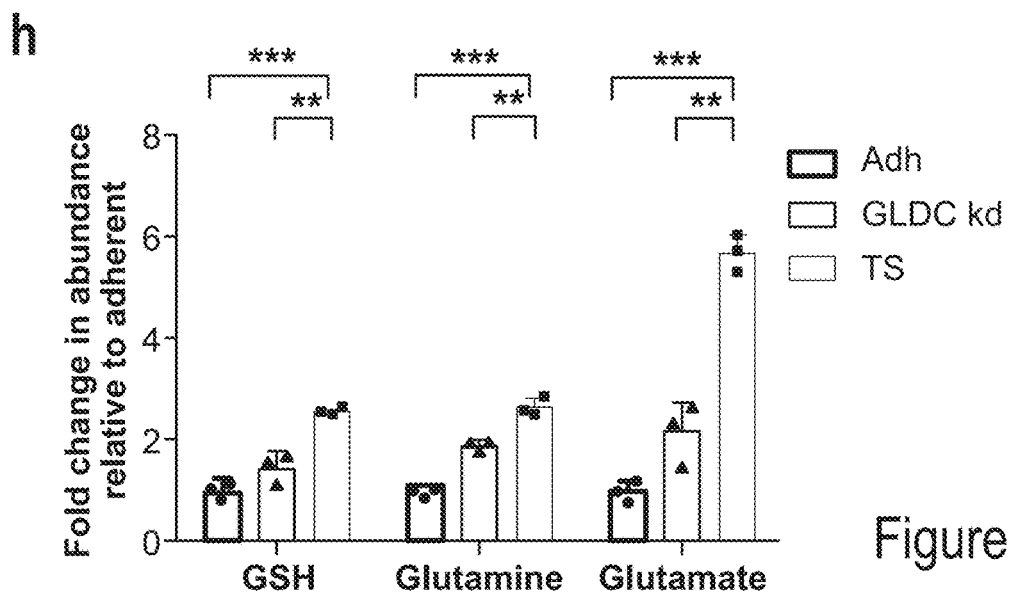
Figure 1(f)–(h)

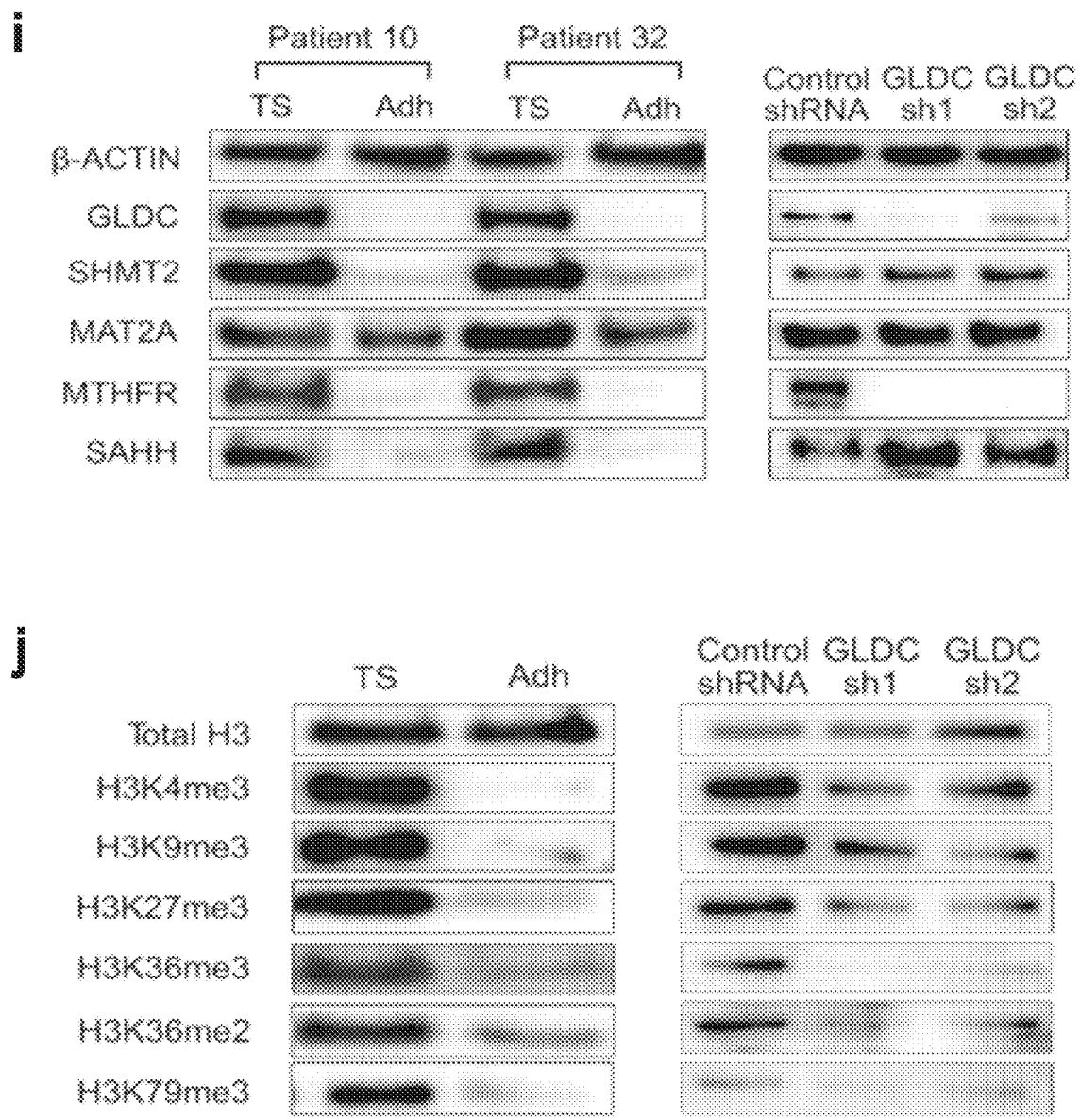
Figure 1(i)–(j)

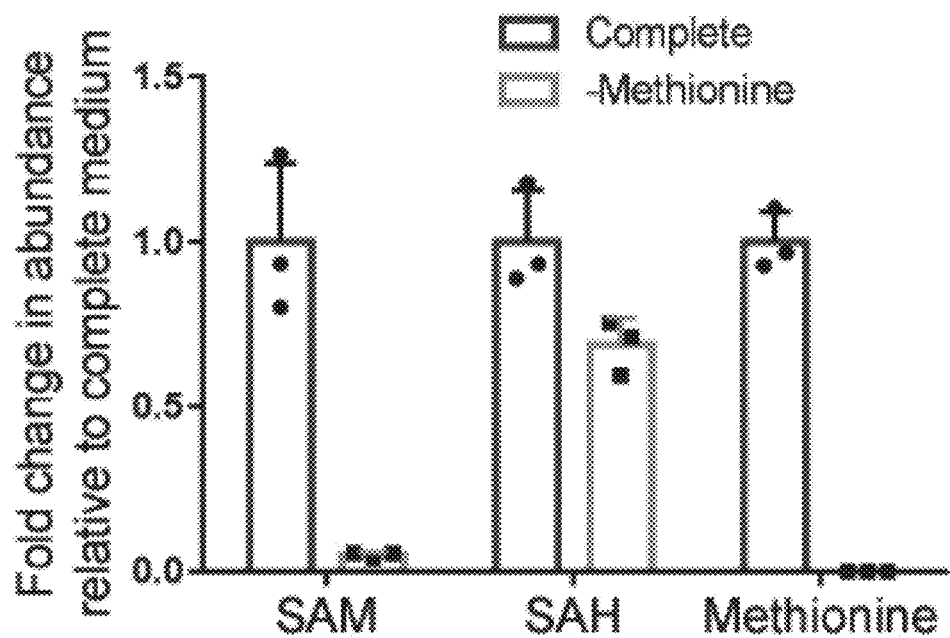
Figure 2(a)–(b)

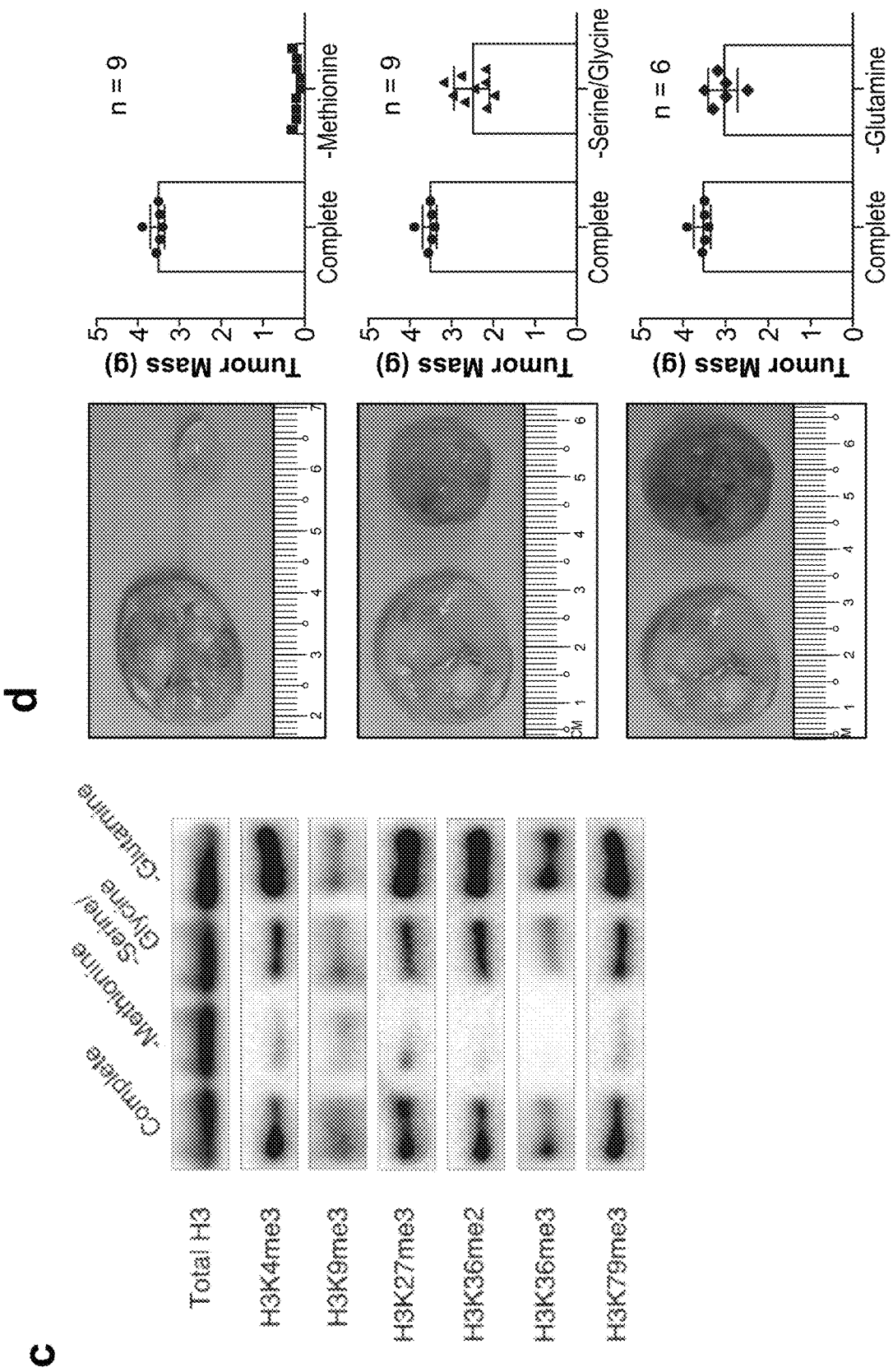
Figure 2(c)-(d)

(e)

| Cells | No. of cells per injection | No. of tumors/ No. of injections | LTICs Frequency (95% CI) | P-value |
|---|---|---|---|---|
| Tumorspheres | 10,000 | 10/12 | 1/5,581 | |
| | 100,000 | 6/6 | (1/2,755 – | |
| | 500,000 | 10/10 | 1/11,308) | |
| -Methionine | 10,000 | 0/6 | 1/244,309 | |
| | 100,000 | 5/6 | (1/130,328 – | 3.03E-13 |
| | 500,000 | 9/12 | 1/459,274) | |

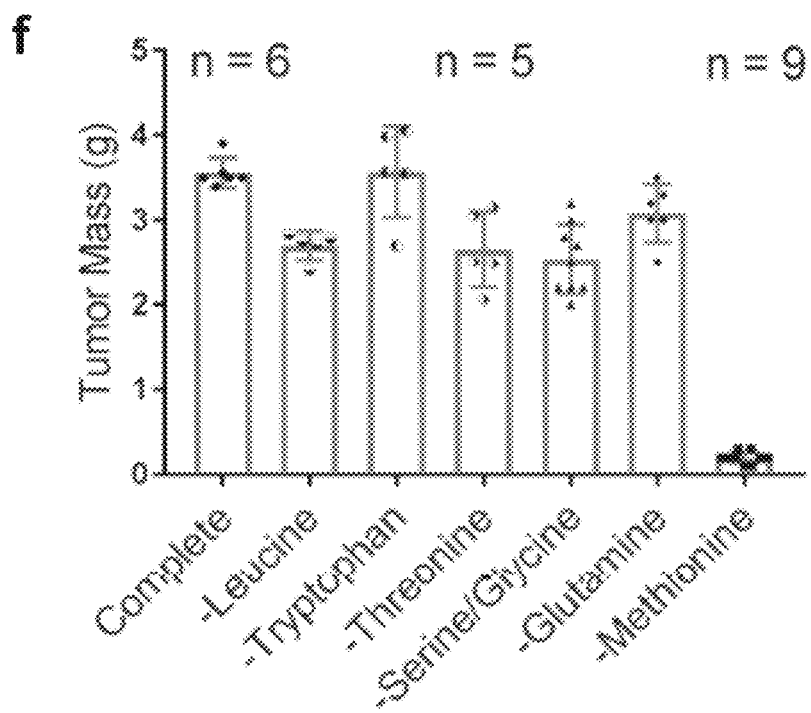
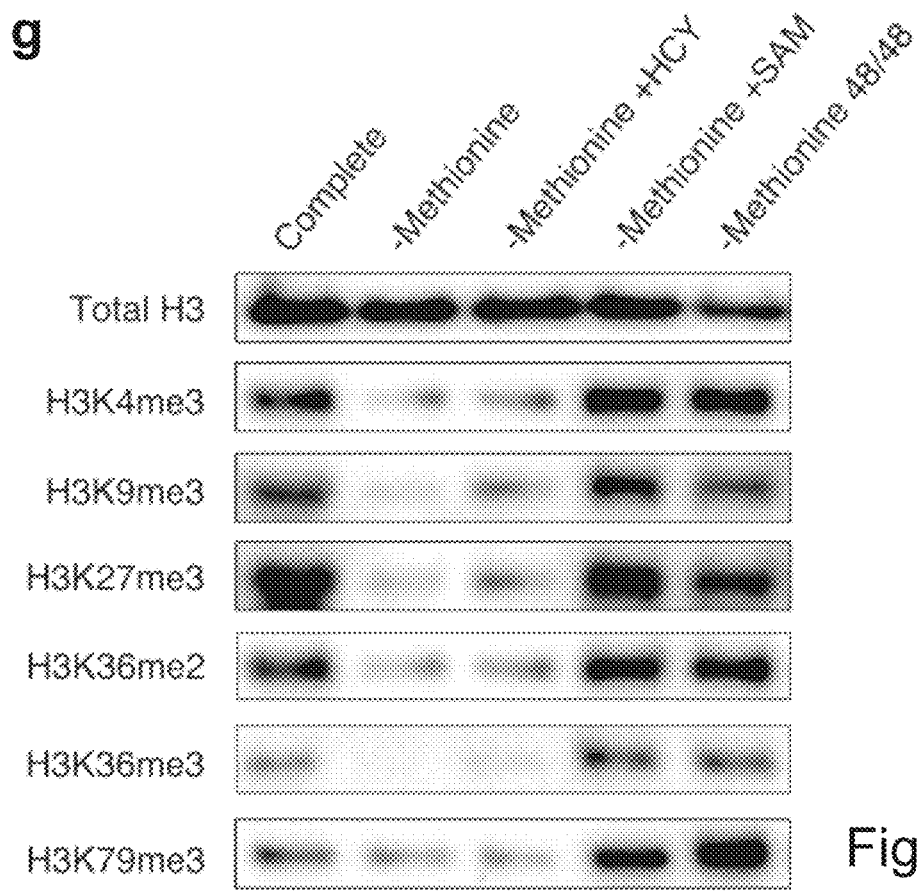
Figure 2(f)–(g)

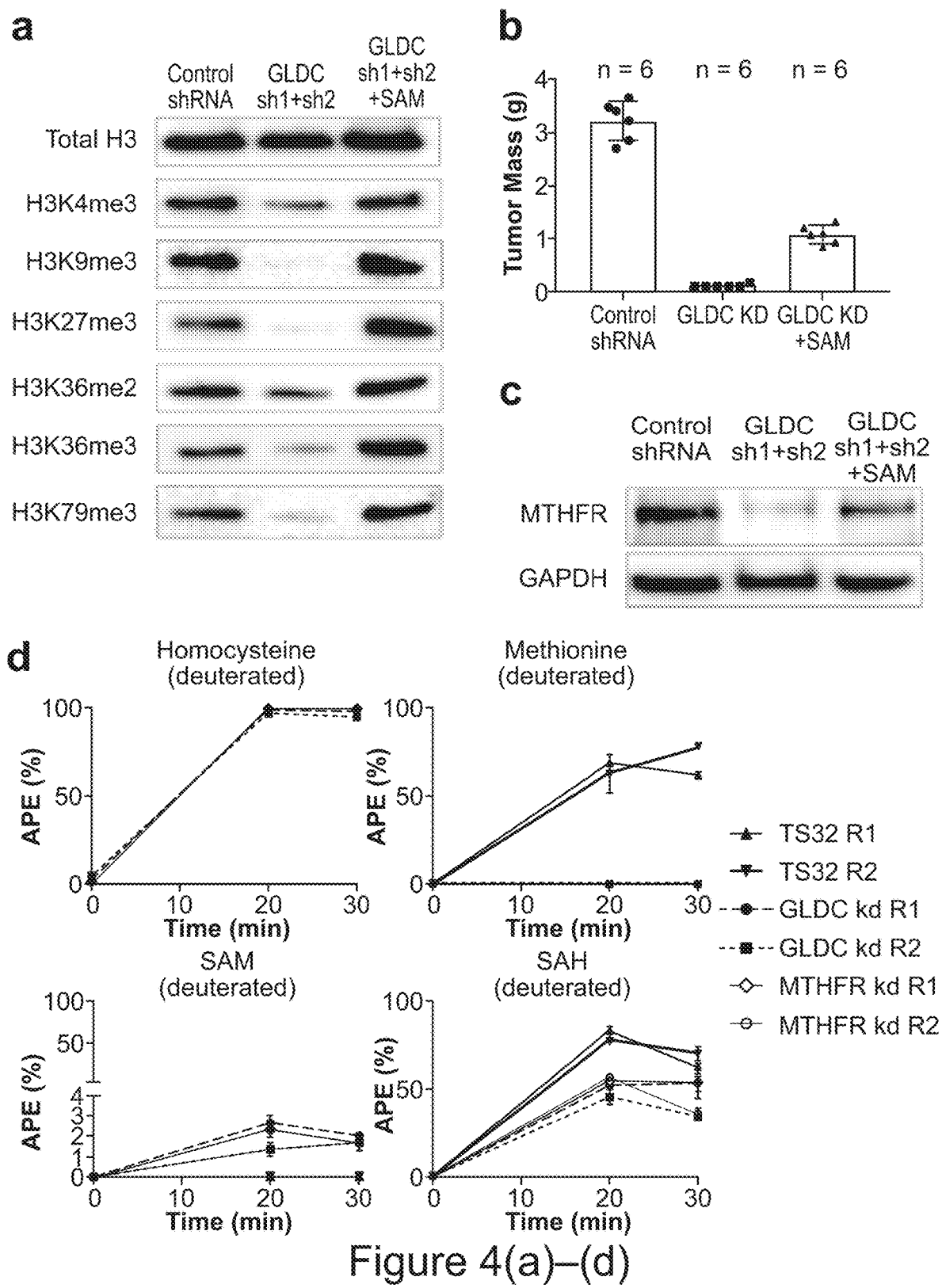
Figure 4(a)–(d)

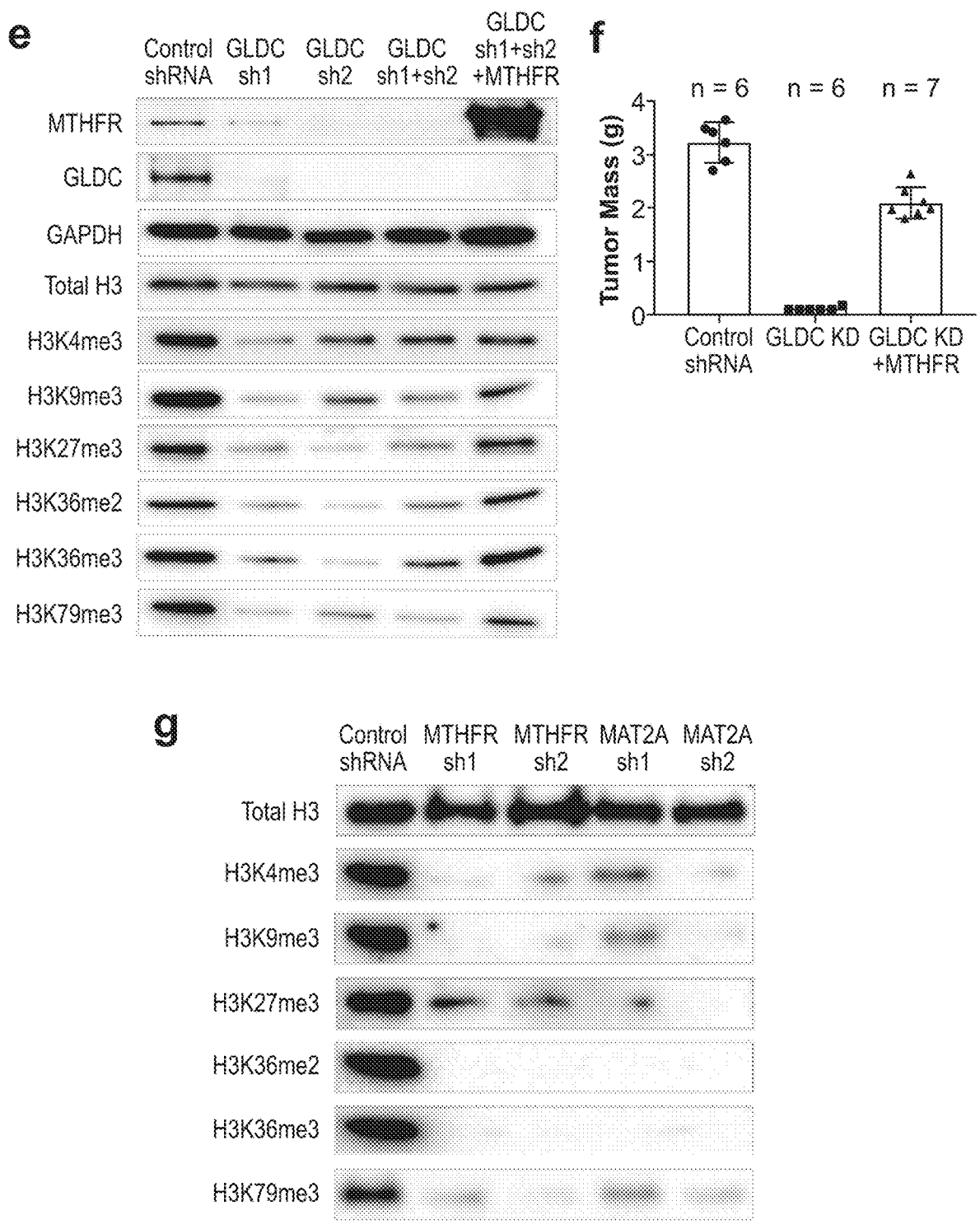
Figure 4(e)–(g)

i
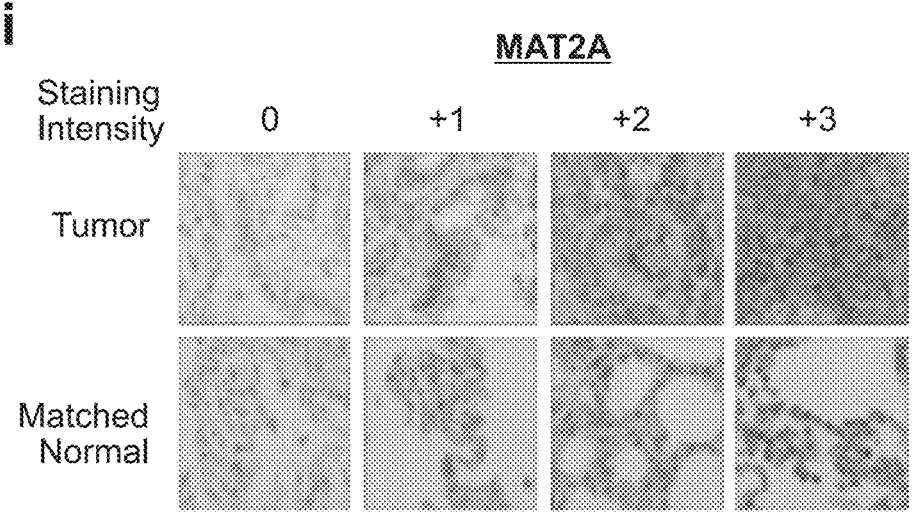
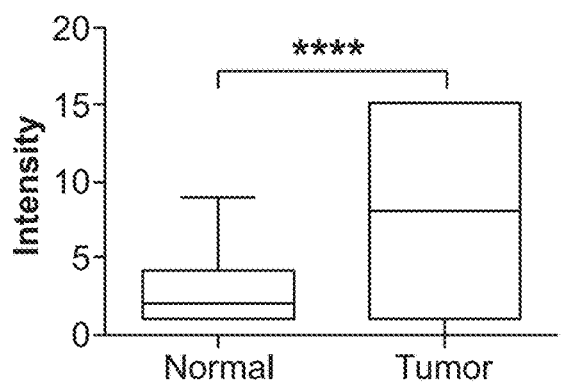
j
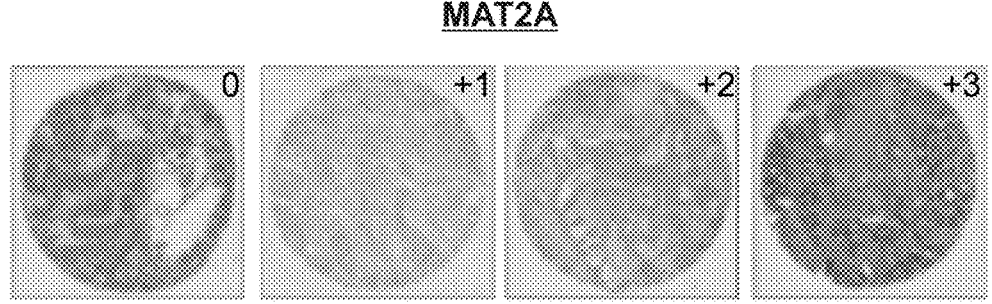
Figure 4(i)–(j)

k

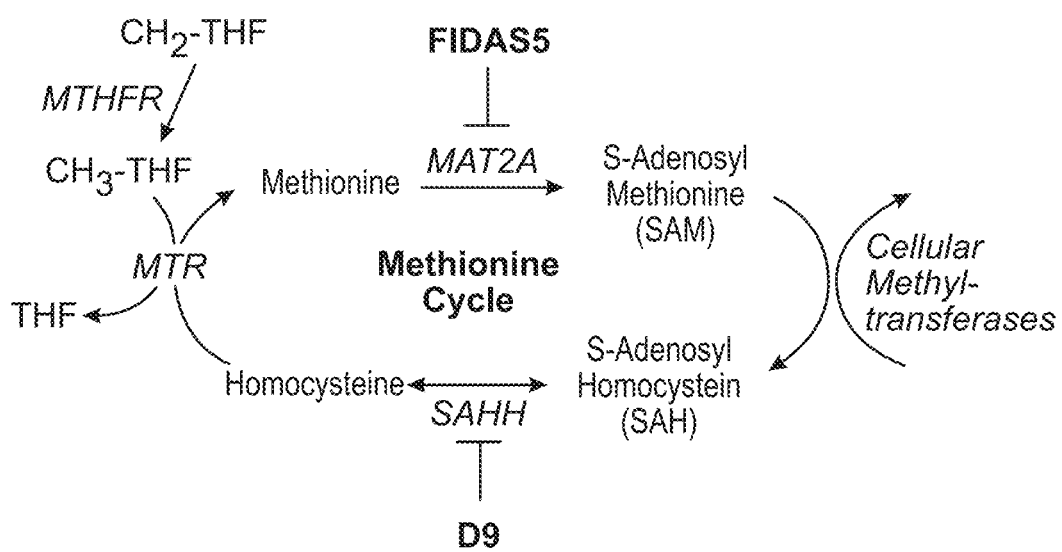
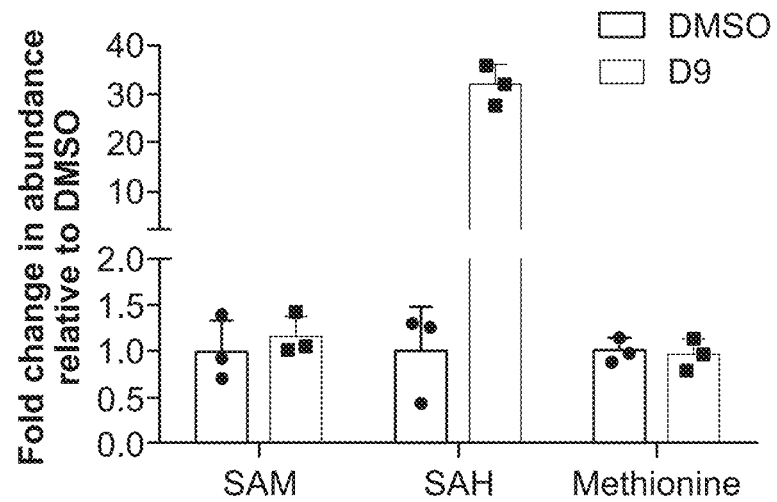
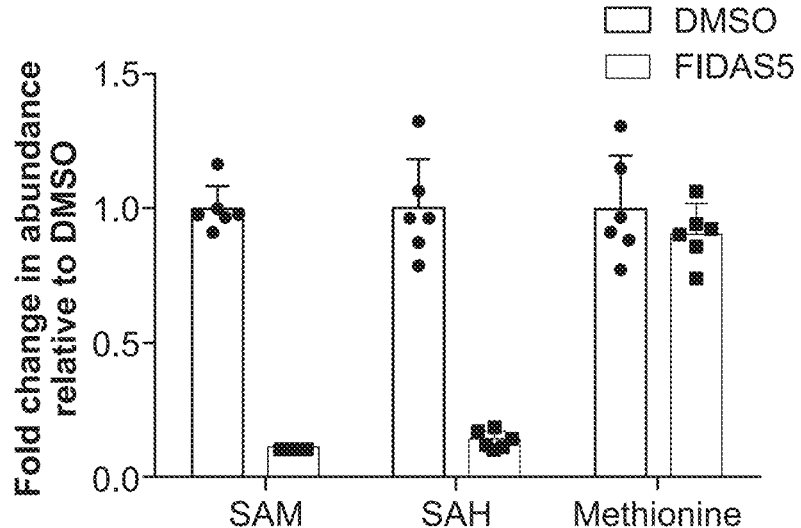
Figure 5(a)–(c)

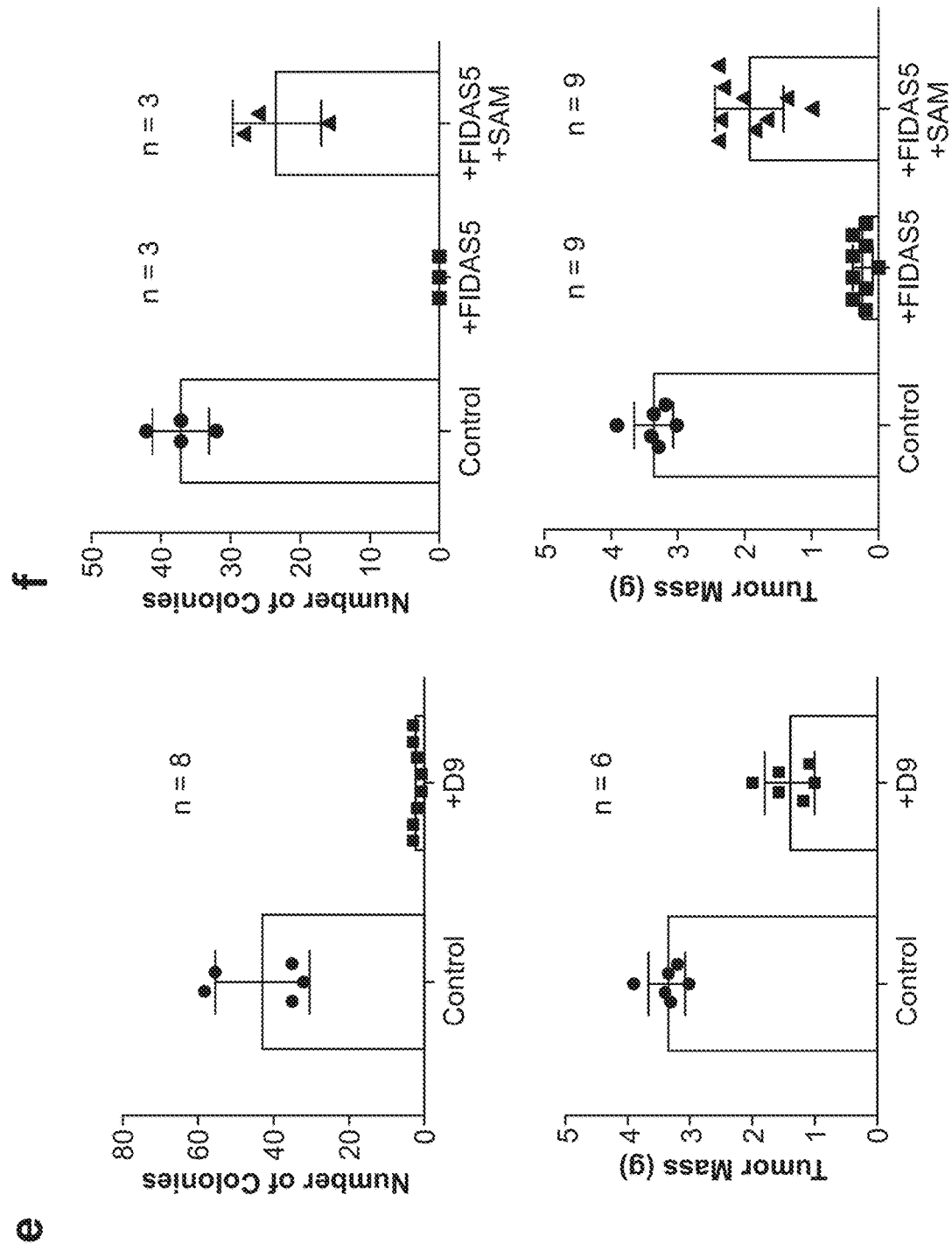
Figure 5(e)–(f)

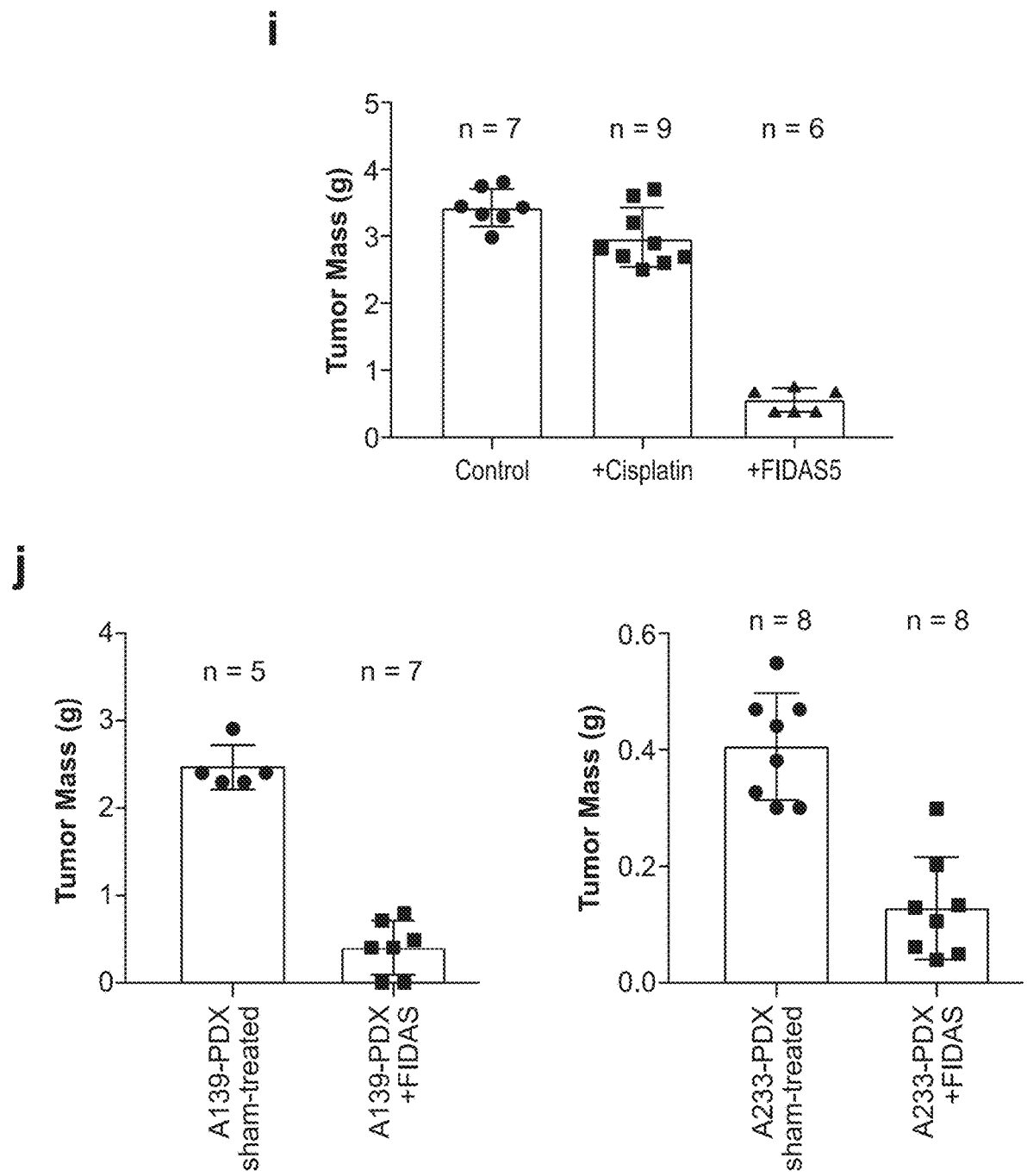
Figure 5(i)–(j)

| CELL LINE | MAT2A LEVEL | MTAP STATUS | TISSUE | FIDAS5 (IC50 μM) |
|---|---|---|---|---|
| NCI-H82 | High | Wild-type | Lung | 4.31 |
| TS32 | High | Wild-type | Lung | 5.09 |
| PA-1 | Low | Wild-type | Ovary | 8.12 |
| MM.1S | High | Wild-type | Heme | 11.59 |
| HL-60 | High | Wild-type | Heme | 12.79 |
| KMS-11 | High | Wild-type | Heme | 13.96 |
| IM95m | Low | Wild-type | Gastric | 14.56 |
| NUGC-3 | Low | Wild-type | Gastric | 20.5 |
| SNU-387 | Low | Null | Liver | 20.97 |
| Jurkat, Clone E6-1 | Low | Null | Heme | 23.63 |
| A549 | High | Null | Lung | 27.69 |
| MG-63 | Low | Null | Bone | 39.31 |
| MKN-7 | Low | Null | Gastric | 47.67 |
| MKN-45 | Low | Null | Gastric | 50.76 |
| MIA PaCa-2 | Low | Null | Pancreas | 55.35 |
| CaCo-2 | Low | Null | Colon | 62.46 |
| MKN-74 | Low | Null | Gastric | 86.13 |

Figure 6(b)

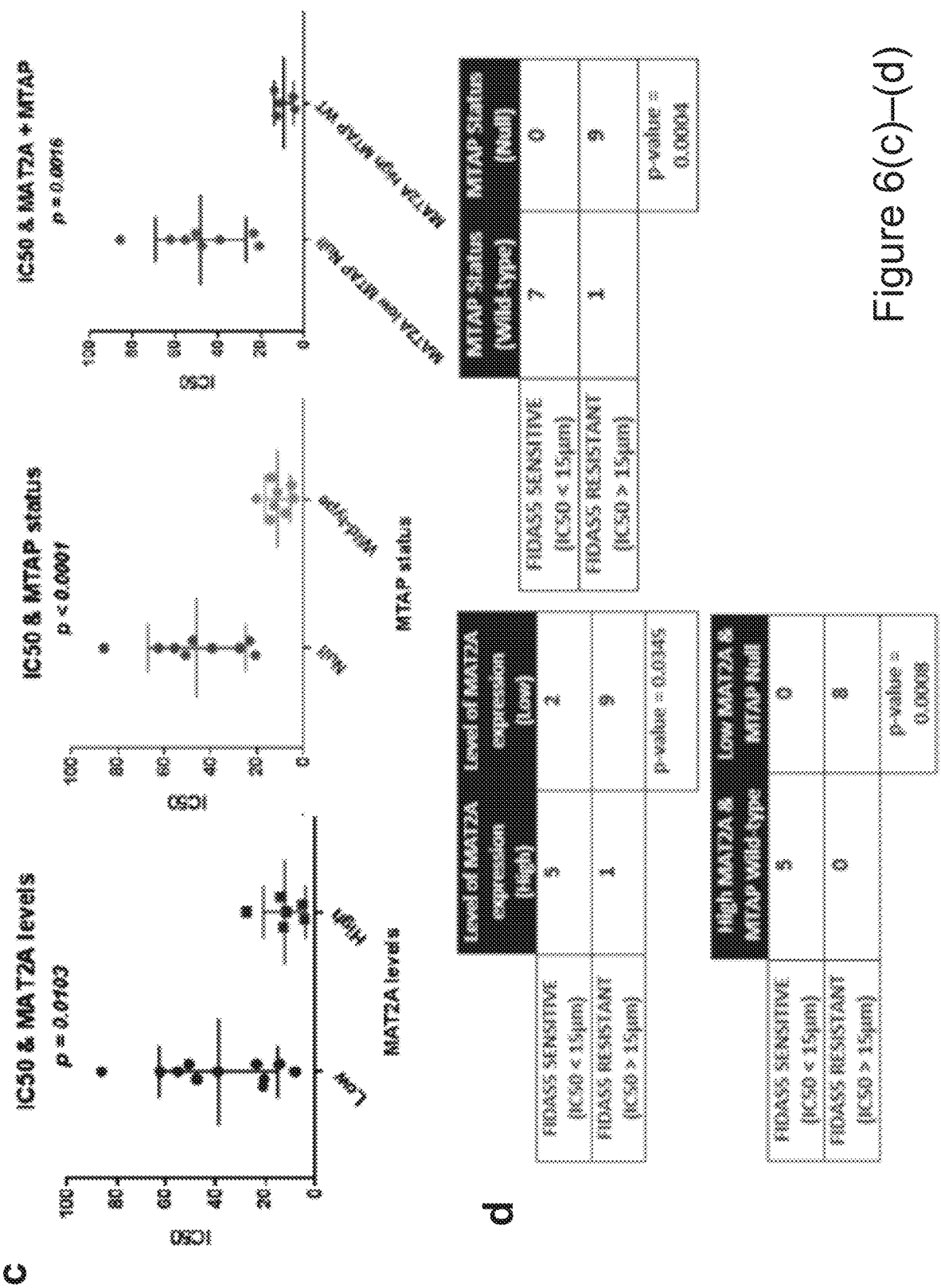
Figure 6(c)-(d)

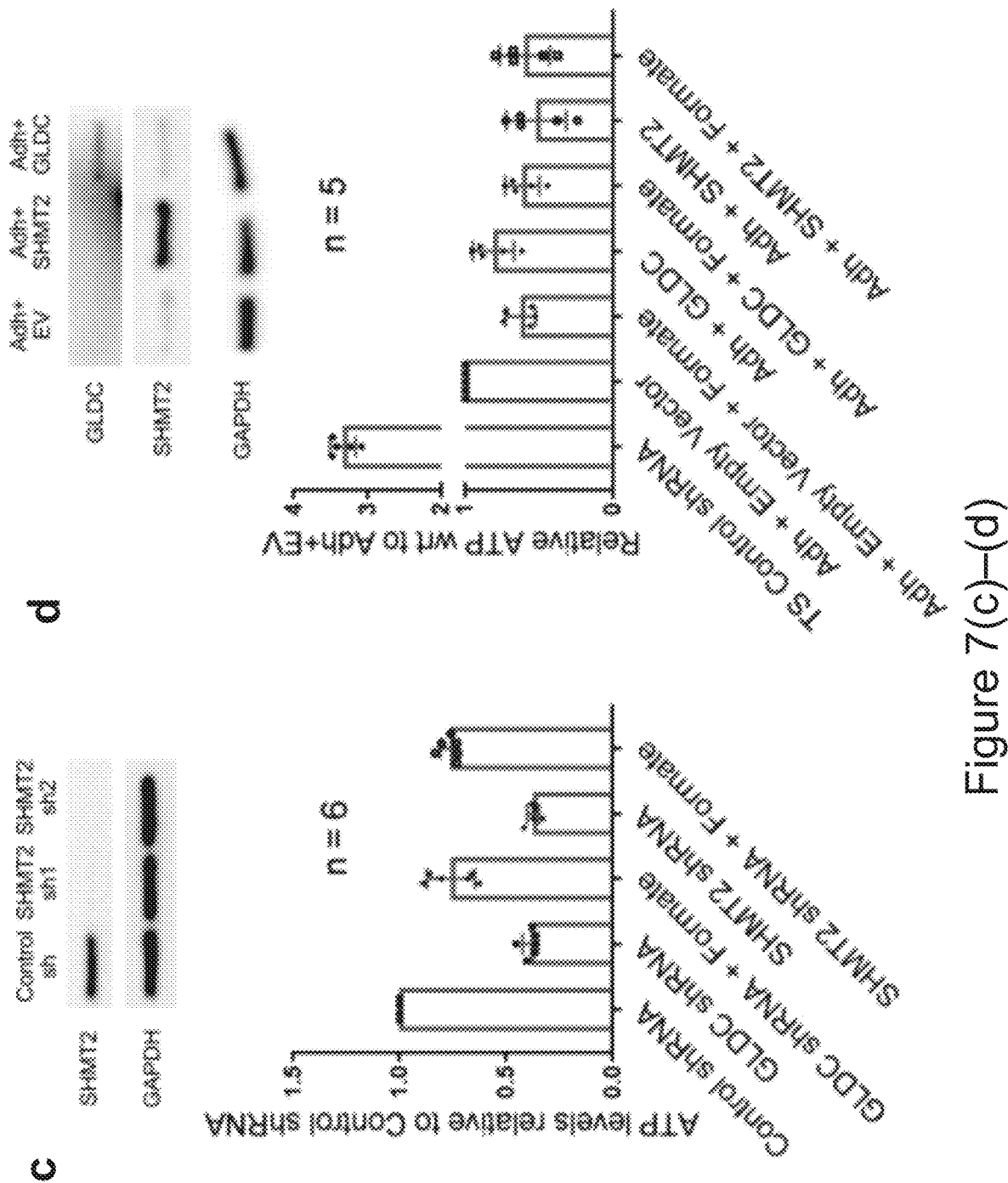
Figure 7(c)–(d)

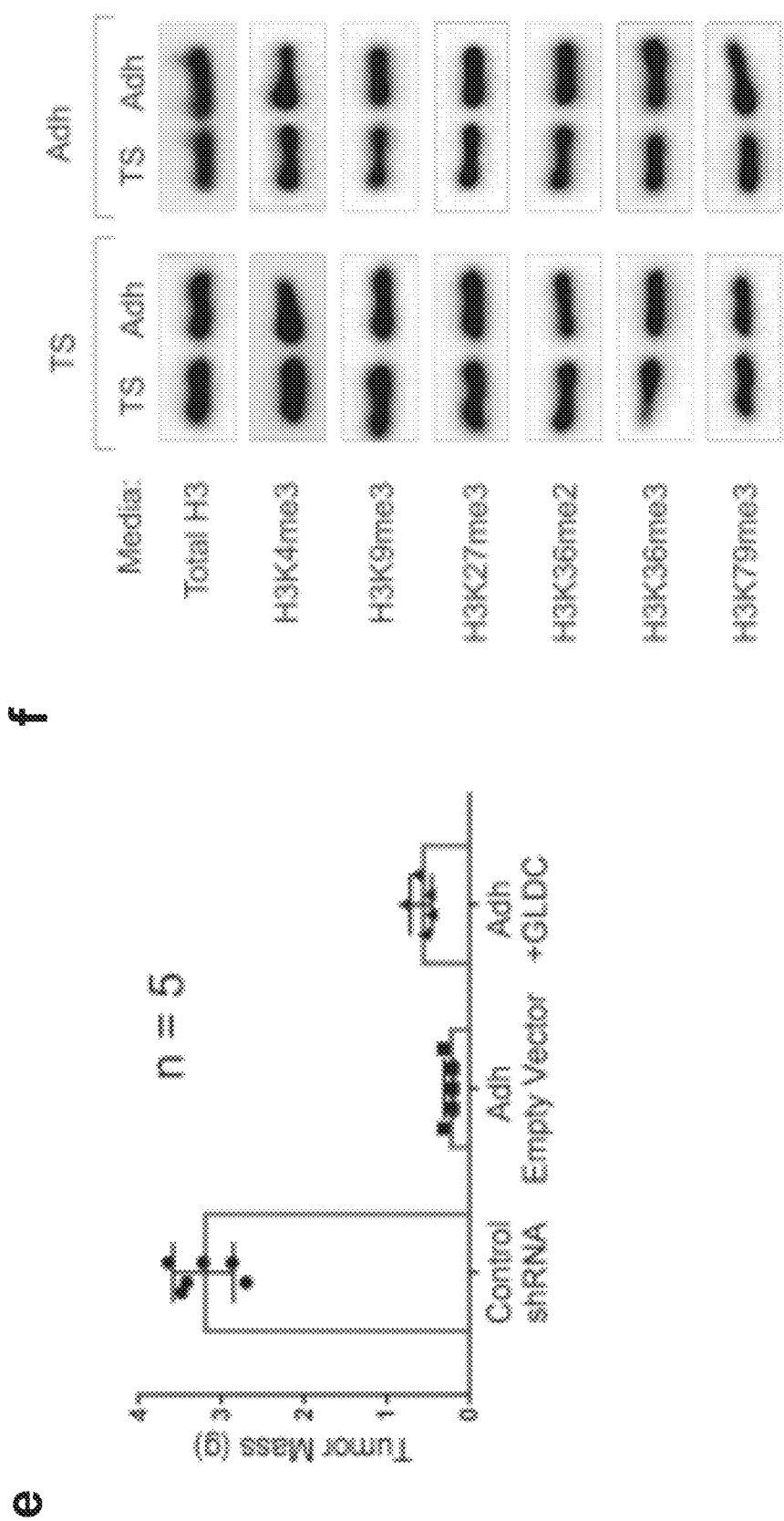
Figure 7(e)–(f)

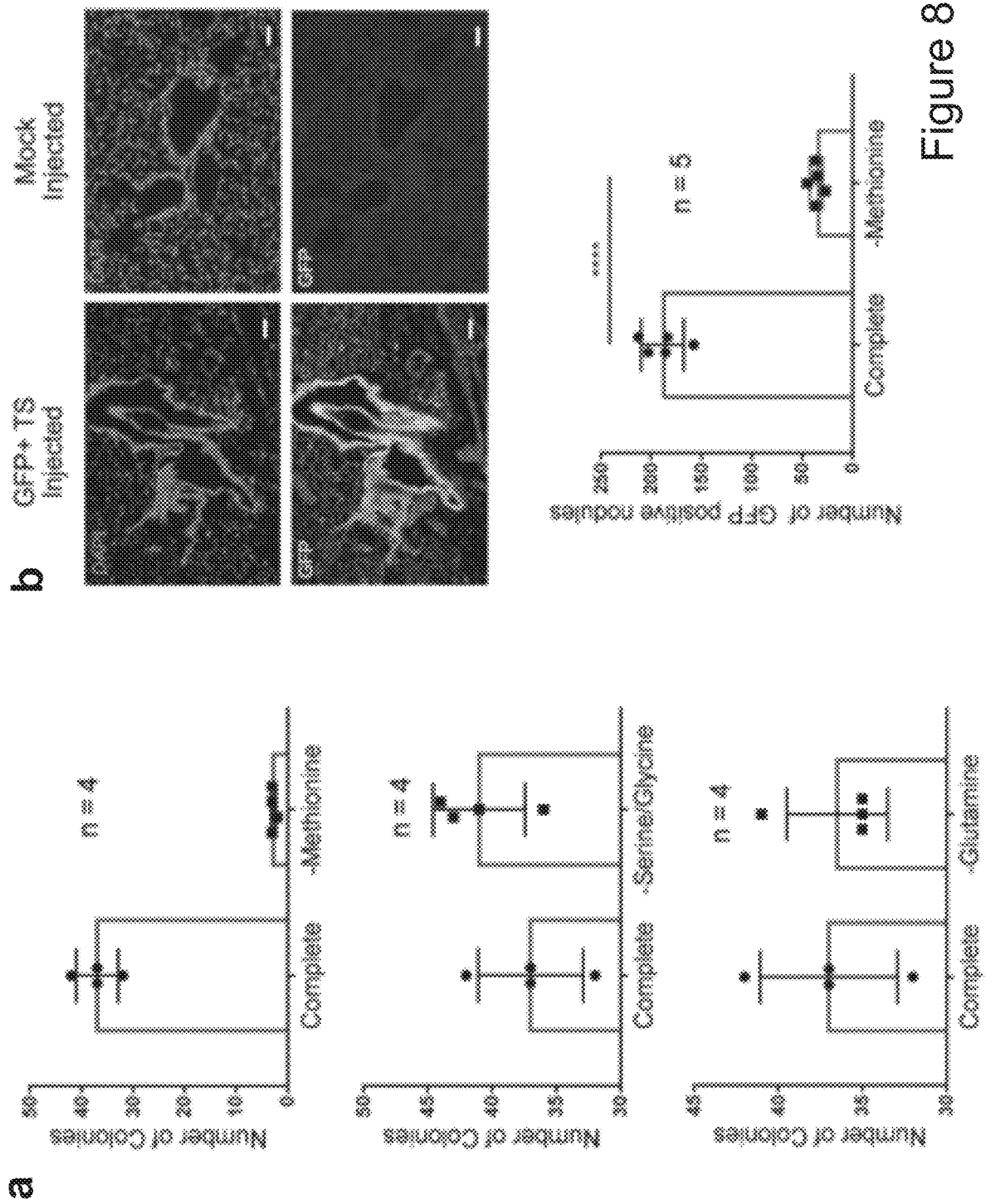
Figure 8(a)–(b)

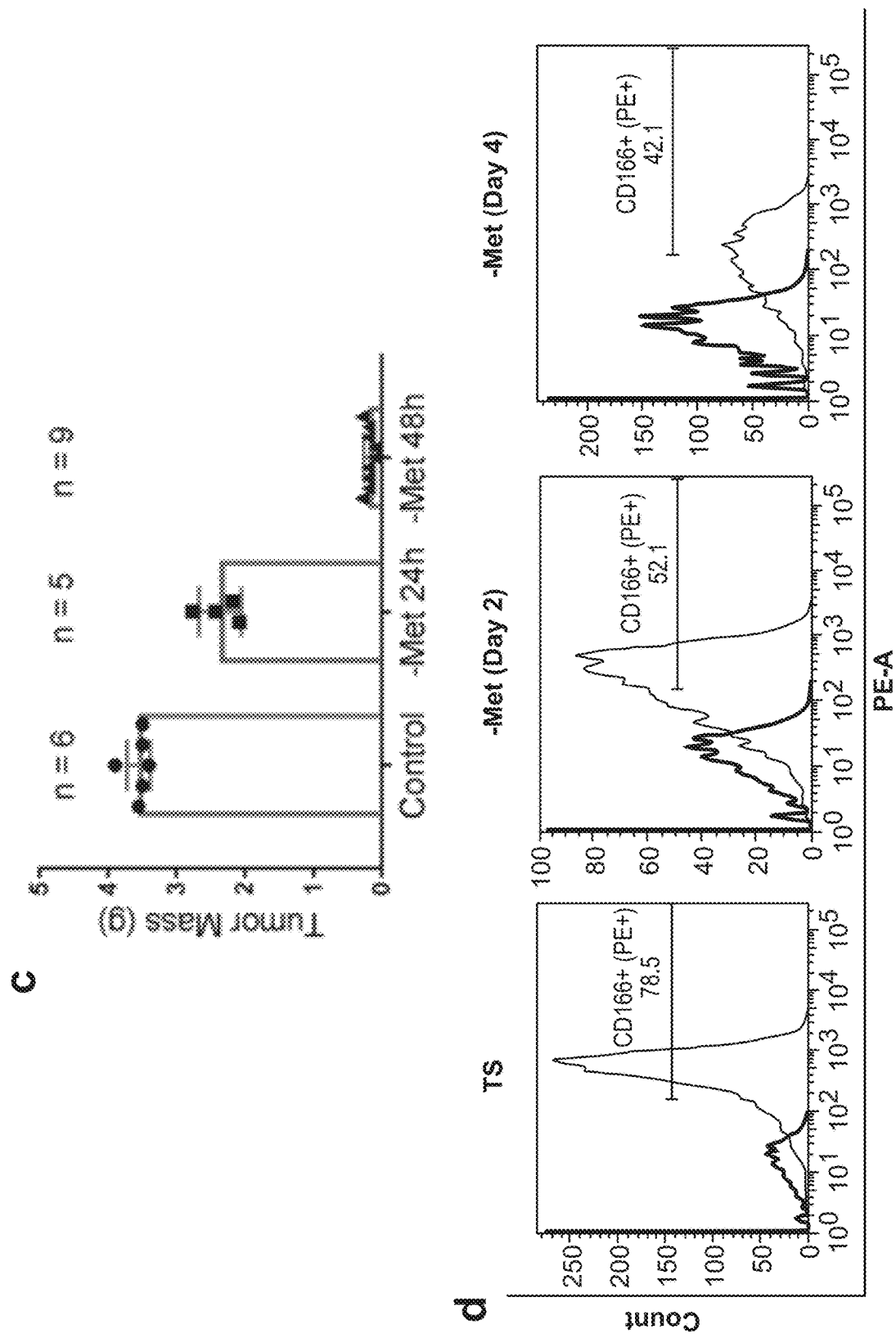
Figure 8(c)-(d)

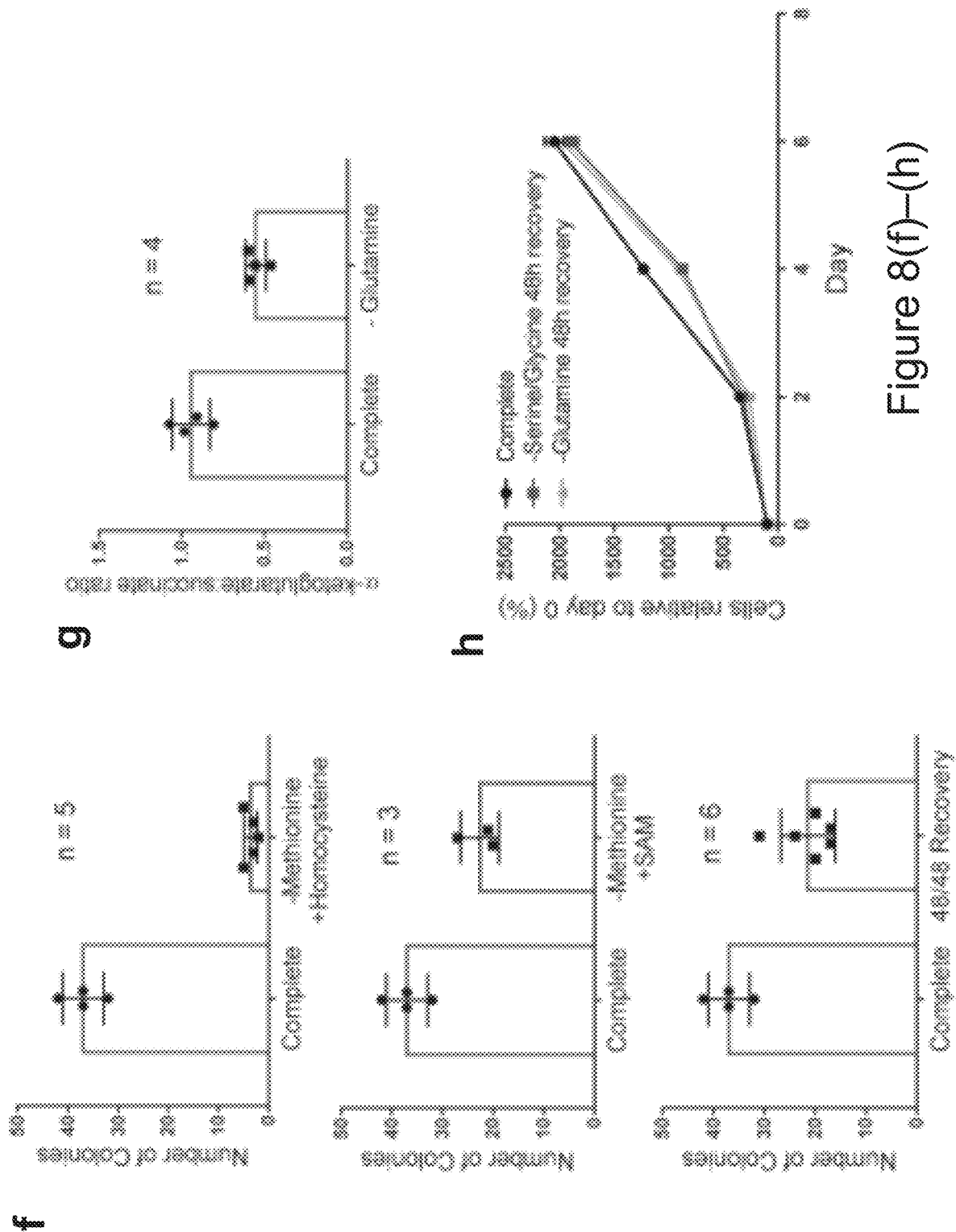
Figure 8(f)–(h)

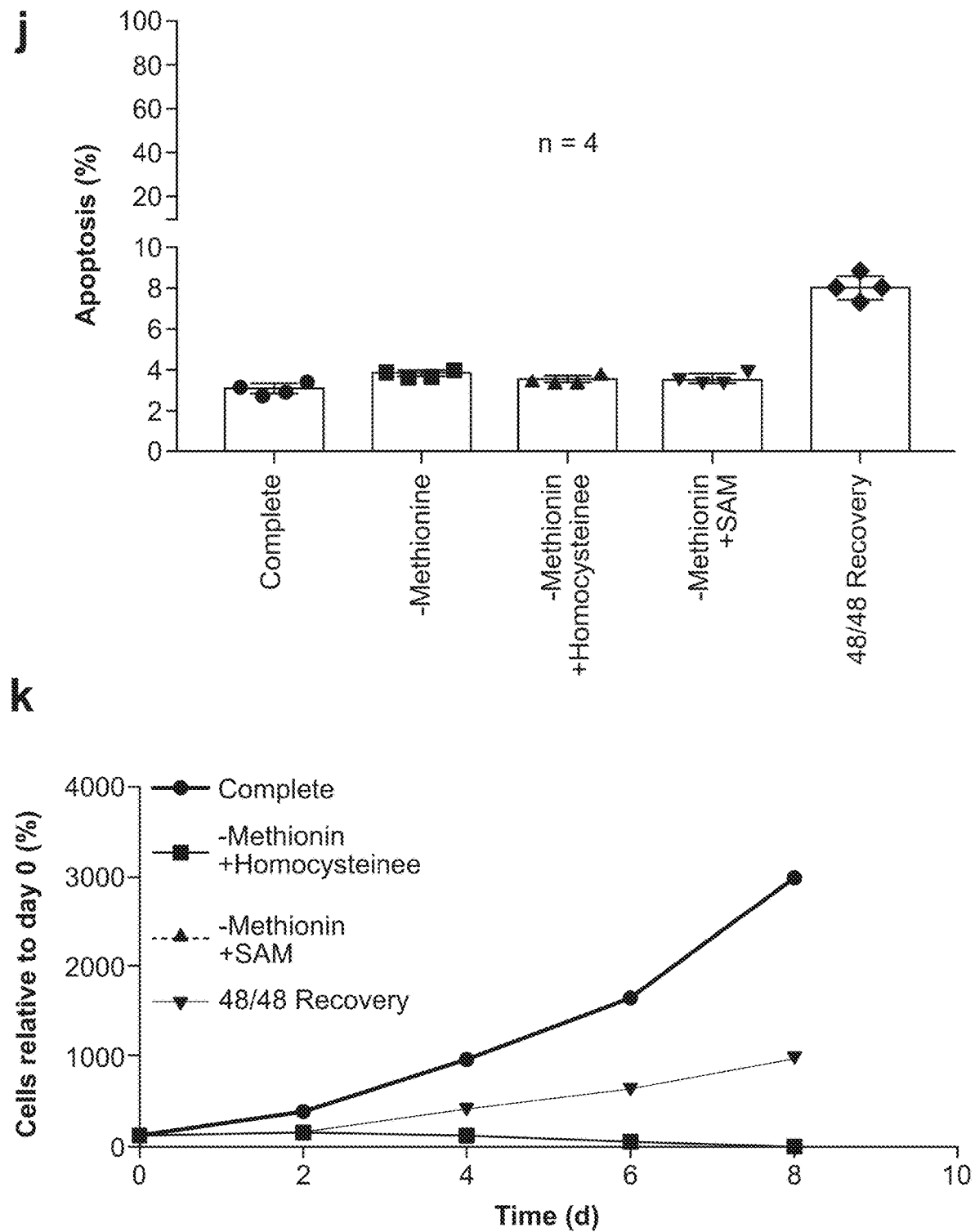
Figure 8(j)–(k)

a

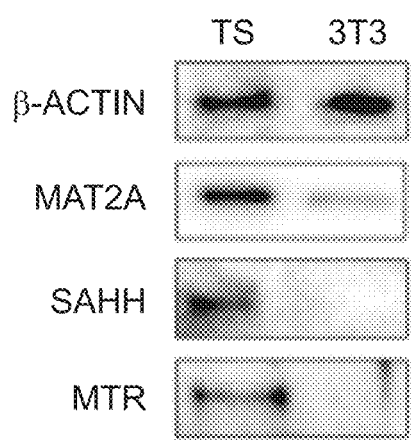
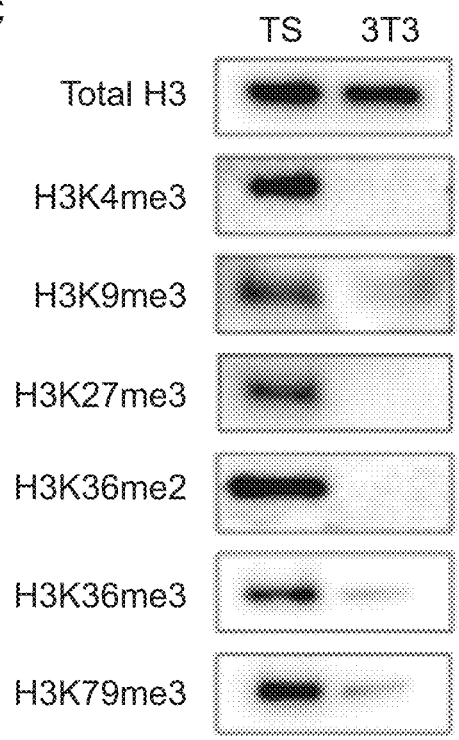
Figure 9(b)–(c)

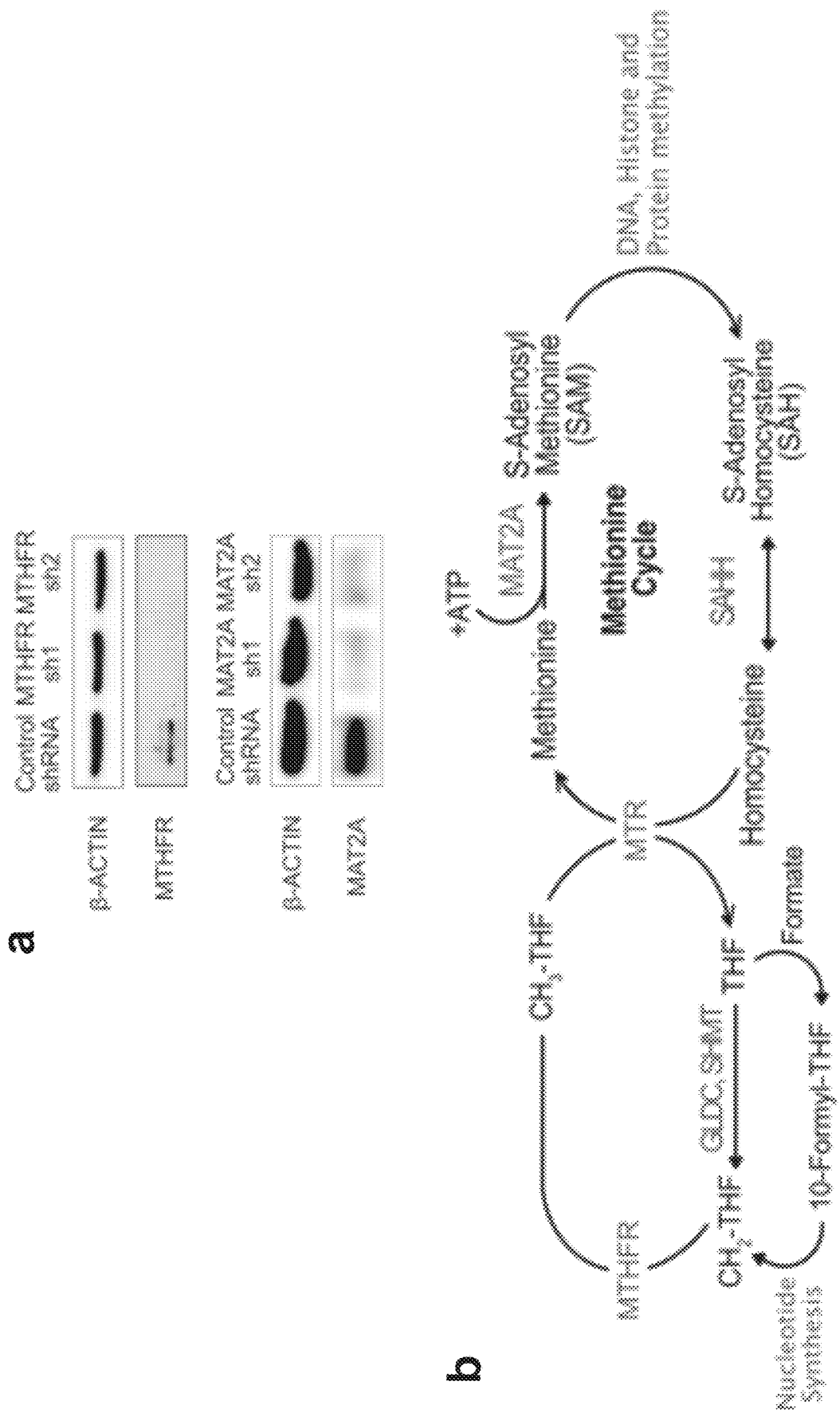
Figure 10(a)–(b)

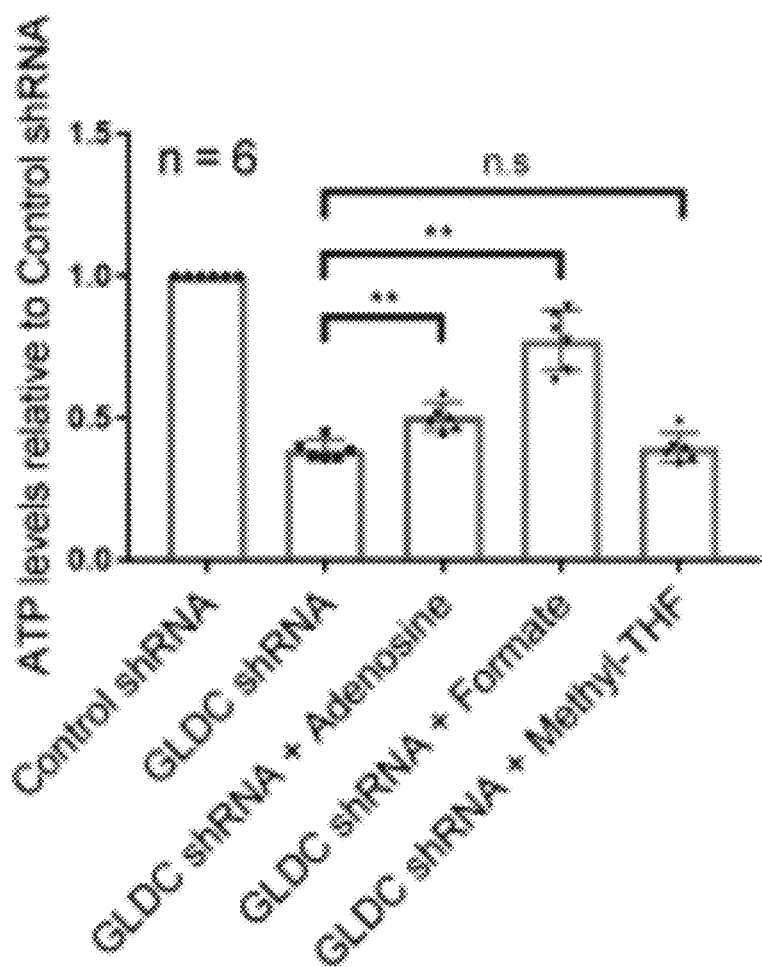
Figure 10(e)–(f)

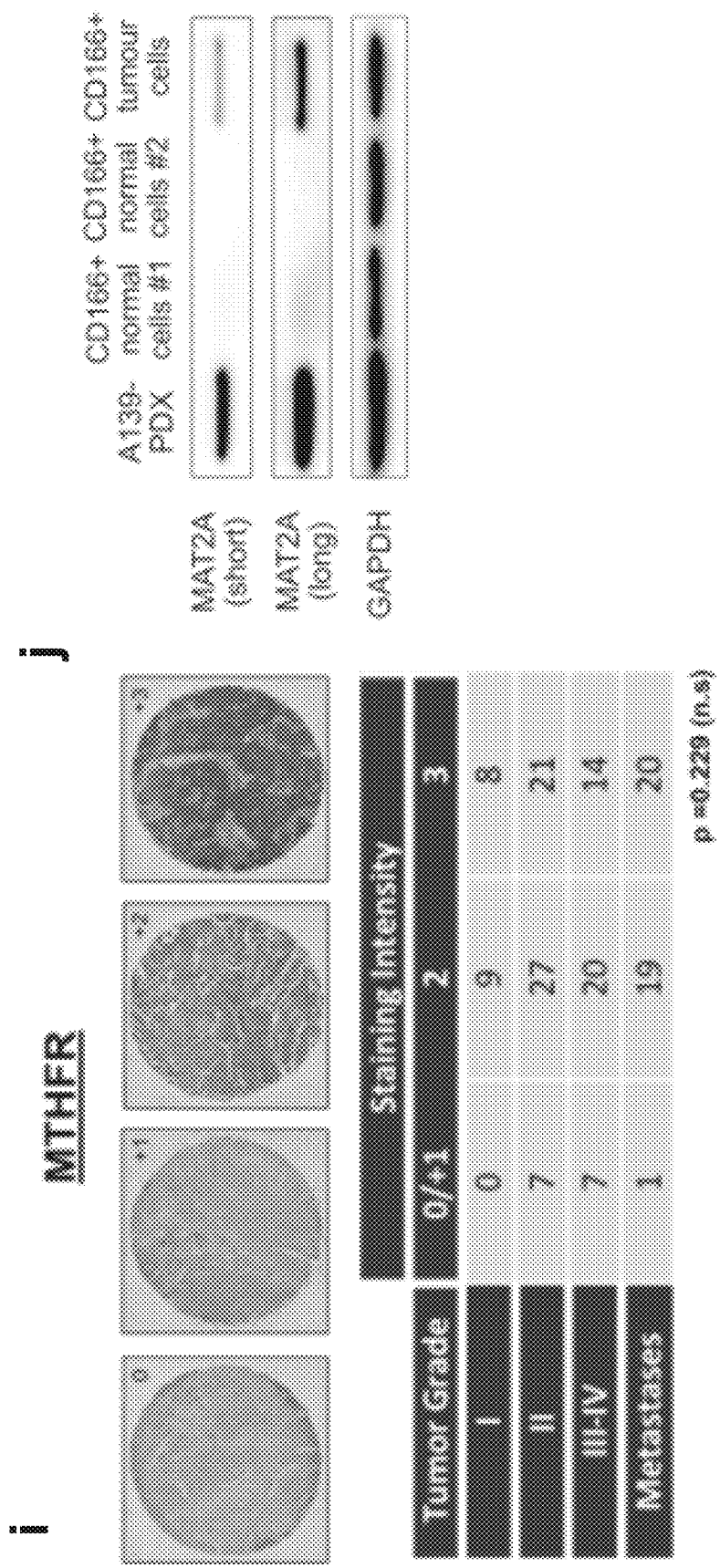
Figure 10(i)–(j)

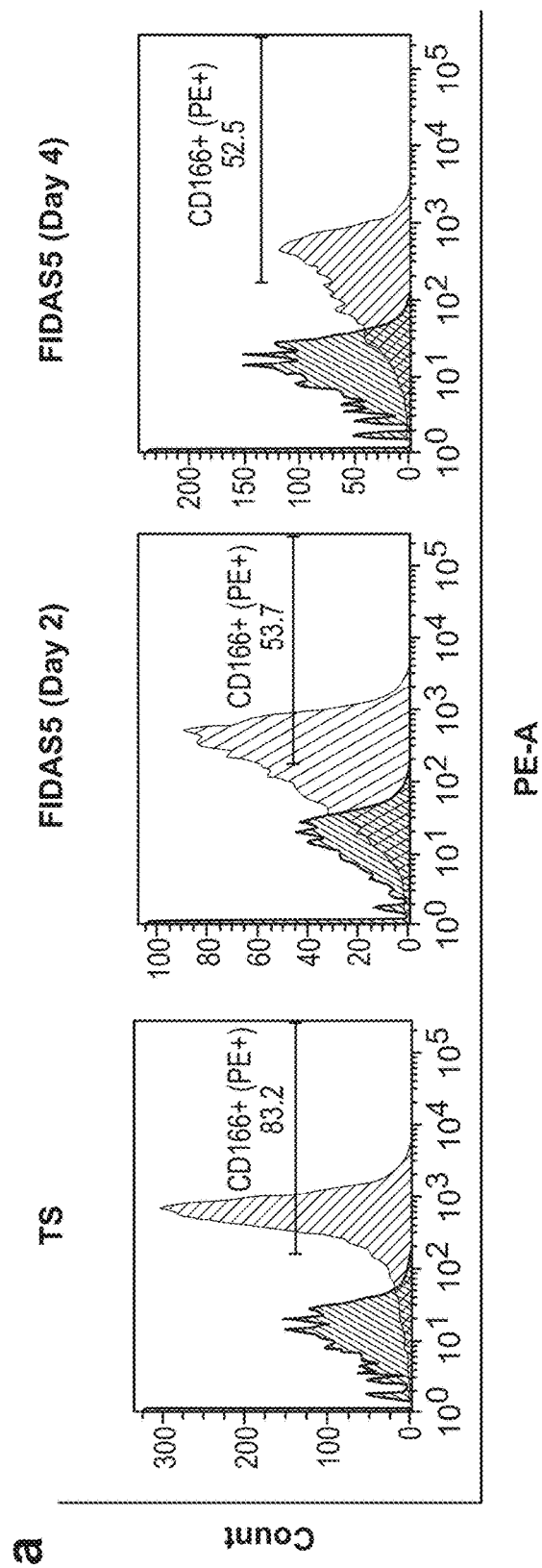
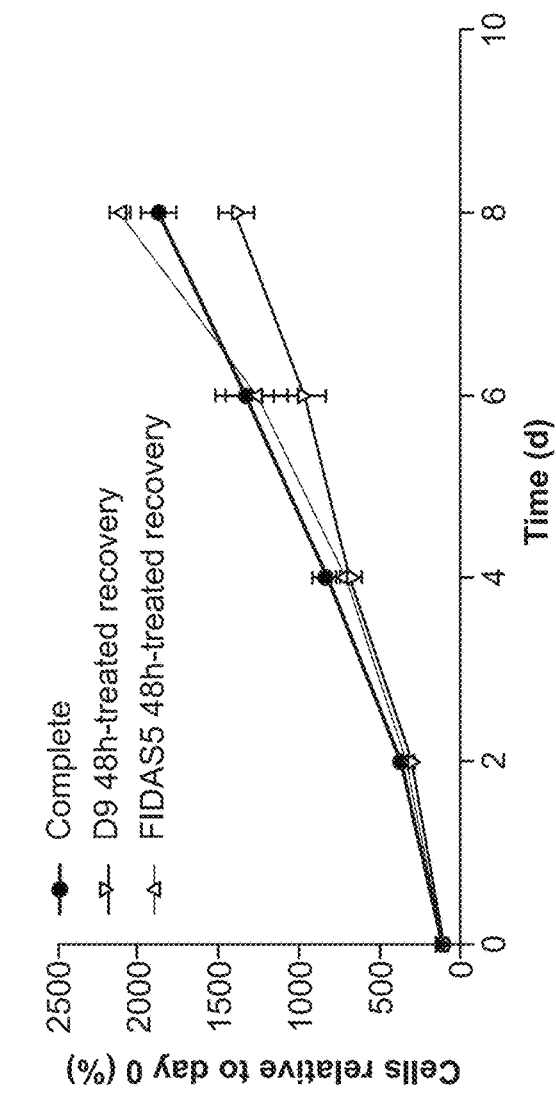
Figure 11(a)–(b)

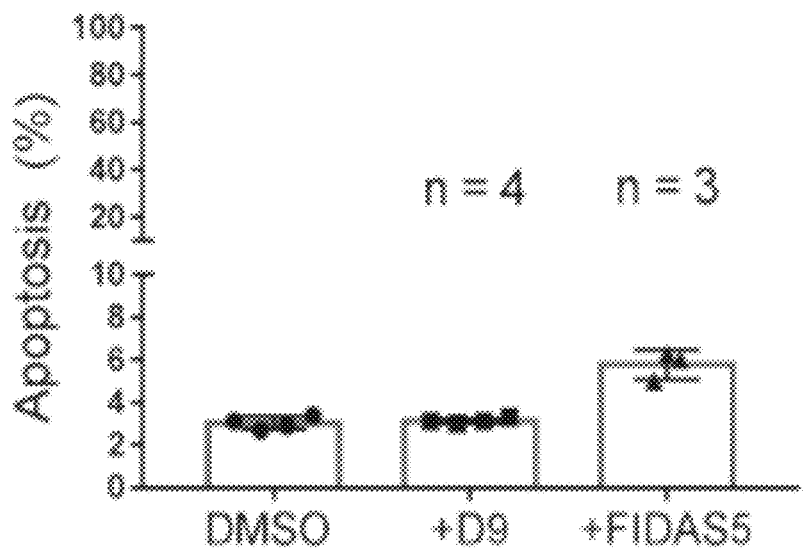
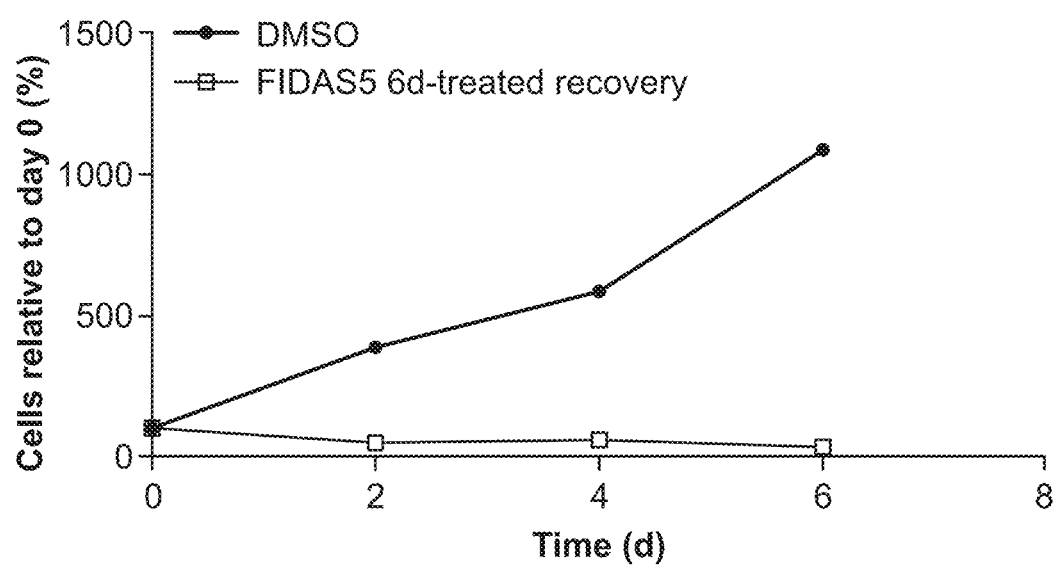
Figure 11(d)–(e)

US 11,872,230 B2

METHOD OF TREATING A METHIONINE-DEPENDENT CANCER

RELATED APPLICATION

This application is a continuation of U.S. patent application Ser. No. 16/039,916, filed Jul. 19, 2018. The entire contents of the foregoing application are hereby incorporated by reference herein.

SEQUENCE LISTING

The instant application contains a Sequence Listing which has been submitted electronically in ASCII format and is hereby incorporated by reference in its entirety. Said ASCII copy, created on May 12, 2022, is named 119134_02302_SL.txt and is 2,273 bytes in size.

BACKGROUND

Reference in this specification to any information known (or information derived from it), or to any matter which is known, is not, and should not be taken as an acknowledgement or admission or any form of suggestion that the prior information (or information derived from it) or known matter forms part of the common general knowledge in the field of endeavor to which this specification relates.

Cancer is the leading cause of death in the United States after cardiovascular disease. One in three Americans will develop cancer in his or her lifetime and one in five will die of cancer. Treatment of cancer can include surgery, chemotherapy, radiation therapy or targeted therapy (such as immunotherapy with a monoclonal antibody). The goal of treatment is to completely eradicate all traces of cancer from the patient. However, this is not always possible as there is often a risk of cancer recurrence.

In solid tumors such as lung, breast or colon cancers, there are often diverse intra-tumoral subpopulations of neoplastic cells, each having distinct functional properties that contribute towards malignant cancer progression. Among the different intra-tumoral subpopulations are tumor-initiating cells (TICs, otherwise known as cancer stem cells (CSCs)) which are responsible for tumor initiation. Tumor-initiating cells often have characteristics that are similar to normally stem cells that allow that to initiate tumors and drive malignant progression by generating and supporting replication of more differentiated non-stem cell progeny.

There is emerging evidence that TICs are often resistant to conventional chemotherapy and radiotherapy, thereby favouring relapse into more aggressive cancers. TICs in some cancers also appear to be highly invasive and can give rise to distant metastases.

There is therefore a need for the identification of novel approaches that target tumor-initiating CSCs for preventing and/or treating disease recurrence and distant metastatic spread.

SUMMARY

Provided herein is a therapeutic protocol for treating cancer or reducing the risk of recurrence of cancer in a subject following an anti-cancer therapy.

In one aspect, there is provided a method of treating cancer or reducing the risk of recurrence of cancer in a subject following an anti-cancer therapy, the method comprising the step of administering a methionine cycle inhibitor to the subject.

In one aspect, there is provided a method of reducing the therapeutic resistance of a subject to an anti-cancer therapy, the method comprising the step of administering a methionine-cycle inhibitor to the subject.

In one aspect, there is provided a method of inhibiting proliferation or eliminating a tumor initiating cell, the method comprising the step of contacting the tumor initiating cell with a methionine cycle inhibitor for a time and under conditions suitable for inhibiting proliferation or eliminating the tumor initiating cell.

In one aspect, there is provided a method of diagnosing and treating a methionine-dependent cancer, the method comprising the steps of: a) determining the expression levels of a biomarker selected from the group of MAT2A, MTHFR, MTR, SAHH, GLDC, SHMT2 and CD166 in a cancer cell obtained from a subject, wherein an increased expression level of a biomarker in a cancer cell as compared to the expression level of the biomarker in a non-cancerous cancer cell indicates that the subject has a methionine-dependent cancer, and b) administering a methionine cycle inhibitor to the subject found to have a methionine-dependent cancer.

BRIEF DESCRIPTION OF THE FIGURES

FIG. 1(b) is a graphical representation showing the abilities of TS, Adh and GLDC KD to form colonies in soft agar. Number of crystal-violet stained colonies after 2 months; 5000 cells per well were plated. Error bars denote s.d.; n=4.

FIG. 1(c) is a graphical representation showing the tumor mass following transplantation of 500,000 TS, Adh or GLDC KD cells into NSG mice 6 weeks post-transplantation, or when tumor length reaches 2 cm in diameter. Error bars denote s.d.; n=6 for all injections.

FIG. 1(f) is a schematic representation of the serine/glycine and methionine cycle pathways. Metabolic enzymes are in red.

FIG. 1(g) is graphical representation of the abundance of intracellular primary methionine cycle metabolites as determined by liquid chromatography-mass spectrometry (LC/MS), normalized to Adh cells. Data represent mean±s.d., and * denotes $p<0.05$,  denotes $p<0.01$, * denotes $p<0.001$, using multiple t-test and statistical significance corrected for multiple comparisons using the Holm-Sidak method, n=3

FIG. 1(h) is a graphical representation of the abundance of intracellular glutathione-associated metabolites as determined by LC/MS, normalized to Adh cells. Data represent mean±s.d., and * denotes p<0.05,  denotes p<0.01, * denotes p<0.001, using multiple t-test and statistical significance corrected for multiple comparisons using the Holm-Sidak method, n=3.

FIG. 1(*i*) is a photographic representation showing the protein expression of metabolic enzymes in TS, Adh and GLDC KD cells. β-actin was used as loading control.

FIG. 1(*j*) is a photographic representation showing the protein expression of modified histones in TS, Adh and GLDC KD cells. Histone H3 was used as loading control.

FIG. 2(*b*) is a graphical representation of the abundance of methionine cycle metabolites 48 h after methionine starvation, as determined by LC/MS, normalized to complete condition. Data represent mean±s.d., n=3.

FIG. 2(*c*) is a photographical representation of a western blot analyses of cells starved with the indicated metabolite for 48 h Total Histone H3 is used as loading control.

FIG. 2(*d*) is a photographic and graphical representation showing the effect of short-term metabolite starvation on TIC tumorigenicity. Tumor masses in NSG mice following the transplantation of 500,000 cells previously starved for 48 h. Tumors were weighed six weeks post-transplantation, or when they reached 2 cm in diameter. Error bars denotes s.d.; n=9 for methionine and ser/gly starvation; n=6 for glutamine starvation.

FIG. 2(*e*) is a graphical representation showing (i) top: Frequency of tumor initiating cells (TICs) present in TS and methionine starved TS cells. CI: Confidence interval. (ii) bottom: Tumor masses following subcutaneous implantation of cells. Starvation condition and number of cells are stated at the x-axis. For the injection of 10 k and 100 k cells, tumors were harvested 8 weeks after implantation; tumors from the injection of 500 k cells were harvested 6 weeks after implantation. Error bars denote s.d.; Number of injections are indicated on the left panel.

FIG. 2(*f*) is a graphical representation showing the tumor mass in NSG mice following the transplantation of 500,000 cells previously starved for 48 h. Starvation conditions are indicated at the x-axis, Error bars denote s.d.; n=5 for leucine, tryptophan and threonine starvation.

FIG. 2(*g*) is a photographic representation of western blot analyses of cells in the presence or absence of specific metabolites. Total Histone H3 is used as loading control. Cells were starved for 48 h or methionine but supplemented with homocysteine (HCY) (250 µM), S-adenosyl methionine (SAM; 500 µM) or replated into complete media for the next 48 h (48/48), FIG. 2(*h*) is a photographic and graphical representation of the effect of the presence or absence of specific metabolites on the colony- and tumor-forming abilities of TS cells. Tumor masses in NSG mice following the transplantation of 500,000 from cells cultured in different conditions. Tumors were weighed six weeks post-transplantation or when they reach 2 cm in diameter. Error bars denote s.d.; n=9 for −met+SAM, and 48/48 recovery conditions; n=5 for −met+ homocysteine condition.

FIG. 2(*i*) is a graphical representation of the assessment of apoptosis in metabolite-starved cells Top: Flow cytometry plots of TS cells stained with Annexin V·FITC/PI. Positive control cells are treated with 10 mM hydrogen peroxide for 48 h. Bottom: Percentage of Annexin-V positive cells is indicated in histograms below. Error bars denote s.d.; n=4.

FIG. 3(*b*) is a schematic representation of the experimental protocol (Top). Cells were starved overnight (16 h) in methionine-depleted medium. Uniformly $^{13}$C-labeled methionine was subsequently added and cells were analyzed thereafter. FIG. 3(*b*) shows a graphical representation of labeled methionine pulse-chase experiments (Bottom). Metabolite species detected are indicated on the right, and proportional abundance (% APE), is indicated on the left. Data represent mean±s.e.m., n=3 technical replicate measurements. Curves for two biological replicates are shown.

FIG. 3(*c*) shows the graphical representation of methionine dependence in TICs and NIH 3T3 cells. Cell numbers normalized to starting condition were assessed with the CellTiter-Glo. Error bars denote s.d.; n=6.

FIG. 3(*d*) is a schematic representation of the deuterium-labeled homocysteine molecules as it progresses through the methionine cycle. Labeled hydrogen atoms: pink stripes.

FIG. 3(*e*) is a graphical representation of the proportional abundance (% APE) of metabolite species, detected through labeled homocysteine pulse-chase experiments in TS32 and NIH 3T3 cells. Data represent mean±s.e.m., n=3 technical replicate measurements. Curves for two biological replicates are shown.

FIG. 4(*b*) shows a graphical representation of tumor mass in NSG mice following transplantation of TS, GLDC KD and SAM supplemented GLDC-KD cells. Tumors were weighed 6 weeks post-transplantation or when they reached 2 cm in diameter. Error bars denote s.d.; n=6.

FIG. 4(*c*) shows a photographical representation of a western blot analysis of GLDC KD cells supplemented with SAM. SAM (500 µM) was supplemented to GLDC KD cells for 48 h and then harvested. GAPDH was used as loading control.

FIG. 4(*d*) shows a graphical representation of the proportional abundance (% APE) of metabolite species, detected through labeled homocysteine pulse-chase experiments in TS32 and GLDC KD and MTHFR KD cells. Data represent mean±s.e.m., n=3 technical replicate measurements. Curves for two biological replicates are shown.

FIG. 4(*e*) shows a photographical representation of a western blot analysis of the effect of MTHFR overexpression in GLDC KD cell lines. GAPDH is used as loading control for MTHFR and GLDC immunoblots. Total H3 is used as loading control for the rest.

FIG. 4(*f*) shows a graphical representation of tumor mass in NSG mice following transplantation of 500,000 TS, GLDC KD and GLDC KD cells overexpressing MTHFR. Tumors were weighed 6 weeks post-transplantation or when they reached 2 cm in diameter. Error bars denote s.d.; n=7 for GLDC KD+MTHFR cells.

FIG. 4(*g*) is a photographic representation of a western blot analysis of MTHFR and MAT2A shRNA knockdown stable cell lines. Total H3 is used as loading control.

FIG. 4(*h*) is a graphical representation of the effect of MTHFR and MAT2A knockdown on tumor formation abilities of TS cells. Top: Number of crystal-violet stained colonies formed from knockdown cells; 5000 cells per well were plated. Error bars denote s.d.; n=3. Bottom: Tumor mass in NSG mice following transplantation of 500,000 TS, MTHFR KD or MAT2A KD cells. Tumors were weighed 6 weeks post-transplantation, or when they reached 2 cm in diameter. Error bars denote s.d.; n=6 for all injections.

FIG. 5(a) is a schematic representation of the methionine cycle and targets (in blue) of small molecules inhibitors (in red) used in the study.

FIGS. 5 (b) and (c) are graphical representations of the abundance of methionine cycle metabolites 48 h after inhibitor treatment, as determined by LC/MS, normalized to DMSO treated cells. Data represent mean±s.d., n=3 and n=6 for D9 and FIDAS5 inhibitor treatment, respectively.

FIG. 5(e) and (1) are graphical representations of the effect of methionine cycle-related inhibitors and metabolites on the tumorigenic capabilities of lung cancer TICs. Top: Number of crystal-violet stained colonies formed from cells treated with inhibitor prior to colony-forming assay; 5000 cells per well were plated. Error bars denote s.d.; n=8 for D9 and n=3 for FIDAS conditions. Bottom: Tumor mass in NSG mice following transplantation of 500,000 cells treated with inhibitor. Tumors were weighed 6 weeks post-transplantation, or when they reached 2 cm in diameter. Error bars denote s.d.; n=6 for D9 treated cells; n=9 for FIDAS treated cells.

FIG. 5(i) shows a graphical representation of intraperitoneal administration of compounds into mice subcutaneously implanted with $5\times10^5$ lung TICs. They were administered with 40 mg/kg FIDAS5, 4 mg/kg of cisplatin or 100 μl corn oil vehicle for three days. Tumors were weighed 6 weeks post-transplantation, or when they reached 2 cm in diameter. Error bars denote s.d.; n=6 for FIDAS5 and control (corn oil vehicle) injections; n=9 for cisplatin injection.

FIG. 5(j) shows a graphical representation of intraperitoneal administration of FIDAS5 (40 mg/kg) into mice subcutaneously implanted with $5\times10^5$ lung patient-derived xenograft (PDX) cells for three days. Identity of PDX line is stated on the x-axis. Tumors were weighed 6 weeks post-transplantation, or when they reached 2 cm in diameter. Error bars denote s.d.; n=5 for A139 corn oil injection; n=7 for A139 with FIDAS5 injections; n=8 respectively for all A233 tumors.

FIG. 6(b) is a table of cell lines and sensitivity to FIDAS5 measured by IC50, together with MAT2A abundance and MTAP status, and determined an IC50 value of less than 15 μM for susceptibility to FIDAS5 inhibition.

FIG. 6(c) is a dot-plot correlating MAT2A abundance and/or MTAP status of cell lines to their susceptibility to FIDAS5 inhibition as indicated by their IC50 values.

FIG. 6(d) shows contingency tables correlating MAT2A abundance and/or MTAP status to susceptibility to FIDAS5 inhibition. Fischer's exact test's p value is indicated at the bottom right.

FIG. 7(c) is a photographic and graphical representation of the relative abundance of steady-state ATP levels upon SHMT2 and GLDC knockdown in TS cells. Top: Immunoblots of SHMT2 knockdown in TS cells. ATP levels were measured using the Cell-Titer Glo (Promega) reagent from 1000 cells per well (counted as one technical replicate) for a total of 10 wells. Error bars denote s.d., n=6. Formate was supplemented at a final concentration of 0.5 mM.

FIG. 7(d) is a photographic and graphical representation of the relative abundance of steady state ATP levels in Adh cells. Top: Immunoblots of SHMT2 or GLDC re-expression in Adh cells. ATP levels were measured using the Cell-Titer Glo (Promega) reagent from 1000 cells per well (counted as one technical replicate) for a total of 10 wells. Error bars denote s.d., n=5. Formate was supplemented at a final concentration of 0.5 mM.

FIG. 7(e) is a graphical representation of tumor mass following transplantation of 500,000 Adh Empty Vector or GLDC expressing Adh cells into NSG mice 6 weeks post-transplantation. Error bars denote s.d.; n=5 for all injections.

FIG. 7(f) is a photographic representation of western blot analysis of Adh and Ts cells grown for 72 h in indicated media conditions. Histone H3 is used as loading control.

FIG. 8(a) is a graphical representation of the effect of short-term metabolite starvation on TIC tumorigenicity. Number of crystal-violet stained colonies formed from cells starved prior to the experiments; 5000 cells per well were plated. Error bars denote s.d.; n=4 for all conditions.

FIG. 8(b) is a photographic and graphical representation of analyses of orthotopically implanted GFP-expressing TS cells in lungs of NSG mice 5 weeks post implantation. Top panel shows immunofluorescence staining of representative GFP positive lesions (left) and a GFP-negative mouse bronchiole of a mouse mock-injected with PBS. White scale bars, 40 μm. Bottom histogram shows the number of GFP-expressing lesions in mice injected with TS cells grown for 48 h in indicated media conditions. Error bars denote s.d., n=5 for all injections. **** denotes p=0.0001 by Student's t test.

FIG. 8(c) is a graphical representation of tumor mass in NSG mice following transplantation of TS cells starved of methionine for 24 or 48 h. Tumors were weighed 6 weeks post-transplantation, or when they reached 2 cm in diameter. Error bars denote s.d.; n=6 for unstarved TS cells, n=5 for 24-hour starved TS cells; n=9 for 48-hour starved TS cells.

FIG. 8(d) is a graphical representation of CD166 staining of TS cells in methionine starved and complete conditions. Representative flow cytometry plots of indicated cells are shown. CD166 negative control (unstained TS cells) is presented in blue.

FIG. 8(f) is a graphical representation of the effect of short-term metabolite starvation on TIC tumorigenicity. Number of crystal-violet stained colonies formed from cells starved prior to the experiments; 5000 cells per well were plated. Error bars denote s.d.; n=5 for −met+homocysteine, n=3 for −met+SAM and n=6 for 48/48 recovery conditions.

FIG. 8(g) is a graphical representation of an analysis of α-ketoglutarate/succinate ratio in TS cells starved of glutamine. Error bars denote s.d.; n=4 for all conditions.

FIG. 8(h) is a graphical representation of the proliferation of TS cells transiently starved of indicated amino acids for 48 h and then replated into complete media for another 48 h. Cell numbers normalized to starting number were assessed every two days using the CellTiter-Glo (Promega) luminescence reagent. Error bars denote s.d.; n=6.

FIG. 8(j) is a graphical representation of apoptosis in cells cultured under methionine-rescue conditions. The percentage of Anexin-V positive cells cultured under methionine rescue conditions. Error bars denote s.d.; n=4.

FIG. 8(k) is a graphical representation of the proliferation of TS cells grown continuously under methionine rescue conditions. Cell numbers normalized to starting number were assessed every two days using the CellTiter-Glo luminescence reagent. Error bars denote s.d.; n=6.

FIG. 9(b) is a photographic representation showing the comparison of methionine cycle enzyme abundances between TS and NIH 3T3 cells. Representative immunoblots of indicated enzymes were performed on TS and NIH 3T3 cell lines. β-actin was used as loading control.

FIG. 9(c) is a photographic representation showing protein expression of methylated histones in TS and NIH 3T3 cells. Histone H3 was used as loading control.

FIG. 10(a) is a photographic representation showing the knockdown of MTHFR and MAT2A in TS cells. Representative immunoblots of metabolic enzymes as indicated on the left were performed on Control shRNA and two MAT2A or MTHFR shRNA-expressing lines. β-actin was used as loading control.

FIG. 10(b) is a schematic representation of the one-carbon pathway in relation to the methionine cycle. Metabolites used in the metabolite rescue experiments are indicated in blue.

FIG. 10(e) is a graphical representation of the relative abundance of steady state ATP levels in Control KD, GLDC KD and MTHFR overexpressing+GLDC KD supplemented with formate (0.5 mM), methyl-THF (20 μM) or Adenosine (200 μM). ATP levels were measured using the Cell-Titer Glo (Promega) reagent from 1000 cells per well (counted as one technical replicate) for a total of 10 wells. Error bars denote s.d., n=6. ** denotes p=0.005 by Student's two-tailed t-test.

FIG. 10(f) is a photographic representation of the knockdown of MAT2A in NIH 3T3 and Adh cells. Representative immunoblots of metabolic enzymes as indicated on the left were performed on Control shRNA and two MAT2A shRNA-expressing lines. GAPDH was used as loading control.

FIG. 10(i) is a photographic representation of MTHFR immunohistochemistry of a NSCLC tumor microarray (n=153). Representative images and staining intensity grades (indicated in the upper right corner) shown at the top. A contingency table correlating the staining intensity of MAT2A with grade of NSCLC is shown below. Chi-square p value is indicated at the bottom right FIG. 10(j) is a photographic representation of the comparison of MAT2A abundance between primary tissues. Representative immunoblots of MAT2A was performed on A139, a patient derived lung cancer xenograft (PDX), CD166+ cells from a normal human lung biopsy sample, or CD166+ cells from a human lung cancer biopsy sample. GAPDH was used as loading control.

FIG. 11(a) is a graphical representation of CD166 staining of TS cells in FIDAS or vehicle (DMSO) treated conditions. Representative flow cytometry plots of indicated cells are shown. CD166 negative control (unstained TS cells) is presented in blue.

FIG. 11(b) is a graphical representation of the proliferation of TS cells transiently treated with methionine cycle inhibitors for 48 h and then replated into complete media for another 48 h. Cell numbers normalized to starting number were assessed every two days using the CellTiter-Glo. Error bars denote s.d.; n=10.

FIG. 11(e) is a graphical representation of TS cells were first treated for 6 days with FIDAS5 and then replated into complete medium for 48 h. Their proliferation was subsequently assessed every two days using the CellTiter-Glo luminescence reagent. Cell numbers normalized to starting number are shown. Error bars denote s.d.; n=10.

DETAILED DESCRIPTION

Figure 1A:
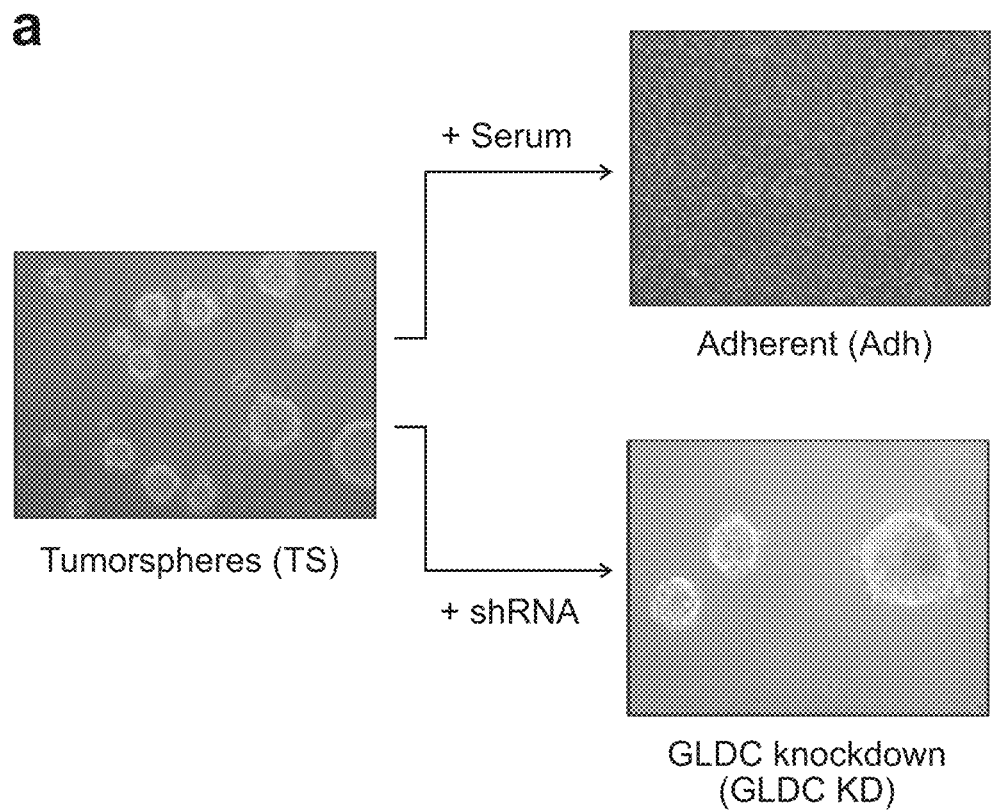
FIG. 1(a) is a photographical representation of two cell lines that were derived from tumorspheres (TS, left): Adherent (Adh, top right) cells that were generated by continual passaging of TS in serum supplemented TS media without growth factors, and TS transduced with a shRNA hairpin against glycine decarboxylase (GLDC) (GLDC KD, bottom right).

The present invention relates to a therapeutic protocol for treating or reducing the risk of recurrence of cancer in a subject.

In one aspect, there is provided a method of treating cancer or reducing the risk of recurrence of cancer in a subject following an anti-cancer therapy, the method comprising the step of administering a methionine cycle inhibitor to the subject.

In one example, the method comprises treating a cancer. In one example, the method comprises treating a recurrent cancer. In one example, the method comprises treating a cancer in a subject following an anti-cancer therapy.

Without being bound by theory or mode of action, the invention is predicated in part on the determination that some cancer cells, such as in tumor initiating cells, can have highly elevated methionine cycle activity and trans-methylation rates that are driven by key metabolic enzymes. High methionine cycle flux can cause methionine consumption to far outstrip its regeneration leading to a heavy dependence on exogenous methionine for tumor-initiation (i.e. methionine dependence), resulting in a metabolic liability. Pharmacological inhibition of the methionine cycle may be sufficient to cripple the tumor-capability of these cells. In particular, a short term or transient inhibition of the methionine cycle may be sufficient to treat or prevent the recurrence or metastasis of cancer as these cells are highly dependent on the methionine cycle for survival and proliferation.

The terms "cancer" and "cancerous" refer to or describe the physiological condition in mammals that is typically characterized in part by unregulated cell growth. As used herein, the term "cancer" refers to non-metastatic and metastatic cancers, including early stage and late stage cancers. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer. By "early stage cancer" is meant a cancer that is not invasive or metastatic or is classified as a Stage 0, I, or II cancer. The term "late stage cancer" generally refers to a Stage III or Stage IV cancer, but can also refer to a Stage II cancer or a sub-stage of a Stage II cancer. One skilled in the art will appreciate that the classification of a Stage II cancer as either an early stage cancer or a late stage cancer depends on the particular type of cancer. Illustrative examples of cancer include, but are not limited to, breast cancer, prostate cancer, ovarian cancer, cervical cancer, pancreatic cancer, colorectal cancer, lung cancer, hepatocellular cancer, gastric cancer, liver cancer, bladder cancer, cancer of the urinary tract, thyroid cancer, renal cancer, carcinoma, melanoma, brain cancer, non-small cell lung cancer, squamous cell cancer of the head and neck, endometrial cancer, multiple myeloma, rectal cancer, and esophageal cancer.

In an example, the cancer is lung cancer. In an example, the cancer is a metastatic cancer. In an example, the cancer is a metastatic lung cancer.

In an example, the cancer is non small cell adenocarcinoma.

In one example, the cancer is a breast cancer. The cancer may be metastatic breast cancer. In one example, the cancer is a triple-negative breast cancer.

In an example, the cancer or metastatic cancer is driven by a tumor initiating cell (TIC).

In one example, the cancer is a chemotherapy or drug resistant cell.

The term "tumor initiating cell", "TIC", "cancer stem cell" or "CSC" refers to a cell that has tumor-initiating and tumor-sustaining capacity, including the ability to extensively proliferate, form new tumors and maintain cancer development, i.e., cells with indefinite proliferative potential that drive the formation and growth of tumors. CSCs are biologically distinct from the bulk tumor cells and possess characteristics associated with stem cells, specifically the ability to self renew and to propagate and give rise to all cell types found in a particular cancer sample. The term "cancer stem cell" or CSC includes both gene alteration in stem cells (SCs) and gene alteration in a cell which becomes a CSC.

The term "recurrence" as used herein may refer to a cancer that has recurred (come back), usually after a period of time during which the cancer could not be detected. The cancer may be called a recurrent cancer. The recurrent cancer may come back to the same place as the original (primary) tumor or to another place in the body. The recurrence may be considered a "local recurrence" when the cancer is in the same place as the original cancer or very close to it. The recurrence may be a "regional recurrence" when the tumor has grown into lymph nodes or tissues near the original cancer. The recurrence may be called a distant recurrence when the cancer has spread to organs or tissues far from the original cancer. When the cancer spreads to a distant place in the body, the recurrent cancer may be called metastasis or metastatic cancer.

The "reduction" of the risk of cancer recurrence following an anti-cancer therapy can be quantified in terms of a reduction in percentage (%) risk of cancer recurrence. For example, there can be a reduction in a risk of cancer recurrence by anywhere from about 1% to 100%. In an example, there is a reduction in risk of cancer recurrence by 5%, 10%, 15%, 20%, 25%, 30%, 35%, 40%, 45%, 50%, 55%, 60%, 65%, 70%, 75%, 80%, 85%, 90%, 95% or 100% or a percentage inbetween.

In an example, the administration of a MAT2A inhibitor leads to a reduction of percentage risk of cancer recurrence following anti-cancer therapy by a percentage of 5%, 10%, 15%, 20%, 25%, 30%, 35%, 40%, 45%, 50%, 55%, 60%, 65%, 70%, 75%, 80%, 85%, 90%, 95% or 100% or a percentage inbetween.

The term "administering" refers to contacting, applying or providing a MAT2A inhibitor to a subject.

The methods as defined herein may comprise "transient administration" of a MAT2A inhibitor to a subject. The terms "transiently administering" or "transient administration" refers to the short-term administration of a methionine-cycle inhibitor to provide a more long lasting benefit to a subject being treated with an anti-cancer therapy and reduce the risk of recurrence or relapse of cancer. This may be done so by restricting administration to a relatively narrow window of time.

The "transient administration" of a methionine cycle inhibitor to a subject may lead to lower levels of toxicity and side effects.

A therapeutically effective amount of an inhibitor of methionine cycle enzyme expression or activity, in a pharmaceutically acceptable preparation, may be administered to the subject only "transiently". "Transient administration" may be restricted to a finite, predetermined treatment period, and may constitute a predefined dose regimen of one or more doses of the inhibitor. The treatment period has a duration measured from the beginning of the first (or only) dose to the end of the last (or only) dose, with the duration expressed as an integer number of days after rounding up to the nearest whole day. (In other words, a treatment period beginning and ending in less than 24 hours has a duration of one day.) A suitable duration for the treatment period may be less than about 2 or 1 month(s); less than about 3, 2, or 1 week(s); or less than about 6, 5, 4, 3, or 2 days; among others. Accordingly, the treatment period may be only one day and/or a single dose. In some embodiments, the duration of the treatment period may be at least about 2, 3, 4, or 5 days; or at least about 1, 2, 3, or 4 weeks.

The term "subject" as used throughout the specification is to be understood to mean a human or may be a domestic or companion animal. While it is particularly contemplated that the methods of the invention are for treatment of humans, they are also applicable to veterinary treatments, including treatment of companion animals such as dogs and cats, and domestic animals such as horses, cattle and sheep, or zoo animals such as primates, felids, canids, bovids, and ungulates. The "subject" may include a person, a patient or individual, and may be of any age or gender.

In one example, there is provided a method of reducing the risk of recurrence of cancer in a subject following an anti-cancer therapy, the method comprising the step of transiently administering a methionine cycle inhibitor to the subject.

In one example, there is provided a method of treating a recurrent cancer in a subject, the method comprising administering a methionine cycle inhibitor to the subject.

In one example, there is provided a method of treating a recurrent cancer in a subject, the method comprising the step of transiently administering a methionine cycle inhibitor to the subject.

In one example, there is provided a method of treating a metastatic cancer in a subject, the method comprising administering a methionine cycle inhibitor to the subject.

In one example, there is a provided a method of treating a metastatic cancer in a subject, the method comprising the step of transiently administering a methionine cycle inhibitor to the subject.

In one example, there is provided a method of treating a methionine-dependent cancer in a subject, the method comprising the step of administering a methionine cycle inhibitor to the subject.

In one example, there is provided a method of treating a methionine-dependent cancer in a subject, the method comprising the step of transiently administering a methionine cycle inhibitor to the subject.

The term "methionine-dependent" may refer to a cancer that is unable to grow, proliferate or survive in the absence of methionine. It may refer to a cancer that is dependent on methionine cycle enzymes, including MAT2A, MTHFR, SAHH and MTR. "Methionine-dependent" may also refer to a cancer that is unable to grow, proliferate or survive as a result of the inhibition of the methionine cycle enzymes, such as MAT2A, MTHFR, SAHH or MTR.

In one example, the cancer is a MAT2A dependent cancer. In one example, the cancer is a MTHFR dependent cancer. In one example, the cancer is a SAHH dependent cancer. In one example, the cancer is a MTR dependent cancer.

The cancer cell may demonstrate high methionine cycle activities, as determined by methionine, SAM, SAH, and homocysteine levels, which can be measured by mass spectrometry and biochemical assays. The cancer cell may also demonstrates high methionine cycle activities, as determined by biochemical methylation assays of methylated histones and methylated DNA The terms "co-administered" and "administered concurrently" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimetres, including from within about 0.5 to about 5 centimetres. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

In one example, the method comprises administering the methionine cycle inhibitor to a cancer cell. In one example, the cancer cell is a tumour initiating cell. In one example, the method comprises administering the methionine cycle inhibitor to a tumor initiating cell. In an example, the tumor initiating cell is a lung tumor initiating cell.

The cancer cell may express MAT2A and/or CD166, or other known tumour initiating cell markers. In one example, the cancer expresses a biomarker selected from the group consisting of MAT2A and CD166. In one example, the cancer cell expresses MAT2A and CD166. In one example, the cancer cell expresses MAT2A. In one example, the cancer cell expresses CD166.

The tumour initiating cell may express MAT2A and/or CD166, or other known tumour initiating cell biomarkers. In one example, the tumour initiating cell expresses a biomarker selected from the group consisting of MAT2A and CD166. In one example, the cancer cell expresses MAT2A and CD166. In one example, the cancer cell expresses MAT2A. In one example, the cancer cell expresses CD166.

In one example, the cancer comprises a tumor initiating cell.

In one example, the cancer is resistant to chemotherapy or radiotherapy.

In one example, the cancer is a metastatic or recurrent cancer.

In one example, the cancer is a methionine-dependent cancer.

In one example, the tumour initiating cell is methionine-dependent.

In an example, the tumor initiating cell is methylthioadenosine phosphorylase (MTAP) positive. MTAP is an enzyme found in all normal tissues that catalyzes the conversion of methylthioadenosine (MTA) into adenine and 5-methylthioribose-1-phosphate. The adenine is salvaged to generate adenosine monophosphate, and the 5-methylthioribose-1-phosphate is converted to methionine and formate. In one example, the tumor initiating cell expresses MAT2A and is MTAP positive.

In one example, the cancer cell expresses a biomarker selected from the group consisting of MAT2A, MTHFR, MTR, SAHH, GLDC, SHMT2 and CD166.

In one example, the methionine cycle inhibitor is an inhibitor of MAT2A, MTHFR, MTR, SAHH, GLDC, SHMT2 or CD166.

In one aspect, there is provided a method of diagnosing and treating a methionine-dependent cancer, the method comprising the steps of: a) determining the expression levels of a biomarker selected from the group of MAT2A, MTHFR, MTR, SAHH, GLDC, SHMT2 and CD166 in a cancer specimen obtained from a subject, wherein an increased expression level of a biomarker in the cancer specimen as compared to the expression level of the biomarker in a non-cancerous cancer specimen indicates that the subject has a methionine-dependent cancer, and b) administering a methionine cycle inhibitor to the subject found to have a methionine-dependent cancer.

In one example, there is provided a methionine cycle inhibitor for use in treating a methionine-dependent cancer, wherein the expression levels of a biomarker selected from the group of MAT2A, MTHFR, MTR, SAHH, GLDC, SHMT2 and CD166 in a cancer specimen obtained from a subject is to be determined, wherein increased expression level of a biomarker in the cancer specimen as compared to the expression level of the biomarker in a non-cancerous cancer specimen indicates that the subject has a methionine-dependent cancer, and wherein a methionine cycle inhibitor to the subject found to have a methionine-dependent cancer is to be administered to the subject.

In one example, there is provided the use of a methionine cycle inhibitor in the manufacture of a medicament for treating a methionine-dependent cancer, wherein the expression levels of a biomarker selected from the group of MAT2A, MTHFR, MTR, SAHH, GLDC, SHMT2 and CD166 in a cancer specimen obtained from a subject is to be determined, wherein increased expression level of a biomarker in the cancer specimen as compared to the expression level of the biomarker in a non-cancerous cancer specimen indicates that the subject has a methionine-dependent cancer, and wherein a methionine cycle inhibitor to the subject found to have a methionine-dependent cancer is to be administered to the subject.

In one example, there is provided a method of identifying a cancer patient who is responsive to a methionine cycle or MAT2A inhibitor, the method comprising detecting an increased level of expression of a biomarker selected from the group consisting of MAT2A, MTHFR, MTR, SAHH, CD166 and MTAP in a sample obtained from the cancer patient, wherein an increased level of expression of the biomarker in the cancer specimen as compared to the level of expression in a non-cancerous specimen indicates that the cancer is responsive to a methionine cycle or MAT2A inhibitor.

The expression levels of the above markers in a specimen or cell can be assessed relative to that in a reference specimen or cell, e.g. a non-cancerous specimen or cell or a cancer specimen or cell that is not methionine dependent. The specimen could be a tissue sample obtained from a patient. The expression of markers such as MAT2A, MTHFR, MTR, SAHH, CD166 or MTAP can be determined using any standard bioassay procedures known in the art for determination of the level of expression of a gene or protein, such as ELISA, RIA, immunoprecipitation, immunoblotting, immunofluorescence microscopy, RT-PCR, in situ hybridization, cDNA microarray, or the like.

The term "increased expression level" of a biomarker may refer to a 1.2 fold or greater difference between the expression (or mean expression) of a biomarker in a cancer specimen or cell as compared to in a control such as a non-cancerous cell. The term "increased expression level" may also refer to a fold difference of at least 1.5 fold, 2 fold, 3 fold, 4 fold, 5 fold, 6 fold, 7 fold, 8 fold, 9 fold, 10 fold, 11 fold, 12 fold, 13 fold, 14 fold, 15 fold, 16 fold, 17 fold, 18 fold, 19 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 51 fold, 52 fold, 53 fold, 54 fold, 55 fold, 56 fold, 57 fold, 58 fold, 59 fold, 60 fold, 61 fold, 62 fold, 63 fold, 64 fold, 65 fold, 66 fold, 67 fold, 68 fold, 69 fold, 70 fold, 71 fold, 72 fold, 73 fold, 74 fold, 75 fold, 76 fold, 77 fold, 78 fold, 79 fold, 80 fold, 81 fold, 82 fold, 83 fold, 84 fold, 85 fold, 86 fold, 87 fold, 88 fold, 89 fold, 90 fold, 91 fold, 92 fold, 93 fold, 94 fold, 95 fold, 96 fold, 97 fold, 98 fold, 99 fold or 100 fold.

An increased expression level of one or more biomarkers such as MAT2A, MTHFR, MTR, SAHH, CD166 or MTAP in a cancer specimen or cell as compared to a non-cancerous specimen or cell may indicate that a subject has a methionine-dependent cancer. In other embodiments, the subject has a methionine-dependent cancer when there is an increased expression level of one or more biomarkers such as MAT2A, MTHFR, MTR, SAHH, CD166 or MTAP in a cancer specimen or sample as compared to a non-cancerous specimen or sample indicates that a subject has a methionine-dependent cancer. In other embodiments, a subject has a methionine-dependent cancer when a certain percentage of the cells in a cancer sample or specimen has increased expression of the biomarker. This can be, for example, at least 1%, 5%, 10%, 20%, 30%, 40%, 50%, 60%, 70%, 80% or 90% of cells in the cancer sample.

A methionine cycle inhibitor may be an inhibitor of a methionine cycle enzyme's activity or expression. The inhibitor can be an inhibitor capable of specifically reducing enzyme activity, generally by interacting with the protein of the enzyme, or can be an "enzyme expression inhibitor" capable of specifically reducing protein expression. The unmodified term "inhibitor" is used herein to encompass both types of inhibitor. The inhibitor may be a single compound or may include two or more compounds. If the inhibitor includes two or more compounds, at least a subset of the compounds may be present together in the same pharmaceutical preparation or may be present in separate preparations, which may be administered separately to the subject.

In one example, the methionine cycle inhibitor is selected from the group consisting of D9, methotrexate and an anti-folate.

In one example, the methionine cycle inhibitor is an inhibitor of MAT2A, MTHFR, MTR, SAHH, GLDC, SHMT2 or CD166. In one example, the methionine cycle inhibitor is an inhibitor of MAT2A.

In one example, the methionine cycle inhibitor is an inhibitor of SAHH. The inhibitor of SAHH may be D9 or DZNep.

Inhibitors are any agent that modulates an enzyme's function, for example, an agent that interacts with MAT2A to inhibit or enhance MAT2A activity or otherwise affect normal MAT2A function. An enzyme's function can be affected at any level, including transcription, protein expression, protein localization, and cellular or extra-cellular activity.

In the methods of this invention, a MAT2A inhibitor can be any MAT2A inhibitor. In a particular embodiment, the MAT2A inhibitor is an oligonucleotide that represses MAT2A gene expression or product activity by, for example, binding to and inhibiting MAT2A nucleic acid (i.e., DNA or mRNA). In a particular embodiment, the MAT2A inhibitor is an oligonucleotide e.g. an antisense oligonucleotide, shRNA, siRNA, microRNA or an aptamer. In a particular embodiment, the MAT2A inhibitor is a oligonucleotide, for example, as described in WO2004065542 In a particular embodiment, the MAT2A inhibitor is an siRNA, for example, as described in patent application CN 2015-10476981 or in Wang et al, Zhonghua Shiyan Waike Zazhi, 2009, 26(2)-184-186 or Wang et al, Journal of Experimental & Clinical Cancer Research (2008) volume 27. In a particular embodiment, the MAT2A inhibitor is a microRNA oligonucleotide, for example, as described in US patent application publication no. 20150225719 or in Lo et al, PLoS One (2013), 8(9), e75628. In an embodiment, the MAT2A inhibitor is an antibody that binds to MAT2A.

In an example, the MAT2A inhibitor is an inhibitor of MAT2A expression. Exemplary inhibitors of MAT2A expression include nucleic acids or analogs thereof. The inhibitor of MAT2A expression may include anti-MAT2A interfering RNA that binds specifically to an MAT2A gene and/or MAT2A RNA.

In an example, the MAT2A inhibitor is an inhibitor of MAT2A enzyme activity. The MAT2A inhibitor may be selected from the group consisting of FIDAS-5, FIDAS-3, PF-9366 and AG-270.

In one example, the MAT2A inhibitor is FIDAS-5. The FIDAS-5 inhibitor may have the following structure:

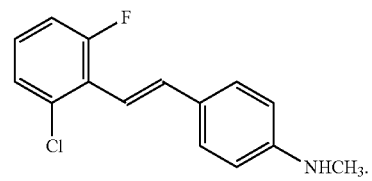 [SMILES: CNc1ccc(/C=C/c2c(F)cccc2Cl)cc1]

In one example, the MAT2A inhibitor is FIDAS-3 with the following structure:

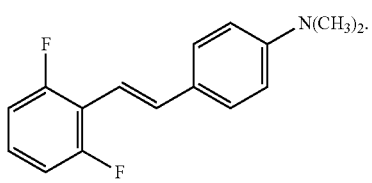 [SMILES: CN(C)c1ccc(/C=C/c2c(F)cccc2F)cc1]

In one example, the MAT2A inhibitor is PF-9366. The PF-9366 inhibitor may have the following structure:

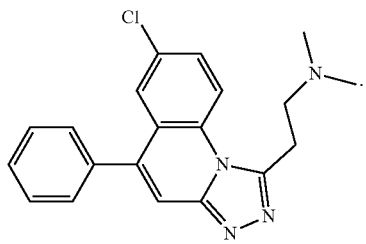 [SMILES: CN(C)CCc1nnc2cc(-c3ccccc3)c3cc(Cl)ccc3n12]

In a particular embodiment, the MAT2A inhibitor is a small molecule compound, e.g. AGI-512 or AGI-673. In an embodiment, the MAT2A inhibitor is a fluorinated N,N-dialkylaminostilbene described in Zhang et al, ACS Chem Biol, 2013, 8(4):796-803. In an embodiment, the MAT2A inhibitor is a 2',6'-dihalostyrylaniline, pyridine or pyrimidine described in Sviripa et al, J Med Chem, 2014, 57:6083-6091. In a particular embodiment the compound is selected from the following compounds:

Aniline Family

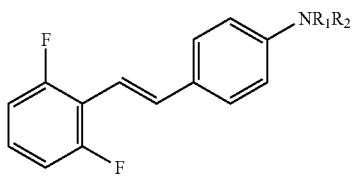

1a $R_1 = R_2 = CH_3$
1b $R_1 = H, R_2 = CH_3$
1c $R_1 = H, R_2 = C_2H_5$

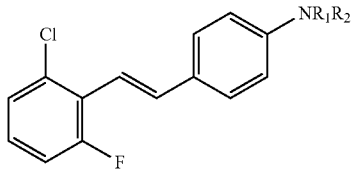

2a $R_1 = R_2 = CH_3$
2b $R_1 = H, R_2 = CH_3$

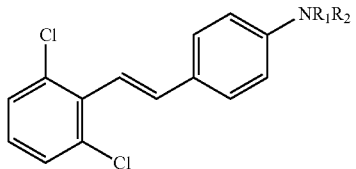

3a $R_1 = R_2 = CH_3$
3b $R_1 = H, R_2 = CH_3$

5-Aminopyridine Family

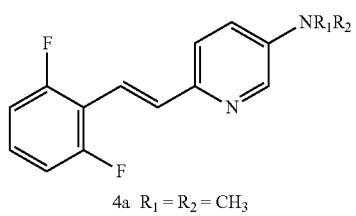

4a $R_1 = R_2 = CH_3$

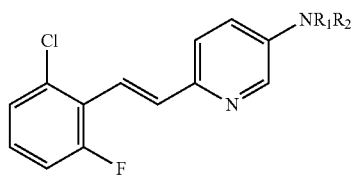

5a $R_1 = R_2 = CH_3$

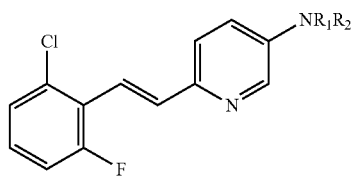

6a $R_1 = R_2 = CH_3$

2-Aminopyridine Family

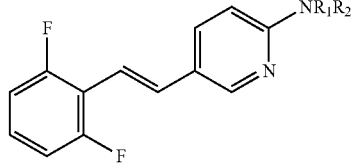

7a $R_1 = R_2 = CH_3$
7b $R_1 = H, R_2 = CH_3$
7c $R_1 = H, R_2 = C_2H_5$

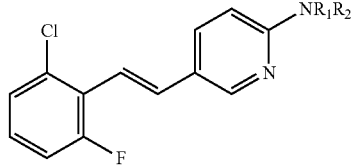

8a $R_1 = R_2 = CH_3$
8b $R_1 = H, R_2 = CH_3$

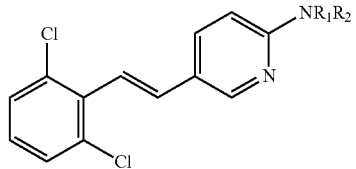

9a $R_1 = R_2 = CH_3$
9b $R_1 = H, R_2 = CH_3$

2-Aminopyrimidine Family

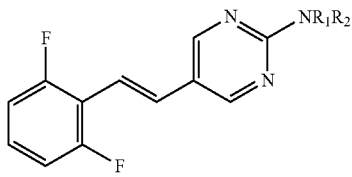

10a R$_1$ = R$_2$ = CH$_3$
10b R$_1$ = H, R$_2$ = CH$_3$
10c R$_1$ = H, R$_2$ = C$_2$H$_5$

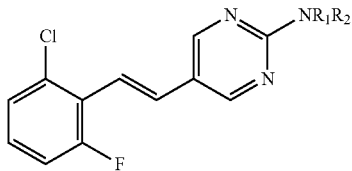

11a R$_1$ = R$_2$ = CH$_3$
11b R$_1$ = H, R$_2$ = CH$_3$

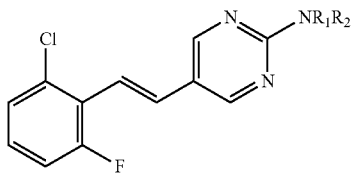

12a R$_1$ = R$_2$ = CH$_3$
12b R$_1$ = H, R$_2$ = CH$_3$

In another embodiment, the MAT2A inhibitor is a compound disclosed in WO2012103457. In an embodiment, the MAT2A inhibitor is a compound of the formula:

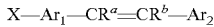

X—Ar$_1$—CR$^a$=CR$^b$—Ar$_2$ where R$^a$ and R$^b$ are independently H, alkyl, halo, alkoxy, cyano; X represents at least one halogen, e.g., a fluorine, chlorine, bromine, or iodine substituent, on Ar$_1$, each of Ar$_1$ and Ar$_2$ are aryl, e.g., phenyl, naphthyl, and heteroaryl, e.g., pyridyl, pyrolidyl, piperidyl, pyrimidyl, indolyl, thienyl, which can be further substituted with halo, amino, alkylamino, dialkylamino, arylalkylamino, N-oxides of dialkylamino, trialkylammonium, mercapto, alkylthio, alkanoyl, nitro, nitrosyl, cyano, alkoxy, alkenyloxy, aryl, heteroaryl, sulfonyl, sulfonamide, CONR$_{11}$R$_{12}$, NR$_{11}$CO(R$_{11}$), NR$_{11}$COO(R$_{13}$), NR$_{11}$CONR$_{12}$R$_n$ where R$_n$, R$_{12}$, R$_{13}$ are independently, H, alkyl, aryl, heteroaryl or a fluorine; provided that Ar$_2$ contains at least one nitrogen atom in the aryl ring or at least one nitrogen substituent on the aryl ring; e.g., an NR$^c$R$^d$Z substituent on Ar$_2$ where R$^c$ is H, alkyl, alkoxy, aryl, heteroaryl, R$^d$ is an alkyl group, Z is a an unshared pair of electrons, H, alkyl, oxygen.

In another embodiment, the MAT2A inhibitor is a compound of formula:

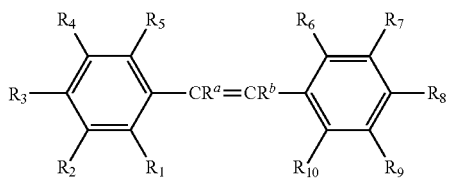

where R$^a$ and R$^b$ are as defined above, R$_1$ to R$_{10}$ are independently H, halo, amino, alkylamino, dialkylamino, N-oxides of dialkylamino, arylalkylamino, dialkyloxyamino, trialkylammonium, mercapto, alkylthio, alkanoyl, nitro, nitrosyl, cyano, alkoxy, alkenyloxy, aryl, heteroaryl, sulfonyl, sulfonamide, CONR$_{11}$R$_{12}$, NR$_{11}$CO(R$_{13}$), NR$_{11}$COO(R$_{13}$), NR$_{11}$CONR$_{12}$R$_{13}$ where R$_{11}$, R$_{12}$, R$_{13}$, are independently, H, alkyl, aryl, heteroaryl or a fluorine; provided at least one of R$_1$ to R$_5$ is a halogen, e.g. a fluorine and/or chlorine; and at least one of R$_6$ to R$_{10}$ is a nitrogen containing substituent, e.g., an NR$^c$R$^d$Z substituent where R$^c$ is H, alkyl, e.g., a lower alkyl, alkoxy, aryl, heteroaryl, R$^d$ is an alkyl group, Z is a an unshared pair of electrons, H, alkyl, oxygen, or a pharmaceutically acceptable salt thereof, or a biotinylated derivative thereof.

In another embodiment, the MAT2A inhibitor is a compound of formula:

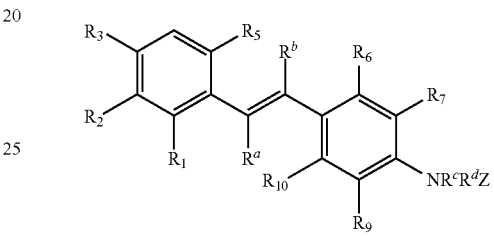

where R$_1$, R$_2$, R$_3$, R$_5$, R$_6$, R$_7$, R$_9$, R$_{10}$, R$^a$, R$^b$ and NR$^c$R$^d$Z are the same as defined above, or pharmaceutically acceptable salts thereof, or a biotinylated derivative thereof. In one embodiment, R$^a$, R$^b$ are both H, one or more of R$_1$, R$_2$, R$_3$, or R$_5$, are fluorine or chlorine and R$^c$ is H or lower alkyl, such as a methyl, ethyl, propyl group, and R$^d$ is a lower alkyl, such as a methyl, ethyl, propyl group.

In an embodiment, the MAT2A inhibitor is selected from the group consisting of: (E)-4-(2-Fluorostyryl)-N,N-dimethylaniline; (E)-4-(3-Fluorostyryl)-N,N-dimethylaniline; (E)-4-(4-Fluorostyryl)-N,N-dimethylaniline; (E)-4-(2-Fluorostyryl)-N,N-diethylaniline; (E)-4-(2-Fluorostyryl)-N,N-diphenylaniline; (E)-1-(4-(2-Fluorostyiyl)phenyl)-4-methylpiperazine; (E)-4-(2-Fluorostyryl)-N,N-dimethylnaphthalen-1-amine; (E)-2-(4-(2-Fluorostyryl)phenyl)-1-methyl-1H-imidazole; (E)-4-(2,3-Difluorostyryl)-N,N-dimethylaniline; (E)-4-(2,4-Difluorostyryl)-N,N-dimethylaniline; (E)-4-(2,5-Difiuorostyiyl)-N,N-dimethylaniline; (E)-4-2-(2,6-Difluorostyryl)-N,N-dimethylaniline; (E)-3-(2,6-Difluorostryl)-N,N-dimethylaniline; (E)-4-(2,6-Difluorostyryl)-N,N-dimethylaniline; (E)-4-(2,6-Difluorostyryl)-N,N-diethylaniline; (E)-4-(3,4-Difluorostyryl)-N,N-dimethylanine; (E)-4-(3,5-Difluorostyryl)-N, N-dimethylaniline; (E)-N,N-Dimethyl-4-(2,3,6-trifluorostyryl)aniline; (E)-N,N-Dimethyl-4-(2,4,6-trifluorostyiyl)aniline; (E)-4-(2<hloro-6-fluorostytyl)-N,N-dimethylaniline; (E)-4-(2,6-dichlorostyryl)-N,N-dimethylaniline; (E)-4-(2,6-Difluorophenelhyl)-N,N-dimethylaniline; and (E)-2-benzamide-4-(2,6-difluoroslyiyl)-N,N-dimethylaniline.

In one example, the methionine cycle inhibitor is administered in combination with an anti-cancer therapy, wherein the anti-cancer therapy is not a methionine cycle inhibitor.

As used herein, the term "anti-cancer agent" may refer to any treatment for cancer including drugs, immunotherapy, targeted therapy, hormonal therapy, chemotherapy, including alkylating agents, antimetabolites, anthracyclines, plant alkaloids, topoisomerase inhibitors, kinase inhibitors and other anti-tumor agents, surgery and radiation therapy.

In an example, the anti-cancer therapy is selected from the group consisting of a chemotherapy, immunotherapy and a radiotherapy. The choice of therapy would depend upon the location and grade of the tumor and the stage of the disease, as well as the general state of the patient.

The chemotherapy may involve administering an anti-proliferative agent such as known anti-proliferative alkylating agents, antitumor antibiotics, antimetabolites, natural alkaloids and inhibitors of protein tyrosine kinases and/or serine/threonine kinases. For instance, examples of such agents include:
  (i) alkylating agents, such as cis-platinum(II)-diaminedichloride (platinol or cisplatin); oxaliplatin (Eloxatin or Oxaliplatin Medac); and carboplatin (Paraplatin);
  (ii) antitumor antibiotics, including those selected from the group comprising anthracyclines, such as doxorubicin (Adriamycin, Rubex);
  (iii) antimetabolites, including folic acid analogues such as pyrimidine analogues such as 5-fluorouracil (Fluoruracil, 5-FU), gemcitabine (Gemzar), or histone deacetylase inhibitors (HDI) for instance, Vorinostat (rINN);
  (iv) natural alkaloids, including paclitaxel (Taxol);
  (v) inhibitors of protein tyrosine kinases and/or serine/threonine kinases including Sorafenib (Nexavar), Erlotinib (Tarceva), Dasatanib (BMS-354825 or Sprycel).

In one example, the anti-cancer therapy is a targeted anti-cancer therapy such as one that uses a receptor kinase inhibitor.

Provided herein is a method of reducing the therapeutic resistance of a subject to an anti-cancer therapy, the method comprising the step of administering a methionine cycle inhibitor to the subject.

In one example, there is provided a methionine cycle inhibitor for reducing the therapeutic resistance of a subject to an anti-cancer therapy.

In one example, there is provided the use of a methionine cycle inhibitor in the manufacture of a medicament for reducing the therapeutic resistance of a subject to an anti-cancer therapy.

Provided herein is a method of inhibiting proliferation or eliminating a tumor initiating cell, the method comprising the step of restricting the intake of methionine into the tumor initiating cell for a time and under conditions suitable for inhibiting proliferation or eliminating the tumor initiating cell. The method may be an in vitro, in vivo or ex vivo method.

Provided herein is a method of inhibiting proliferation or eliminating a tumor initiating cell, the method comprising the step of contacting (or treating) the tumor initiating cell with a methionine cycle inhibitor for a time and under conditions suitable for inhibiting proliferation or eliminating the tumor initiating cell. The method may be an in vitro, in vivo or ex vivo method.

The term "inhibiting proliferation or eliminating a tumor initiating cell" may refer to the eradication of tumor initiating cells by inhibiting or suppressing growth, division, maturation or viability of tumor initiating cells, and/or causing the death of tumor initiating cells, individually or in aggregate with other tumor initiating cells, by cytotoxicity or the induction of apoptosis. One of skill in the art will appreciate that by definition, "inhibiting proliferation or eliminating a tumor initiating cell" also encompasses the eradication or inhibition of the growth, division, maturation or viability of cancer cells, and/or causing the death of cancer cells, individually or in aggregate with other cancer cells, by cytotoxicity or the induction of apoptosis.

Provided herein is a method of treating a subject having a methionine-dependent cancer, the method comprising the step of:
  a) providing a labeled exogenous methionine to a cancer sample obtained from the subject;
  b) measuring the labeled and unlabeled levels of a metabolite selected from the group consisting of SAM, SAH and homocysteine in the sample;
  c) comparing the levels of the labeled metabolite to the unlabeled metabolite; wherein a high level of labeled metabolite as compared to the unlabeled metabolite indicates that the subject has a methionine-dependent cancer;
  d) administering a methionine cycle inhibitor if the subject is found to have a methionine-dependent cancer.

The term "metabolite" as used herein may refer to any substance produced or used during all the physical and chemical processes within the body that create and use energy, such as: digesting food and nutrients, eliminating waste through urine and faeces, breathing, circulating blood, and regulating temperature. In an example, the "metabolite" is a metabolite that is part of the methionine cycle. The "metabolite" may, for example, be methionine, SAM, SAH or homocysteine.

The term "high" as used herein, refers to a measure that is greater than normal, greater than a standard such as a predetermined measure or a subgroup measure or that is relatively greater than another subgroup measure. A normal measure may be determined according to any method available to one skilled in the art. The term "high" may also refer to a measure that is equal to or greater than a predetermined measure, such as a predetermined cut-off. If a subject is not "high" for a particular marker, it is "low" for that marker. In general, the cut-off used for determining whether a subject is "high" or "low" should be selected such that the division becomes clinically relevant.

The term "treating" as used herein may refer to (1) preventing or delaying the appearance of one or more symptoms of the disorder; (2) inhibiting the development of the disorder or one or more symptoms of the disorder; (3) relieving the disorder, i.e., causing regression of the disorder or at least one or more symptoms of the disorder; and/or (4) causing a decrease in the severity of one or more symptoms of the disorder.

In an example, the labeled exogenous methionine is $^{13}C$ methionine.

In an example, the labeled and unlabeled levels of metabolite are measured by mass spectrometry or liquid chromatography mass spectrometry (LCMS).

Provided herein is a method of treating a subject having a methionine-dependent cancer, the method comprising:
  a) providing labeled homocysteine to a cancer sample obtained from the subject;
  b) measuring the levels of labeled S-adenosyl methionine and unlabeled S-adenosyl methionine in the sample;
  c) comparing the levels of labeled S-adenosyl methionine to unlabeled S-adenosyl methionine; wherein a low level of labeled S-adenosyl methionine as compared to unlabeled S-adenosyl methionine indicates that the cell is dependent on exogenous methionine; and
  d) administering a methionine cycle inhibitor if the subject is found to have a methionine-dependent cancer.

In an example, the labeled homocysteine is deuterated homo-cysteine.

The term "low" as used herein, refers to a measure that is lower than normal, lower than a standard such as a predetermined measure or a subgroup measure or that is relatively lower than another subgroup measure. A normal measure may be determined according to any method available to one skilled in the art. The term "low" may also refer to a measure that is equal to or lower than a predetermined measure, such as a predetermined cutoff.

In an example, there is provided a methionine cycle inhibitor for use in treating cancer, wherein the methionine cycle inhibitor is to be administered to a subject. The cancer may be a metastatic cancer. The cancer may also be a methionine dependent cancer.

In an example, there is provided the use of a methionine cycle inhibitor for the manufacture of a medicament for treating cancer, wherein the medicament is to be administered to a subject.

In an example, there is provided a methionine cycle inhibitor for use in reducing the risk of recurrence of cancer in a subject following an anti-cancer, wherein the methionine cycle inhibitor is to be administered to the subject.

In an example, there is provided the use of a methionine cycle inhibitor for the manufacture of a medicament for reducing the risk of recurrence of cancer in a subject following an anti-cancer therapy, wherein the medicament is to be administered to a subject.

In an example, there is provided a methionine cycle inhibitor for use in treating a subject having a methionine-dependent cancer, wherein
  a) a labeled exogenous methionine is provided to a cancer sample obtained from the subject;
  b) the labeled and unlabeled levels of a metabolite selected from the group consisting of SAM, SAH and homocysteine are measured in the sample;
  c) the levels of the labeled metabolite to the unlabeled metabolite are compared; wherein a high level of labeled metabolite as compared to the unlabeled metabolite indicates that the subject has a methionine-dependent cancer; and
    wherein a methionine cycle inhibitor is to be administered to the subject if the subject is found to have a methionine-dependent cancer.

In an example, there is provided the use of a methionine cycle inhibitor in the manufacture of a medicament for treating a subject having a methionine-dependent cancer, wherein
  a) a labeled exogenous methionine is provided to a cancer sample obtained from the subject;
  b) the labeled and unlabeled levels of a metabolite selected from the group consisting of SAM, SAH and homocysteine are measured in the sample;
  c) the levels of the labeled metabolite to the unlabeled metabolite are compared; wherein a high level of labeled metabolite as compared to the unlabeled metabolite indicates that the subject has a methionine-dependent cancer; and
    wherein the medicament is to be administered to the subject if the subject is found to have a methionine-dependent cancer.

In an example, there is provided a methionine cycle inhibitor for use in treating a subject having a methionine-dependent cancer, wherein
  a) a labeled homocysteine is provided to a cancer sample obtained from the subject;
  b) the levels of labeled S-adenosyl methionine and unlabeled S-adenosyl methionine are measured in the sample;
  c) the levels of labeled S-adenosyl methionine to unlabeled S-adenosyl methionine are compared; wherein a low level of labeled S-adenosyl methionine as compared to unlabeled S-adenosyl methionine indicates that the cell is dependent on exogenous methionine; and
    wherein a methionine cycle inhibitor is to be administered to the subject if the subject is found to have a methionine-dependent cancer.

In an example, there is provided the use of a methionine cycle inhibitor in the manufacture of a medicament for treating a subject having a methionine-dependent cancer, wherein
  a) a labeled homocysteine is provided to a cancer sample obtained from the subject;
  b) the levels of labeled S-adenosyl methionine and unlabeled S-adenosyl methionine are measured in the sample;
  c) the levels of labeled S-adenosyl methionine to unlabeled S-adenosyl methionine are compared; wherein a low level of labeled S-adenosyl methionine as compared to unlabeled S-adenosyl methionine indicates that the cell is dependent on exogenous methionine; and
    wherein the medicament is to be administered to the subject if the subject is found to have a methionine-dependent cancer.

The dosage of the methionine cycle inhibitor or a pharmaceutically acceptable salt, solvate, or prodrug thereof, may be administered to a subject in the range from 0.1 mg/kg to 100 mg/kg. For instance, the dosage amount may be 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, 20.0 mg/kg, 21.0 mg/kg, 22.0 mg/kg, 23.0 mg/kg, 24.0 mg/kg, 25.0 mg/kg, 26.0 mg/kg, 27.0 mg/kg, 28.0 mg/kg, 29.0 mg/kg, 30.0 mg/kg, 31.0 mg/kg, 32.0 mg/kg, 33.0 mg/kg, 34.0 mg/kg, 35.0 mg/kg, 36.0 mg/kg, 37.0 mg/kg, 38.0 mg/kg, 39.0 mg/kg, 40.0 mg/kg, 41.0 mg/kg, 42.0 mg/kg, 43.0 mg/kg, 44.0 mg/kg, 45.0 mg/kg, 46.0 mg/kg, 47.0 mg/kg, 48.0 mg/kg, 49.0 mg/kg, 50.0 mg/kg, 51.0 mg/kg, 52.0 mg/kg, 53.0 mg/kg, 54.0 mg/kg, 55.0 mg/kg, 56.0 mg/kg, 57.0 mg/kg, 58.0 mg/kg, 59.0 mg/kg, 60.0 mg/kg, 61.0 mg/kg, 62.0 mg/kg, 63.0 mg/kg, 64.0 mg/kg, 65.0 mg/kg, 66.0 mg/kg, 67.0 mg/kg, 68.0 mg/kg, 69.0 mg/kg, 70.0 mg/kg, 71.0 mg/kg, 72.0 mg/kg, 73.0 mg/kg, 74.0 mg/kg, 75.0 mg/kg, 76.0 mg/kg, 77.0 mg/kg, 78.0 mg/kg, 79.0 mg/kg, 80.0 mg/kg, 81.0 mg/kg, 82.0 mg/kg, 83.0 mg/kg, 84.0 mg/kg, 85.0 mg/kg, 86.0 mg/kg, 87.0 mg/kg, 88.0 mg/kg, 89.0 mg/kg, 90.0 mg/kg, 91.0 mg/kg, 92.0 mg/kg, 93.0 mg/kg, 94.0 mg/kg, 95.0 mg/kg, 96.0 mg/kg, 97.0 mg/kg, 98.0 mg/kg, or 99.0 mg/kg or an amount in between.

The methionine cycle inhibitor or a pharmaceutically acceptable salt, solvate, or prodrug thereof may be administered as a single or multiple doses.

The methionine cycle inhibitor or a pharmaceutically acceptable salt, solvate, or prodrug thereof may be administered continuously in multiple doses to a subject for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 4 months, 5 months, 6 months, 7 months, 8 months, 9 months, 10 months, 11 months or 12 months or any time period inbetween.

In an example, there is provided a pharmaceutical composition comprising the methionine cycle inhibitor or a pharmaceutically acceptable salt, solvate, or prodrug thereof.

Generally, the dosage of the compound of formula (I), or a pharmaceutically acceptable salt, solvate, or prodrug thereof, in a pharmaceutical composition may be in the range from 10-5,000 mg per subject, and typically will be in the range of 50-2,000 mg per subject, and more typically between 20-200 mg per subject.

Methods for the preparation of pharmaceutical compositions are known in the art, for example as described in Remington's Pharmaceutical Sciences, 18th ed., 1990, Mack Publishing Co., Easton, Pa. and U.S. Pharmacopeia: National Formulary, 1984, Mack Publishing Company, Easton, Pa.

Administration and delivery of the compositions may be for example by the intravenous, intraperitoneal, subcutaneous, intramuscular, oral, or topical route, or by direct injection. The mode and route of administration in most cases will depend on the severity and frequency of the concussive events.

The dosage form, frequency and will depend on the mode and route of administration.

The administration of the methionine cycle inhibitor, or a pharmaceutically acceptable salt, solvate, or prodrug thereof, and other agents may also include the use of one or more pharmaceutically acceptable additives, including pharmaceutically acceptable salts, amino acids, polypeptides, polymers, solvents, buffers, excipients, preservatives and bulking agents, taking into consideration the particular physical, microbiological and chemical characteristics of the agents to be administered.

For example, the methionine cycle inhibitor, or a pharmaceutically acceptable salt, solvate, or prodrug thereof, can be prepared into a variety of pharmaceutically acceptable compositions in the form of, e.g., an aqueous solution, an oily preparation, a fatty emulsion, an emulsion, a lyophilised powder for reconstitution, etc. and can be administered as a sterile and pyrogen free intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, caplets, capsules, granules or powders; liquid preparations such as syrup, emulsions, dispersions or suspensions).

It will be appreciated that any compound that is a prodrug of a compound of methionine cycle inhibitor is also within the scope and spirit of the invention. The term "pro-drug" is used in its broadest sense and encompasses those derivatives that are converted in vivo to the compounds of the invention. Such derivatives would readily occur to those skilled in the art, and include, for example, phosphonic acid derivatives.

Compositions containing the methionine cycle inhibitor, or a pharmaceutically acceptable salt, solvate, or prodrug thereof, may also contain one or more pharmaceutically acceptable preservatives, buffering agents, diluents, stabilisers, chelating agents, viscosity enhancing agents, dispersing agents, pH controllers, or isotonic agents.

Examples of suitable preservatives are benzoic acid esters of para-hydroxybenzoic acid, propylene glycol, phenols, phenylethyl alcohol or benzyl alcohol. Examples of suitable buffers are sodium phosphate salts, citric acid, tartaric acid and the like. Examples of suitable stabilisers are, antioxidants such as alpha-tocopherol acetate, alpha-thioglycerin, sodium metabisulphite, ascorbic acid, acetylcysteine, 8-hydroxyquinoline, chelating agents such as disodium edetate. Examples of suitable viscosity enhancing agents, suspending or dispersing agents are substituted cellulose ethers, substituted cellulose esters, polyvinyl alcohol, polyvinylpyrrolidone, polyethylene glycols, carbomer, polyoxypropylene glycols, sorbitan monooleate, sorbitan sesquioleate, polyoxyethylene hydrogenated castor oil 60.

Examples of suitable pH controllers include hydrochloric acid, sodium hydroxide and the like. Examples of suitable isotonic agents are glucose, D-sorbitol or D-mannitol, sodium chloride.

The administration of the methionine cycle inhibitor, or a pharmaceutically acceptable salt, solvate, or prodrug thereof, in the various embodiments of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, glidant, anti-adherent, binder, flavorant or sweetener, taking into account the physical, chemical and microbiological properties of the agents being administered.

For these purposes, the composition may be administered orally, parenterally, by inhalation spray, adsorption, absorption, topically, rectally, nasally, mucosally, transdermally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the compositions will normally be in a unit dosage, sterile, pyrogen free injectable form (solution, suspension or emulsion, which may have been reconstituted prior to use), which is generally isotonic with the blood of the recipient with a pharmaceutically acceptable carrier. Examples of such sterile injectable forms are sterile injectable aqueous or oleaginous suspensions. These suspensions may be formulated according to techniques known in the art using suitable vehicles, dispersing or wetting agents and suspending agents. The sterile injectable forms may also be sterile injectable solutions or suspensions in non-toxic parenterally acceptable diluents or solvents, for example, as solutions in 1,3-butanediol. Among the pharmaceutically acceptable vehicles and solvents that may be employed are water, ethanol, glycerol, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

In addition, the compositions may be in a form to be reconstituted prior to administration. Examples include lyophilisation, spray drying and the like to produce a suitable solid form for reconstitution with a pharmaceutically acceptable solvent prior to administration.

Compositions may include one or more buffers, bulking agents, isotonic agents and cryoprotectants and lyoprotectants. Examples of excipients include, phosphate salts, citric acid, non-reducing such as sucrose or trehalose, polyhydroxy alcohols, amino acids, methylamines, and lyotropic salts which are usually used instead of reducing sugars such as maltose or lactose.

When administered orally, the methionine cycle inhibitor, or a pharmaceutically acceptable salt, solvate, or prodrug thereof, will usually be formulated into unit dosage forms such as tablets, caplets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include excipients such as lactose, dextrose, sucrose, sorbitol, mannitol, starches, gum acacia, calcium phosphate, mineral oil, cocoa butter, oil of theobroma, alginates, tragacanth, gelatin, syrup, substituted cellulose ethers, polyoxyethylene sorbitan monolaurate, methyl hydroxybenzoate, propyl hydroxybenzoate, talc, magnesium stearate, and the like.

A tablet may be made by compressing or molding the agent optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the compound of a methionine cycle inhibitor, or a pharmaceutically acceptable salt, solvate, or prodrug thereof, may also utilize controlled release technology.

The methionine cycle inhibitor, or a pharmaceutically acceptable salt, solvate, or prodrug thereof, may also be administered as a sustained-release pharmaceutical composition. To further increase the sustained release effect, the agent may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof, carboxymethylcellulose sodium hydroxypropylcellulose ether, collagen polyethylene glycol polyethylene oxide, hydroxypropylmethylcellulosemethylcellulose, polyvinyl alcohol, polyvinylpyrrolidone.

Alternatively, the compound of methionine cycle inhibitor, or a pharmaceutically acceptable salt, solvate, or prodrug thereof, may be incorporated into a hydrophobic polymer matrix for controlled release over a period of days. The agent may then be moulded into a solid implant, or externally applied patch, suitable for providing efficacious concentrations of the agents over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers, which may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time-release characteristics and release kinetics. The agent may then be moulded into a solid implant suitable for providing efficacious concentrations of the agents over a prolonged period of time without the need for frequent re-dosing. The agent can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

For topical administration, the methionine cycle inhibitor, or a pharmaceutically acceptable salt, solvate, or prodrug thereof, may be in the form of a solution, spray, lotion, cream (for example a non-ionic cream), gel, paste or ointment. Alternatively, the composition may be delivered via a liposome, nanosome, rivosome, or nutri-diffuser vehicle.

It will be appreciated that other forms of administration of agents are also contemplated, including the use of a nucleic acid encoding a polypeptide for delivering of such agents.

In an example, there is provided a method for determining if a subject has a methionine-dependent cancer, the method comprising the step of: a) determining the expression levels of a biomarker selected from the group of MAT2A, MTHFR, MTR, SAHH, GLDC, SHMT2 and CD166 in a cancer specimen obtained from a subject, wherein an increased expression level of a biomarker in the cancer specimen as compared to the expression level of the biomarker in a non-cancerous cancer specimen indicates that the subject has a methionine-dependent cancer.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

As used in the subject specification, the singular forms "a", "an" and "the" include plural aspects unless the context clearly dictates otherwise. Thus, for example, reference to "a method" includes a single method, as well as two or more methods; reference to "an agent" includes a single agent, as well as two or more agents; reference to "the disclosure" includes a single and multiple aspects taught by the disclosure; and so forth. Aspects taught and enabled herein are encompassed by the term "invention". Any variants and derivatives contemplated herein are encompassed by embodiments of the invention.

EXAMPLES

Aspects disclosed herein are further described by the following non-limiting Examples. Materials and Methods employed are described below.

Materials and Methods

Tissue Culture

Two tumor sphere (TS) lines independently derived from two patients, and TS GLDC KD lines were maintained in DMEM/F12 (US Biomedical) supplemented with 4 mg/ml Bovine Serum Albumin (Sigma), Non-essential amino acids, sodium pyruvate (Life Technologies), 20 ng/ml Epidermal Growth Factor, 4 ng/ml bovine Fibroblast Growth Factor and Insulin—Transferrin Selenium (Sigma). TS-derived adherent (Adh) and NIH 3T3 lines were maintained in the same media as above without EGF, bFGF, ITS and BSA, but instead supplemented with 10% fetal bovine serum. Glutamine, methionine, serine-glycine, leucine, tryptophan and threonine starvation media were generated from DMEM/F12 powder (US Biomedical) lacking the corresponding metabolites. Sodium formate and 5-Methyl-THF disodium salt was purchased from Santa Cruz Biotechnology.

Inhibitors

Cis-platinum (cis-Diammineplatinum(II) dichloride) and MG132 (10 μM final concentration) was purchased from Sigma, FIDAS-5 (final concentration of 10 μM in culture medium) from Merck Millipore and D9 (final concentration of 500 nM in culture medium).

Immunohistochemistry Analysis

The NSCLC tissue tumor microarray (n=47) comprising of paired formalin-fixed paraffin-embedded patient normal and tumor samples at 4 μm thickness were constructed and IHC was performed by Singhealth Advanced Molecular Pathology Laboratory at Singapore General Hospital using a Bond Leica Machine, using Bond Epitope solution 1. The staged tissue tumor microarray (LUM 961 and LUC1021) comprising of formalin fixed paraffin-embedded NSCLC primary and metastatic tumors was purchased from Pantomics. Anti-MTHFR (ab125707) from Abcam and Anti-MAT2A (HPA043028) from Sigma was used for both IHC analyses. IHC of the staged tissue microarray sections was performed using the VECTASTAIN ABC kits (Vector Labs). Samples were subsequently scored by visual assessment as "0/+1", "+2" or "+3", according to the staining intensities MAT2A and MTHFR.

Immunofluorescence Analyses

Formalin-fixed paraffin-embedded NSCLC samples were obtained and cut into 4 μm sections. Sections were deparaffinized and antigen-retrieval was carried out in citrate buffer in the presence of 0.5% Tween 20. Sections were further permeabilized in 0.2% Triton X100 and then quenched with TruBlack (Gold Biotechnology). Sections were then incubated with Anti-MAT2A (GTX50027) from Genetex and Anti-CD166 (HPA010926) from Sigma. Alexa-Fluor 594 Goat anti-Mouse (A11005) and Alexa-Fluor 647 Donkey anti-Rabbit (A21245) from ThermoFisher was used as secondary antibodies. Images were visualized and captured using the Zeiss Observer D1 epifluorescence microscope.

Tumor Implantation and Collection $5 \times 10^5$ single cells were mixed in a 1:1 mixture of serum free DMEM/F12 and Matrigel (BD) and injected subcutaneously into the flanks of 4-6 week old male and female NOD.Cg-Prkdc$^{scid}$ Il2rg$^{tm1wjl}$ SzJ (Jackson Laboratories). About 6 weeks later, or when tumor sizes exceed 2 cm in length, mice were sacrificed and tumors harvested for analysis. All animal experiments were approved by the Agency for Science Technology and Research Singapore—Biological Resource Centre. Mice were randomized by sex.

Orthotopic Tumor Implantation.

GFP expressing $1.5 \times 10^6$ single TS cells (transduced with PLL3.7 vector) with suspended in tumor sphere media and injected intravenously through tail-vein into 4-6 week old male and female NOD.Cg-Prkdc$^{scid}$ Il2rg$^{tm1wjl}$ SWJ (Jackson Laboratories) mice. Mice were continuously monitored and then sacrificed at 5 weeks post injection. Lungs were harvested, fixed in 4% paraformaldehyde and embedded in paraffin for subsequent analysis. Anti-GFP (ab13970) antibody from Abcam and Alexa-Fluor Goat 488 anti-Chicken antibody (A-11039; ThermoFisher) was used to visualize and quantify GFP-positive lesions using immunofluorescence protocol outlined above. Mice were randomized by sex.

Cell Proliferation Assays

Cells were seeded into 96-well plates at a density of 2,000 cells/well for TS cells and 500 cells/well for Adh cells. The relative number of viable cells was determined by the quantification of ATP using the CellTiter-Glo Luminescent Cell Viability Assay (Promega) system.

ATP Analyses

Cells were seeded into 96-well plates at a density of 1,000 cells/well at 10 replicate wells per condition. Cells were then left to equilibrate at 37° C. for 3 h. ATP was then quantified using the CellTiter-GLo reagent (Promega). 5 biological replicates were used.

Soft Agar Colony Formation 2.5 ml lower layer of 0.7% agar in complete DMEM/F12 with 10% fetal bovine serum was placed in 3 wells of a 6 well dish, and permitted to solidify. $2 \times 10^4$ Cells (for 3 wells) were then suspended in a 2 ml layer of 0.35% agar in complete DMEM/F12 with 10% fetal bovine serum and layered on top of the bottom layer. Colonies were stained with crystal violet and counted after approximately 2 months.

Apoptosis Assay $10^6$ cells were stained with FITC Annexin V and PI, and analysed for apoptosis by flow cytometry using an LSRII Cell Analyzer (BD) according to manufacturer's instructions.

Cell Cycle Analysis

Cell cycle analysis was performed using the BID Pharmingen BrdU FITC Flow kit according to manufacturer's instructions.

Metabolomic Analyses

The following reagents and materials were purchased from the indicated sources.

Optima grade methanol: Fisher Scientific (Loughborough, UK); de-ionized water (18.2 mΩ): Sartorius (Gottingen, Germany); Tricine salt, sodium chloride: SigmaAldrich, (St Louis, MO); Acetonitrile, chloroform, formic acid: Merck (Whitehouse Station, NJ); Isotopic labeled Methionine $^{13}C_5$ $^{15}N$ was purchased from Sigma; Homocysteine $^2D_4$ was purchased from Cambridge Isotope Laboratories.

Sample Preparation of Cell Lysate for Metabolomic Analyses

For suspension cell culture, 10 million cells per sample were obtained and quenched with 4 volumes of ice-cold 150 mM sodium chloride solution. The cell pellets were collected by centrifugation of the quenched samples at 3000 g for 5 min at 4° C. and the supernatant was aspirated and discarded. For adherent cell culture, the media was gently aspirated and the cells on the surfaces of the well plates were gently washed with ice-cold 150 mM sodium chloride solution thrice. Ice-cold sodium chloride was added to the plate and a cell scraper was used to release adherent cells from the plate surface. The cell pellets were collected as described earlier and kept on ice. For pulse-chase analysis, cells that were starved with methionine for 16 h in methionine-free media were given a single treatment of labeled methionine ($^{13}C_5$, $^{15}N$) or labelled homocysteine ($^2D_4$). The cells were either lysed immediately as described previously or chased in the incubating media at various time points.

The cell pellets were extracted using a two-phase liquid-liquid extraction protocol based on the modified method of Bligh and Dyer[76]. Briefly, methanol, chloroform and 3.8 mM tricine solution (approx. 1:1:0.5 v/v) was used to separate polar metabolites (aqueous fraction) from lipid species (organic fraction). Polar metabolites in the aqueous fraction comprising of methanol and water were collected in 2 mL Eppendorf tubes. Extracts were stored at −80° C. prior to UPLC-MS analysis. The samples were dried under vacuum pressure at 4° C. using a CentriVap centrifugal vacuum concentrator (Labconco, MO, USA) and reconstituted in 5% methanol-water solution (v/v) prior to LC/MS analysis.

UPLC-MS Analysis

Untargeted LC/MS analysis of the polar metabolites was performed using an ultra-high performance liquid chromatography (UPLC) system (ACQUITY, Waters Corp, Milford, MA) interfaced with a mass spectrometer (LTQ-Orbitrap; Thermo Scientific, Bremen, Germany). Electrospray ionization (ESI) in the MS was conducted in both positive and negative modes in full scan with a mass range of 50 to 1000 m/z at a resolution of 15,000. Sheath and auxiliary gas flow was set at 40 and 15 (arbitrary units) respectively, with a capillary temperature of 400° C. The ESI source and capillary voltages were 4.5 kV and 40V respectively for positive ESI mode, and 2.8 kV and −15V respectively for negative ESI mode. Mass calibration was performed using standard LTQ-Orbitrap calibration solution (Thermo Scientific) prior to sample injection. A pooled quality control (QC) mixture comprised of equal aliquots of all samples was run at regular intervals throughout each analytical batch. The samples were randomized for each analytical batch and triplicate injections were performed for each sample.

Targeted LC/MS/MS analysis was performed using a UPLC system (ACQUITY, Waters Corp)) interfaced to a triple quadrupole mass spectrometer (Xevo TQ-S, Waters Corp). Multiple reaction monitoring (MRM) experiments were performed in both ESI positive and negative mode using elution gradient as described in Table 1. The compound-dependent MS parameters for the analytes are shown in Table 2. The source temperature and desolvation temperature were set at 150° C. and 500° C. respectively. The cone gas flow was 150 L/h and desolvation gas flows were 700 L/h (ESI+) and 300 L/h (ESI−). The capillary voltage was 2.90 kV for the positive ESI mode and 1.0 kV for the negative ESI mode.

TABLE 1

Elution condition for LC/MS analysis

| | Time (min) | Solvent A (%) | Solvent B1 (%) | Solvent B2 (%) | Flow rate (mL/min) |
|---|---|---|---|---|---|
| Sample analysis | Initial | 99.9 | 0.1 | | 0.400 |
| | 0.50 | 99.9 | 0.1 | | |
| | 8.50 | 50.0 | 50.0 | | |
| | 8.51 | 2.0 | 98.0 | | |
| | 11.50 | 2.0 | 98.0 | | |
| Column wash | 12.50 | 2.0 | | 98.0 | 0.500 |
| | 15.50 | 2.0 | | 98.0 | |
| Column equilibration | 16.50 | 99.9 | 0.1 | | 0.400 |
| | 18.00 | 99.9 | 0.1 | | |

Solvent A: 0.1% formic acid in water, Solvent B1: 0.1% formic acid in methanol and Solvent B2: 0.1% formic acid in acetonitrile.

TABLE 2

Optimized compound-dependent. MS parameters using Xevo TQ-S mass spectrometer.

| Analyte | Parent ion mass (m/z) | Daughter ion mass (m/z) | Dwell time (s) | Cone voltage (V) | Collision Energy (V) | ESI Mode |
|---|---|---|---|---|---|---|
| Methionine | 150 | 105 | 0.025 | 40 | 15 | Pos |
| Methionine ($^{13}C_5{}^{15}N_1$) | 156 | 109 | 0.025 | 40 | 15 | Pos |
| *Regenerated methionine from Homocysteine ($^{13}C_4{}^{15}N_1$) | 155 | 108 | 0.025 | 40 | 15 | Pos |
| S-adenosylmethionine | 399 | 136 | 0.025 | 62 | 47 | Pos |
| *SAM ($^{13}C_5{}^{15}N_1$) | 405 | 136 | 0.025 | 62 | 42 | Pos |
| *Regenerated SAM from Homocysteine ($^{13}C_4{}^{15}N_1$) | 404 | 136 | 0.025 | 62 | 42 | Pos |
| S-adenosylhomocysteine | 385 | 134 | 0.025 | 66 | 33 | Pos |
| *SAH ($^{13}C_5{}^{15}N_1$) | 390 | 139 | 0.025 | 36 | 33 | Pos |
| Homocysteine | 136 | 90 | 0.025 | 15 | 16 | Pos |
| Deuterium Labelled Homocysteine ($^2D_4$) | 140 | 94 | 0.025 | 15 | 16 | Pos |
| *Methionine ($^2D_4$) | 154 | 108 | 0.025 | 40 | 15 | Pos |
| *SAM ($^2D_4$) | 404 | 136 | 0.025 | 62 | 42 | Pos |
| *SAH ($^2D_4$) | 389 | 137 | 0.025 | 66 | 33 | Pos |
| Hippuric acid (Internal Standard) | 185 | 110 | 0.025 | 30 | 16 | Pos |

The MRM transitions and the MS parameters were optimized using either analytical grade standards or intracellularly synthesized metabolites (*).

All chromatographic separations were performed using an ACQUITY UPLC HSS T3 1.7 μm 50×2.1 mm i.d. column (Waters Corp). The column and autosampler temperatures were maintained at 30° C. and 4° C. respectively. The elution condition is indicated in Table 1. The injection volume was 4 μL.

Data Pre-Processing and Metabolite Identification

For untargeted LC/MS, the raw UPLC-MS data was pre-processed and analyzed using an in-house software which incorporated the XCMS peak finding algorithm. The pooled QC mixture was used for signal correction between and within each batch analysis. Samples were normalized based on their cell counts. The identities of marker metabolites were verified by comparison of their retention time and mass spectra with commercially available standards.

For targeted LC/MS analysis, the chromatographic peak integration was performed using Targetlynx software (Waters Corp). In addition, for the $^{13}C$-labeled methionine pulse-chase experiments, the atomic percent excess (APE) for each species was calculated and natural abundance corrected from an isotopomer matrix accounting for the presence of natural abundance carbons distributed throughout each possible parent/daughter ion combination (Table 3).

TABLE 3

Metabolite species in $^{13}C$-labeled methionine pulse-chain experiment and the corresponding MRM transition pairs (Q1/Q3)

| Metabolites | | Q1/Q3 |
|---|---|---|
| Methionine | Endogenous methionine | 150/105 |
| | Methionine ($^{13}C_5{}^{15}N_1$) | 156/109 |
| | *Regenerated methionine from Homocysteine ($^{13}C_4{}^{15}N_1$) | 155/108 |

TABLE 3-continued

Metabolite species in $^{13}$C-labeled methionine pulse-chain experiment and the corresponding MRM transition pairs (Q1/Q3)

| Metabolites | | Q1/Q3 |
|---|---|---|
| S-adenosylmethionine | Endogenous S-adenosylmethionine | 399/136 |
| | *SAM ($^{13}C_5^{15}N_1$) | 405/136 |
| | Regenerated SAM from Homocysteine ($^{13}C_4^{15}N_1$) | 404/136 |
| S-adenosylhomocysteine | Endogenous S-adenosylhomocysteine | 385/134 |
| | *SAH ($^{13}C_5^{15}N_1$) | 390/139 |

RNA Interference and Lentiviral Transduction

Short hairpin RNAs (shRNA) were cloned into the lentiviral plasmid pLKO.1 (Addgene). 2 shRNAs each was used against GLDC, MAT2A and MTHFR. Tumor sphere lines were infected with plKO.1 lentivirus and selected in 2 µg/ml puromycin for 7 days.
Sense sequences are as follows:

```
Control Luciferase shRNA:
                                        (SEQ ID NO: 1)
5'-CCGGCGCTGAGTACTTCGAAATGTCCTCGAGGACATTTCGAAGTACTCAGCGTTTTTG-3';

SHMT2sh1:
                                        (SEQ ID NO: 2)
5'-CCGGCCGGAGAGTTGTGGACTTTATCTCGAGATAAAGTCCACAACTCTCCGGTTTTTG-3';

SHMT2sh2:
                                        (SEQ ID NO: 3)
5'-CCGGGTCTGACGTCAAGCGGATATCCTCGAGGATATCCGCTTGACGTCAGACTTTTTG-3';

GLDCsh1:
                                        (SEQ ID NO: 4)
5'-CCGGCCTGCCAACATCCGTTTGAAACTCGAGTTTCAAACGGATCTTTGGCAGGTTTTTG-3';

GLDCsh2:
                                        (SEQ ID NO: 5)
5'-CCGGCCACGGAAACTGCGATATTAACTCGAGTTAATATCGCAGTTTCCGTGGTTTTTG-3';

MAT2Ash1:
                                        (SEQ ID NO: 6)
5'-CCGGAGCAGTTGTGCCTGCGAAATACTCGAGTATTTCGCAGGCACAACTGCTTTTTG-3';

MAT2Ash2:
                                        (SEQ ID NO: 7)
5'-CCGGCCAGATAAGATTTGTGACCAACTCGAGTTGGTCACAAATCTTATCTGGTTTTTG-3';

MTHFRsh1:
                                        (SEQ ID NO: 8)
5'-CCGGATATTAGACAGGACCATTATGCTCGAGCATAATGGTCCTGTCTAATATTTTTTG-3';

MTHFRsh2:
                                        (SEQ ID NO: 9)
5'-CCGGAGAGTATCCAAGACGACATTCCTCGAGGAATGTCGTCTTGGATACTCTTTTTT-3';

mat2ash1:
                                        (SEQ ID NO: 10)
5'-CCGGTTTGGAGGACGTACGTAATAACTCGAGTTATTACGTACGTCCTCCAAATTTTTG-3';

mat2ash2:
                                        (SEQ ID NO: 11)
5'-CCGGACCGGAATGAGGAAGATATTGCTCGAGCAATATCTTCCTCATTCCGGTTTTTG-3'.
```

Immunoblotting $1.5 \times 10^6$ cells were lysed in Llaemli-SDS buffer and then sonicated. Total protein concentration was measured by Bradford assay. Total cell lysates were separated by SDS-PAGE and transferred onto nitrocellulose, followed by blocking in 5% (v/v) milk in Tris-buffered saline in Tween 20, probing with the indicated antibodies and visualized by chemiluminescence (Roche). Primary antibodies used were anti-β-Actin (sc-47778), anti-GAPDH (sc-32233) from Santa Cruz: anti-GLDC (ab97625), anti-H3 (ab1791), anti-H3 (dimethylK36) (ab9049), anti-MAT2A (ab77471), anti-MTR (ab9209), anti-H3 (trimethylK79) (ab2621), anti-MTHFR (ab125707), anti-MTAP (ab ab55517) from Abcam; anti-H3(trimethyl K4) (39159), anti-H3(trimethyl K27)(39155), anti-H3(trimethylK36)(61101) and anti-H3 (trimethylK9)(39765) from Active Motif; anti-β-catenin (BD610154) from BD Biosciences; anti-SHMT2 (HPA020549) and anti-SAHH (WH0000191M8) from Sigma; anti-Symmetric Di-Methyl Arginine Motif (13222) from CST.

Molecular Cloning

The open reading frame for human MTHFR was first cloned into the lentiviral expression plasmid PLVX-Tight. The modified doxycycline-inducible promoter sequence was then replaced with a constitutive CMV promoter sequence to allow for constitutive expression of MTHFR. The open reading frame for the shRNA-resistant human GLDC was also cloned into the same modified PLVX-CMV construct.

Protein Turnover Experiments $5 \times 10^5$ cells were treated with 20 µg/ml of cycloheximide (Sigma) and harvested for immunoblotting at indicated time points thereafter.

Analysis of α-Ketoglutarate/Succinate Ratios

Analysis of intracellular o-ketoglutarate and succinate levels were performed using the BioVision kits (K677, K649) according to manufacturer's instructions.

Statistical Analysis

Graphpad Prism (Graphpad Software) v 7.0 was used for statistical analyses. No statistical methods were used to predetermine sample size. Statistical analysis in FIGS. 1g and 1h was carried out by using multiple t-test and statistical significance corrected for multiple comparisons using the Holm-Sidak method. Statistical analysis in FIG. 4i and Supplementary FIG. 4h was carried out by using paired Student's two-tailed t-test. Statistical analysis in FIG. 4j and Supplementary FIG. 4i was performed using the Chi-Square test. Statistical analysis in Supplementary FIGS. 2b, 4e, 5g and 5h was carried out by using unpaired Student's two-tailed t-test. $P<0.05$ was considered to be statistically significant. Significance levels are indicated in relevant figure legends. Data was assumed to be normally distributed for all analyses conducted. Variances were not statistically different in any of the data. Data for independent experiments are presented as means±s.d. unless otherwise stated.

Data Availability

The metabolomics datasets generated or analysed during this study are included in this published article in Supplementary Tables 1 and 2. Additional datasets are also available from the corresponding author on reasonable request.

TABLE 4

Figure 1D:
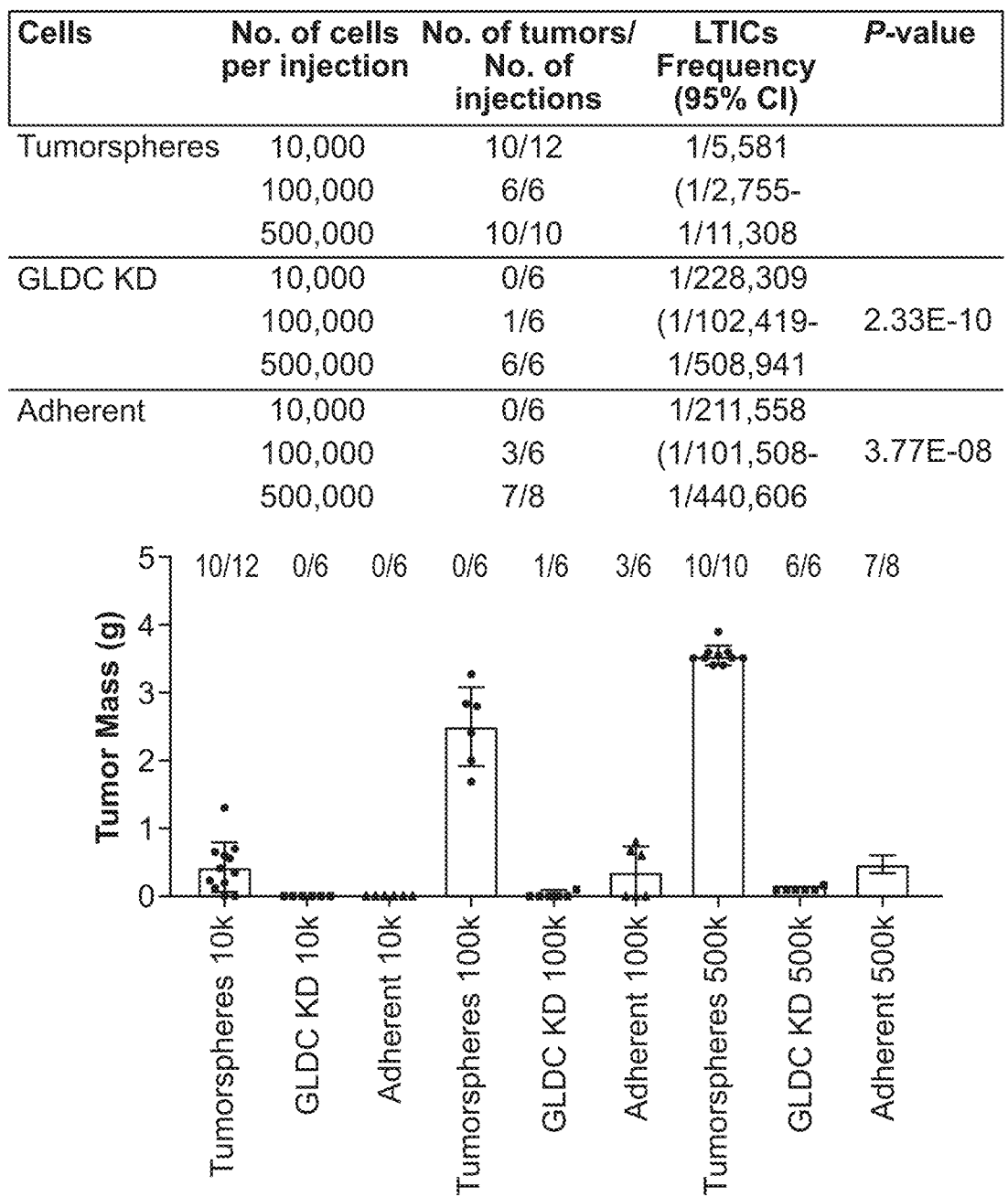
FIG. 1(d) is a graphical representation showing (i) Top—Frequency of tumor initiating cells (TICs) present in TS, GLDC KD and Adh cells. CI: confidence interval. (ii) Bottom: Tumor masses following subcutaneous implantation of cells. Cell type and number are stated at the x-axis. For the injection of 10 k and 100 k cells, tumors were harvested 8 weeks after implantation; tumors from the injection of 500 k cells were harvested 6 weeks after implantation. Error bars denote s.d.; Number of injections indicated in top panel.
Figure 1E:
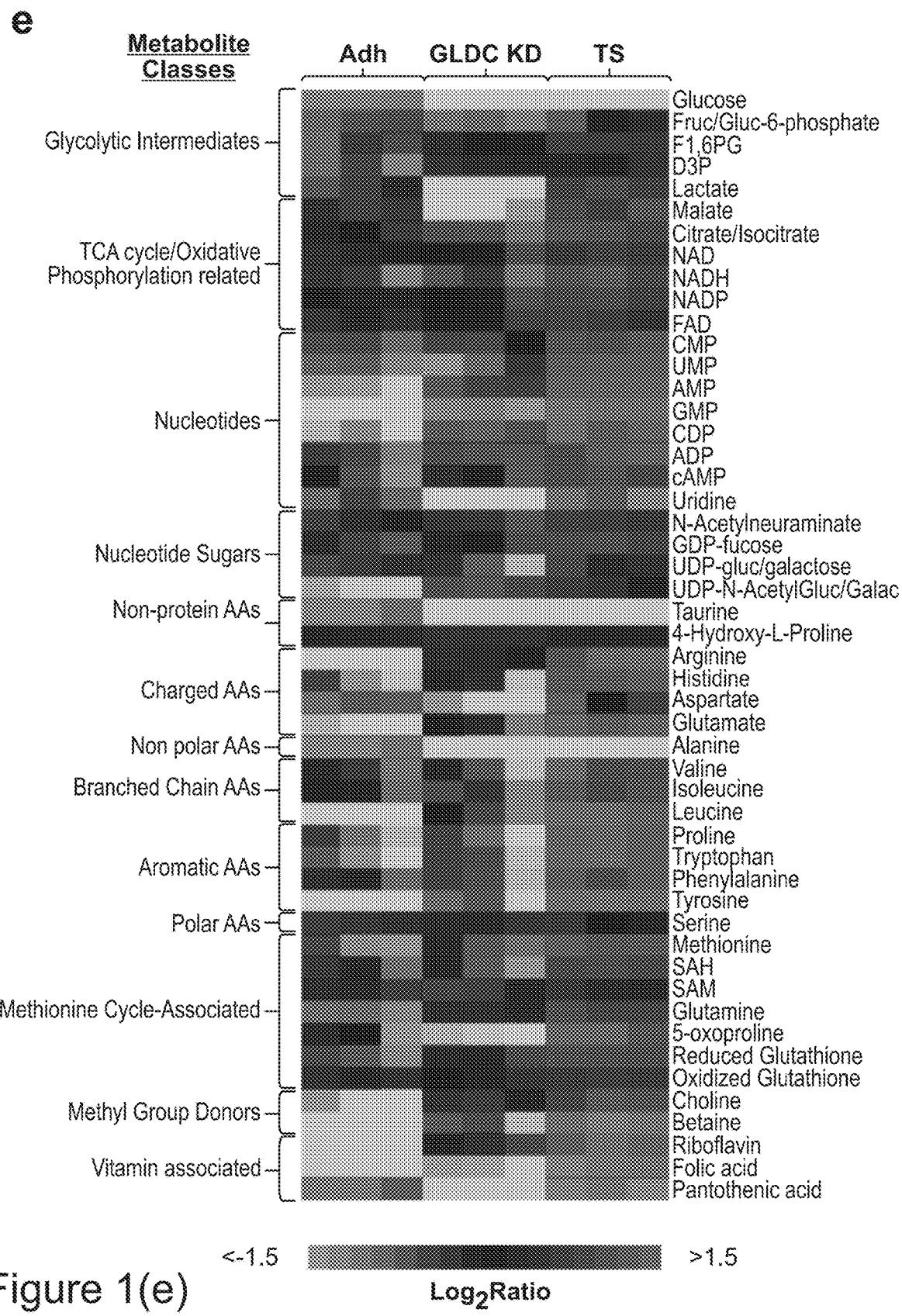
FIG. 1(e) is a graphical representation of the metabolomic comparison of Adh, GLDC KD and TS cells. Three biological replicates are shown as columns for each condition.

Summary of metabolites detected in TS, Adh and GLDC KD cells (see also Fig. 1e)

Total number of features in positive and negative ESI modes: 1409
Metabolites with confirmed identities

| Class/ Function | Metabolite ID | Fold-change with respect to Adh | |
|---|---|---|---|
| | | Avg GLDC KD | Avg TS |
| Glycolysis intermediates | Glucose | 0.072 | 0.005 |
| | G6P/F6P | 0.313 | 0.449 |
| | F1, 6P | 0.689 | 0.530 |
| | GD3P | 0.575 | 0.655 |
| | Lactate | 0.219 | 1.036 |
| TCA cycle intermediates | Malate | 0.285 | 1.224 |
| | Isocitrate/Citrate | 0.714 | 1.832 |
| Nucleotides | CMP | 1.162 | 2.570 |
| | UMP | 1.057 | 3.305 |
| | AMP | 1.653 | 4.701 |
| | GMP | 2.327 | 11.079 |
| | CDP | 1.513 | 4.882 |
| | ADP | 1.007 | 2.723 |
| | cAMP | 1.311 | 2.309 |
| | Guanosine | 0.373 | 2.253 |
| | Uridine | 0.110 | 3.789 |
| | Inosine | 0.319 | 0.686 |
| | Inosine phosphate | 1.903 | 6.261 |
| Sugars/ Nucleotide sugars | N-acetylneuraminate | 0.778 | 1.228 |
| | Glucosamine/Galactosamine | 0.771 | 1.025 |
| | GDP-Fucose | 1.172 | 2.124 |
| | UDP-Glucose/UDP-Galactose | 0.461 | 0.922 |
| | UDP-GlcNAc/UDP-GalNAc | 4.385 | 3.078 |
| Amino acids | Taurine | 0.000 | 0.000 |
| | 4-Hydroxy-L-Proline | 1.129 | 0.987 |
| | Aminobutanoate | 1.821 | 4.047 |
| | Arginine | 12.024 | 23.917 |
| | Histidine | 1.363 | 3.558 |
| | Aspartate | 0.158 | 0.367 |
| | Glutamate | 2.157 | 5.701 |
| | Alanine | 0.093 | 0.367 |
| | Valine | 0.723 | 2.467 |
| | Isoleucine | 0.830 | 2.126 |
| | Leucine | 2.512 | 7.634 |
| | Proline | 0.808 | 3.774 |
| | Tryptophan | 1.230 | 4.662 |
| | Phenylalanine | 0.761 | 2.414 |
| | Tyrosine | 1.885 | 8.315 |
| | Serine | 0.847 | 0.691 |
| Methionine cycle and redox metabolism | Methionine | 1.303 | 3.818 |
| | SAB | 0.668 | 1.650 |
| | SAM | 1.515 | 1.412 |
| | Glutamine | 1.921 | 2.656 |
| | Pyroglutamate | 0.398 | 2.543 |
| | Glutathione (Reduced) | 1.482 | 2.679 |
| | Glutathione (Oxidized) | 0.897 | 1.293 |
| | Cysteine-glutathione disulfide | 27.124 | 0.884 |
| Methyl group donors Co-factors and vitamins | Choline | 3.549 | 4.784 |
| | Betaine | 15.076 | 63.656 |
| | Riboflavin | 17.623 | 38.186 |
| | Folic acid | Absent in Adh | Absent in Adh |
| | Pantothenate | 0.054 | 0.214 |
| | NAD | 0.812 | 1.244 |
| | NADH | 0.809 | 2.051 |
| | NADP | 0.949 | 1.730 |
| | FAD | 0.876 | 1.300 |
| Phospholipid synthesis | CDP-choline | 2.166 | 3.781 |
| | CDP-ethanolamine | 0.509 | 1.441 |
| | Glycerophosphocholine | 2.979 | 3.874 |
| | Glycerophosphoethanolamine | 1.887 | 5.004 |
| *Putative metabolite IDs based on accurate mass matching with HMDB and KEGG databases | 2-Phospho-glycerate/ 3-Phospho-glycerate | 1.037 | 0.455 |
| | 7, 8-Dihydrobiopterin | 0.653 | 1.573 |
| | 10-Formyldihydrofolate | Absent in Adh | Absent in Adh |
| | Adenylosuccinate | 1.001 | 23.944 |
| | Ala-Ala/Methyl-glutamine | 0.013 | 0.238 |
| | Aminoimidazole ribotide | 2.424 | 2.618 |
| | Asp-Gly | 1.106 | 0.963 |
| | Asp-Phe | 5.993 | 7.340 |
| | beta-Asp-Glu | 0.567 | 0.968 |
| | CMP-N-glycoloylneuraminate | 2.71E–06 | 2.61E–06 |
| | cyclic dGMP | 0.891 | 1.170 |
| | Deoxy-ribose phosphate/ Deoxy-xylulose phosphate | 9.328 | 30.968 |
| | Dihydroxy-phenylalanine | Absent in Adh | Absent in Adh |
| | Flavin mononucleotide | 0.792 | 1.488 |
| | Formyldihydrofolate | 14.631 | 52.256 |
| | gamma-Glu-Gln | Absent in Adh | Absent in Adh |
| | Glu-Glu | 86.079 | 349.636 |
| | Glycerophosphoglycerol | 0.243 | 0.902 |
| | Glycerophoinositol | 0.048 | 0.106 |
| | Glycerophosphoric acid | 0.365 | 1.264 |
| | Hornovanillate | 1.124 | 0.989 |
| | Lys-Ala-Ala | 24.109 | 201.054 |
| | Methylhippuric acid | 13.994 | 36.452 |
| | N2-Acetyl-L-aminoadipate | 3.482 | 6.350 |
| | N-Acetylasparagine/ N-Formimino-glutamate | 1.681 | 6.484 |
| | N-Acetylglucosaminate/N-Acetylgalactosaminate/ Biopterin | 1.079 | 0.833 |
| | N-Acetylglucosamine phosphate/ N-Acetylgalactosamine phosphate | 1.620 | 1.641 |
| | N-Acetylglutamine/ Glycyl-hydroxyproline | 3.230 | 8.694 |
| | N-glycoloylneuraminate | 0.001 | 0.000 |
| | N-Methyl-aspartate | 199.239 | 758.484 |
| | Phenylpyruvate | 0.745 | 1.724 |
| | Phosphocholine | 2.750 | 4.261 |
| | Phosphoribosyl-AMP | 0.920 | 2.190 |

TABLE 4-continued

Summary of metabolites detected in TS, Adh and GLDC KD cells (see also Fig. 1e)

Total number of features in positive and negative ESI modes: 1409
Metabolites with confirmed identities

| Class/Function | Metabolite ID | Fold-change with respect to Adh | |
|---|---|---|---|
| | | Avg GLDC KD | Avg TS |
| | Pro-Gly | 0.082 | 0.129 |
| | Propanoyl phosphate/Glycerol cyclic phosphate | 0.245 | 0.988 |
| | Riboflavin cyclic phosphate | 0.877 | 1.204 |
| | S-(Formylmethyl)glutathione | 5.971 | 26.082 |
| | S-Lactoylglutathione | 0.355 | 0.271 |
| | Selenohomocysteine | 0.341 | 0.145 |
| | S-Methyl-thioribose phosphate | 14.109 | 163.343 |
| | Thiamin diphosphate | 0.606 | 0.365 |

Figure 13:
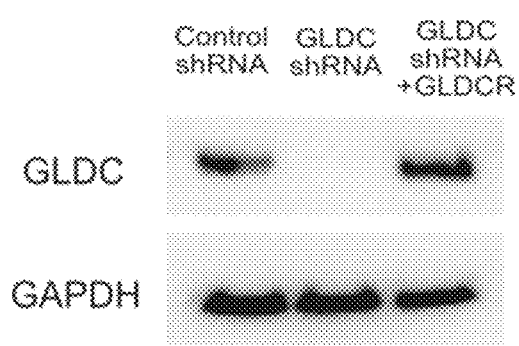
FIG. 13 is a photographic representation of a western blot showing the comparison of GLDC protein abundance in TS, Control Luc shRNA knockdown and GLDC KD Rescue cells normalized to the abundances in Adh cells.

TABLE 5 comparison of metabolite abundances detected in TS, Control Luc shRNA knockdown and GLDC KD Rescue cells normalized to the abundances in Adh cells (see also Fig 13).

| Class/Function | Metabolite ID | Fold-change with respect to Adh | | | p-value with respect to Adh (Welch's t-test) | | |
|---|---|---|---|---|---|---|---|
| | | Avg TS | Ave Luc | Ave Rescue | TS | Luc | Rescue |
| Glycolysis Intermediate | Glucose | 0.65 | 0.61 | 0.63 | 0.003 | <0.001 | 0.023 |
| | G6P/F6P | 0.80 | 1.08 | 1.15 | 0.011 | 0.429 | 0.309 |
| | F1, 6P | 1.60 | 2.14 | 1.72 | 0.010 | <0.010 | 0.029 |
| | GD3P | 0.38 | 0.31 | 0.41 | 0.020 | 0.018 | 0.014 |
| | Lactate | 1.21 | 1.31 | 2.30 | 0.110 | 0.019 | 0.033 |
| TCA Cycle Intermediates | Malate | 1.47 | 1.40 | 1.76 | 0.020 | 0.008 | 0.007 |
| | Isocitrate/Citrate | 2.11 | 2.09 | 2.30 | 0.010 | <0.001 | <0.001 |
| Nucleotides | CMP | 6.13 | 7.85 | 9.87 | <0.001 | <0.001 | 0.010 |
| | UMP | 7.97 | 8.54 | 11.68 | 0.004 | <0.001 | 0.004 |
| | AMP | 7.07 | 10.66 | 13.29 | 0.003 | <0.001 | 0.012 |
| | GMP | 10.53 | 14.07 | 18.56 | 0.008 | 0.004 | 0.027 |
| | CDP | 4.52 | 3.75 | 4.16 | 0.002 | <0.001 | 0.012 |
| | ADP | 2.63 | 2.94 | 3.14 | 0.007 | <0.001 | 0.012 |
| | cAMP | 1.38 | 1.24 | 1.79 | 0.068 | 0.147 | 0.009 |
| | Guanosine | 0.29 | 0.41 | 0.79 | 0.031 | 0.047 | 0.258 |
| | Uridine | 0.27 | 0.48 | 0.56 | 0.085 | 0.147 | 0.193 |
| | Inosine | 0.81 | 1.47 | 4.73 | 0.397 | 0.120 | 0.057 |
| | Inosine phosphate | 2.92 | 1.62 | 2.88 | 0.011 | 0.008 | 0.034 |
| Sugars/Nucleotides sugars | N-acetylneuraminate | 3.25 | 5.11 | 5.18 | 0.010 | 0.002 | 0.024 |
| | Glucosamine | 1.18 | 1.17 | 1.10 | 0.015 | 0.015 | 0.042 |
| | GDP-Fucose | 1.83 | 1.74 | 2.39 | 0.060 | 0.004 | 0.041 |
| | UDP-Glucose/UDP-Galactose | 1.14 | 0.95 | 1.12 | 0.314 | 0.570 | 0.604 |
| | UDP-GlcNAc/UDP-GalNAc | 2.39 | 6.38 | 4.96 | 0.031 | <0.001 | 0.077 |
| Amino Acids | Taurine | 0.02 | 0.03 | 0.03 | 0.002 | 0.002 | 0.002 |
| | 4-Hydroxy-L-Proline | 1.17 | 1.16 | 1.11 | 0.011 | 0.011 | 0.056 |
| | Aminobutanoate | 5.78 | 6.00 | 7.70 | 0.005 | <0.001 | 0.023 |
| | Arginine | 5.05 | 6.75 | 3.45 | <0.001 | <0.001 | 0.004 |
| | Histidine | 10.90 | 10.82 | 13.39 | 0.012 | 0.001 | 0.017 |
| | Aspartate | 1.17 | 1.25 | 1.06 | 0.308 | 0.096 | 0.769 |
| | Glutamic acid | 7.63 | 7.90 | 9.78 | 0.011 | <0.001 | 0.019 |
| | Valine | 3.64 | 4.42 | 4.69 | 0.009 | <0.001 | 0.015 |
| | Isoleucine | 4.39 | 5.63 | 6.15 | 0.009 | <0.001 | 0.011 |
| | Leucine | 5.47 | 7.07 | 7.25 | 0.008 | <0.001 | 0.011 |
| | Proline | 4.25 | 6.56 | 6.10 | 0.002 | <0.001 | 0.024 |
| | Tryptophan | 3.93 | 4.67 | 5.60 | 0.008 | <0.001 | 0.022 |
| | Phenylalanine | 5.15 | 6.30 | 7.09 | 0.007 | <0.001 | 0.017 |
| | Tyrosine | 4.48 | 5.30 | 6.08 | 0.005 | <0.001 | 0.007 |
| | Serine | 3.17 | 4.68 | 4.19 | 0.059 | <0.001 | 0.085 |
| Methionine cycle and redox metabolism | Methionine | 9.32 | 11.50 | 12.27 | 0.007 | <0.001 | 0.021 |
| | SAH | 2.29 | 2.41 | 3.54 | 0.013 | 0.017 | 0.006 |
| | SAM | 2.40 | 1.76 | 2.03 | 0.002 | 0.001 | 0.013 |
| | Glutamine | 38.60 | 49.45 | 46.52 | 0.003 | 0.001 | 0.021 |
| | Pyroglutamic acid | 4.93 | 4.84 | 6.56 | 0.005 | <0.001 | 0.018 |
| | Glutathione (Seduced) | 5.20 | 3.63 | 4.73 | 0.002 | <0.001 | 0.007 |
| | Glutathione (Oxidised) | 3.80 | 2.83 | 3.57 | 0.054 | 0.006 | 0.001 |
| | L-Cysteine-glutathione Disulfide | 3.37 | 3.67 | 3.52 | 0.106 | 0.035 | 0.197 |

TABLE 5-continued comparison of metabolite abundances detected in TS, Control Luc shRNA knockdown and GLDC KD Rescue cells normalized to the abundances in Adh cells (see also Fig 13).

| Class/Function | Metabolite ID | Fold-change with respect to Adh | | | p-value with respect to Adh (Welch's t-test) | | |
|---|---|---|---|---|---|---|---|
| | | Avg TS | Ave Luc | Ave Rescue | TS | Luc | Rescue |
| Methyl Group | Choline | 1.42 | 2.66 | 2.43 | 0.012 | <0.001 | 0.029 |
| Donors | Betaine | 11.13 | 16.39 | 15.34 | 0.003 | <0.001 | 0.012 |
| Co-factors and | Riboflavin | 18.93 | 19.75 | 24.22 | 0.001 | <0.001 | 0.018 |
| vitamins | Folic acid | 57.17 | 58.49 | 78.21 | 0.014 | 0.005 | 0.010 |
| | Pantothenic acid | 1.12 | 1.12 | 1.32 | 0.330 | 0.233 | 0.213 |
| | NAD | 1.45 | 1.48 | 1.61 | 0.005 | 0.006 | 0.053 |
| | NADH | 1.02 | 1.35 | 2.20 | 0.897 | 0.129 | 0.077 |
| | NADP | 0.95 | 1.16 | 1.21 | 0.553 | 0.266 | 0.265 |
| | FAD | 0.76 | 0.98 | 1.18 | 0.068 | 0.833 | 0.229 |
| Phospholipid | CDP-ethanolamine | 0.79 | 1.18 | 1.05 | 0.124 | 0.141 | 0.788 |
| synthesis | Glycerophosphocholine | 0.30 | 0.90 | 0.93 | 0.010 | 0.318 | 0.608 |
| | Glycerophosphoethanolamine | 0.58 | 1.11 | 0.98 | 0.016 | 0.275 | 0.837 |

Example 1

Metabolomic Comparison of Patient-Derived Lung Tumor-Initiating and Isogenic Differentiated Cells The manner by which serine-glycine metabolites contribute to tumor initiation is not known in the art. TIC populations in cancer cell lines are poorly defined, providing limited utility for understanding TICs in patients. To overcome this limitation, two previously characterized TIC-enriched lines (LC1O and LC32) derived from resected primary NSCLC adenocarcinoma samples were grown as non-adherent tumorspheres (TS, TS1O and TS32) in serum-free media (FIG. 1a). These tumorsphere lines are highly tumorigenic as demonstrated by their in vitro colony-forming potential, and their ability to reproducibly form sizeable tumors when subcutaneously implanted into immune-compromised NOD.Cg-Prkdc$^{scid}$ Il2rg$^{tm1Wjl}$/SzJ (NSG) mice at limiting dilution cell frequencies (FIG. 1b-d).

Figure 7A:
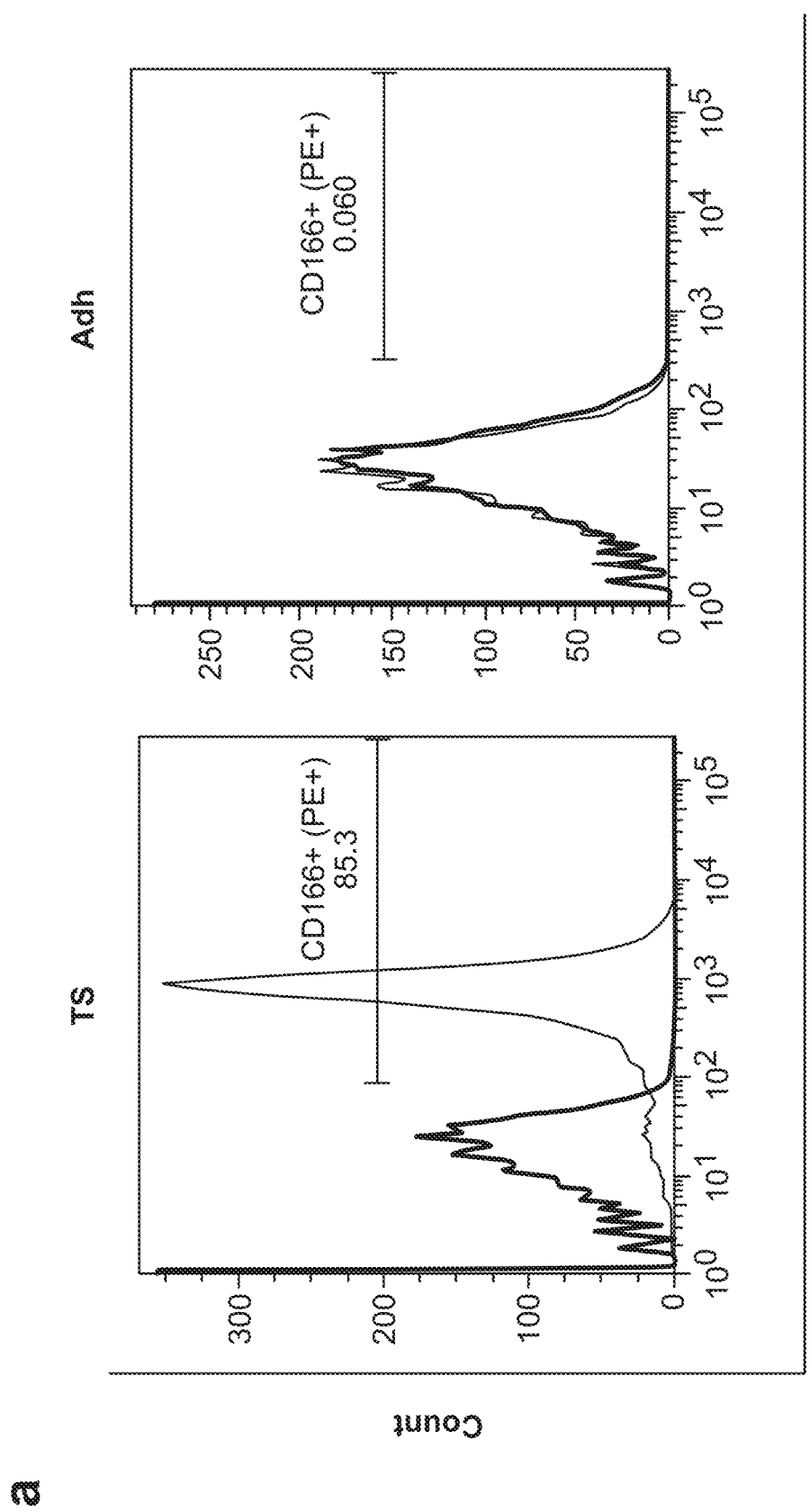
FIG. 7(a) is a graphical representation of CD166 staining of TS and Adh cells. Representative flow cytometry plots of indicated cells are shown. CD166 negative control (unstained TS cells) is presented in blue.
Figure 7B:
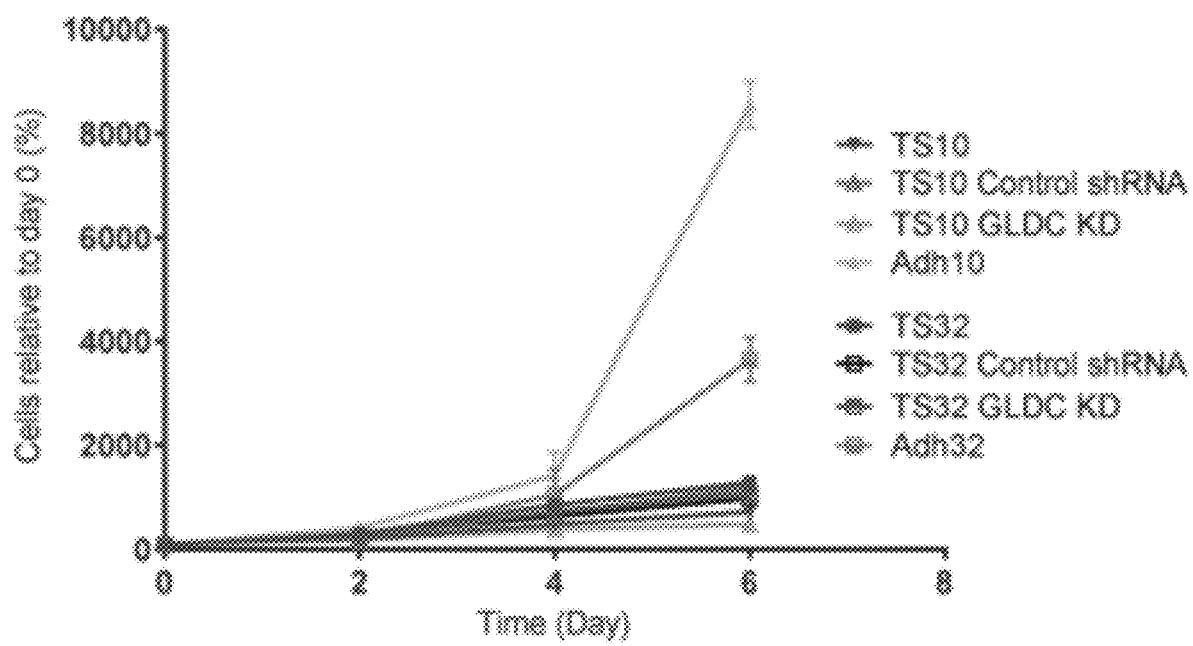
FIG. 7(b) is a graphical representation of TS and Adh cell proliferation under normal culture conditions. Cell numbers normalized to starting number were assessed every two days using the CellTiter-Glo (Promega) luminescence reagent. Error bars denote s.d.; n=6.

From each of these parental TS cells, two types of corresponding isogenic cell lines were derived. Firstly, adherent (Adh; Adh10 and Adh32) cells were generated by continual passage in serum-containing media, thus causing them to lose CD166 expression—a cell surface marker previously shown to be enriched in tumor-initiating populations (FIG. 7a). Secondly, stable GLDC-knockdown lines were generated using shRNA hairpin against GLDC (GLDC-KD; GLDC10 and GLDC32) and grown in parental TS media conditions, both the Adh and GLDC-KD cells were dramatically less tumorigenic than parental TS, forming very few colonies in soft agar and very small tumors in NSG mice (FIG. 1b,c). Limiting dilution assays also demonstrated at least a 40-fold decrease in TIC frequency in the Adh and GLDC-KD lines compared to the parental TS cells, with a complete abrogation of tumor-initiation ability when 10,000 cells were xenografted (FIG. 1d). Importantly, in vitro proliferation rates of these isogenic cells lines do not correlate with tumor-initiation potential (FIG. 7b). Adh cells, in fact, grew faster than both the TS and GLDC-KD cells, underscoring the decoupling of cell proliferation in vitro with tumorigenicity. Thus, TS cells are greatly enriched for TICs, whereas Adh and GLDC-KD cells are largely composed of differentiated cancer cells with high proliferative capacity but limited tumorigenic potential.

To determine whether specific metabolites are differentially produced or utilized by TICs compared to differentiated cells, an unbiased LC/MS-based metabolomics analysis was performed with the three isogenic lines (TS, Adh and GLDC-KD) derived from TS32 (FIG. 1e and Table 4). Distinct alterations in metabolite abundances were found across the three cell derivatives, with the most pronounced differences between TS and Adh cells (FIG. 1e). Glycolytic intermediates were enriched in Adh, relative to TS and GLDC-KD cells, attributable to their higher rates of proliferation, thereby demonstrating the Warburg effect in Adh cells (FIG. 7b). Lactate levels where lower in GLDC-KD cells, when compared to Adh and TS cells. Abundances of metabolites in Control knockdown and GLDC-KD cells stably expressing a shRNA resistant GLDC cDNA, were concordant to that of parent TS32 cells (Table 5) ruling out the possibility that metabolite changes were due to off-target effects of shRNAs.

From the global metabolomics analysis, three classes of metabolites stood out: 1) nucleotide intermediates, which are derived from serine-glycine and one-carbon pathway activity in TS cells and abrogated by GLDC knockdown; 2) branched chain and aromatic amino acids; and 3) metabolites related to the methionine cycle (FIG. 1e). A decision was made to focus on the methionine cycle and its associated downstream glutathione synthesis pathway for two reasons. Firstly, it represents a highly defined metabolic module in which the key metabolites such as methionine, SAM, SAH, glutathione and glutamine were strongly enriched (FIG. 1f-h). Secondly, the contributions of the methionine cycle to tumor initiation have not been previously established.

The methionine cycle is composed of two main steps (FIG. 1f). In the first step, methionine adenosyltransferase II alpha (MAT2A) consumes methionine and ATP to generate S-adenosyl methionine (SAM), which is the universal methyl group donor in cells. S-adenosyl homocysteine (SAH) is produced as a by-product of methylation reactions. The second step regenerates methionine via the reversible conversion of SAH to homocysteine by the SAH-hydrolase, SAHH. Methionine is subsequently resynthesized from homo-cysteine by using methyl-tetrahydrofolate ($CH_3$-THF) as a methyl donor; this is catalyzed by methionine synthase (MTR). Homocysteine can also exit the cycle by conversion into cysteine and finally to glutathione through a series of trans-sulfuration reactions. Of note, the serine-glycine pathway feeds into the methionine cycle through production of 1-carbon methylene-tetrahydrofolate ($CH_2$-

THF) metabolites that are catalyzed by GLDC and SHMT2; they are then reduced by MTHFR to $CH_3$-THF for methionine regeneration.

In Adh and GLDC-KD cells, methionine and SAH were consistently depleted. This provided the first indication that decreases in methionine cycle activity and cellular transmethylation were associated with the lack of tumor-initiating capabilities in differentiated cells (FIG. 1g). To reinforce the central importance of the methionine cycle in TICs, the expression of metabolic enzymes acting downstream of GLDC was examined in both sets of patient-derived cells. Protein levels of GLDC, SHMT2 and MTHFR were much higher in TS cells compared to Adh cells, while MTHFR levels were higher in Control knockdown TS cells when compared to GLDC-KD cells (FIG. 1i). Both results are consistent with the previous observations that there is a higher flux from the one-carbon pathway into the methionine cycle in TICs.

Additionally, knockdown of GLDC led to a similar decrease in steady state levels of $ATP^{33}$, a SAM precursor, as knockdown of SHMT2 (FIG. 7c). The decrease could be rescued by supplementing knockdown cells with formate, a cell-permeable one-carbon donor. This concurs with the observation that GLDC knockdown led to decreased abundance of nucleotides (FIG. 1e), and indicates that GLDC activity plays a prominent role in TIC through the one-carbon flux. On the other hand, formate supplementation could not rescue lowered ATP levels of Adh cells (FIG. 1d), even if SHMT2 or GLDC was re-expressed. Re-expressing GLDC in Adh cells also failed to fully rescue the tumorigenic potential of Adh cells (FIG. 1e). These data confirmed that the entire one-carbon pathway flux was downregulated in Adh cells (FIG. 1i), and demonstrates its role in supporting the tumorigenicity of TICs.

Interestingly, there was no significant change in SAM levels in GLDC-KD cells compared to TS cells, despite their decreased methionine levels (FIG. 1g). This may best be explained by decreased rate of cellular transmethylation reactions leading to decreased consumption of SAM and the supporting evidence of lower levels of SAH production. While a decreased level of SAH may be the result of an increased SAH consumption from glutathione synthesis in Adh and GLDC-KD cells, there was no such evidence because glutathione levels were similarly decreased in Adh and GLDC-KD cells (FIG. 1h). To confirm that decreased SAH levels between TICs and differentiated cells were due to reduced rates of transmethylation, the abundance of methylated histones, which are the most abundant end-products of cellular methylation reactions, was examined. Compared to TS cells, the majority of methylated histone modification marks were greatly downregulated in both Adh and GLDC-KD cells (FIG. 1j). The abundances of methylated histones in Adh and TS cells were also insensitive to alterations in cell culture conditions as TS cells grown transiently in Adh media and vice versa did not alter their levels (FIG. 7f). Thus, elevations in methionine levels and methionine cycle activities resulting in increased transmethylation reactions in TS cells suggest that increased methionine cycle flux may be a metabolic dependency of TICs but not their differentiated counterparts.

Methionine is an Indispensable Metabolic Substrate for Lung Tumor-Initiating Cells To assess the specific importance of methionine and other methylation-associated metabolites in TS cells, their role in conferring these cells with tumor-initiating capabilities was examined. The requirement for methionine by TS cells was first assessed using a transient 48 h starvation protocol because the general lethality associated with long-term (i.e. more than 7 days) methionine depletion could confound any conclusions (FIG. 2a). In addition, given the role of transmethylation reactions in regulating gene expression at the epigenetic level, it was sought to determine if short-term, transient changes in methionine cycle activity and cellular methylation were sufficient to induce longer term changes in TS cell tumorigenic: capabilities. Following 48 h starvation, the functional impact on cells in downstream assays performed under complete nutrient conditions were immediately assessed.

Figure 2E:
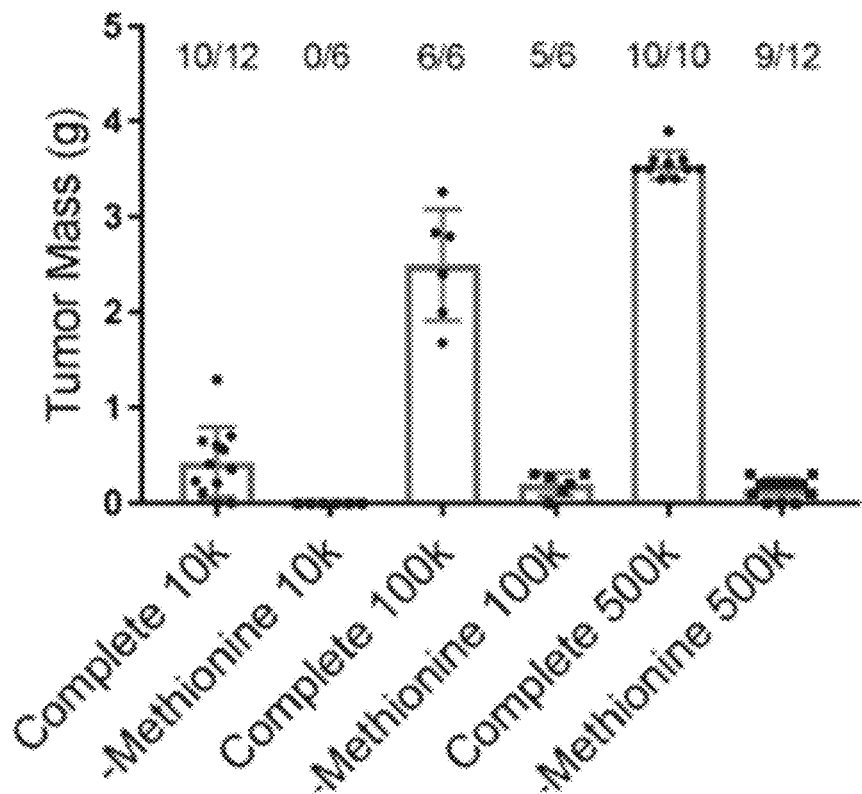
FIG. 2(*a*) is a schematic representation of metabolite starvation and downstream analyses. TS cells are starved in medium lacking in one specific metabolite for 48 h. Experiments were carried out thereafter in non-starvation conditions.

As expected, 48 h methionine starvation reduced methionine cycle activity. This was demonstrated by a dramatic decrease (~30 fold) in SAM levels and a slight decrease in SAH levels (FIG. 2b). This was accompanied by an overall decrease in histone methylation (FIG. 2c) in methionine-starved cells relative to those maintained under complete nutrient condition. To test the functional impact of short-term methionine starvation, TS cells were assayed for their colony-forming ability in vitro and their in vivo tumorigenic potential when xenografted into NSG mice (FIG. 2d and FIG. 8a). Surprisingly, TS cells that were transiently deprived of methionine did not regain their colony-forming abilities despite being returned to non-starvation conditions during soft agar assays. More strikingly, their in vivo tumor-forming ability was severely diminished as evidenced by a dramatic decrease in tumor load of 94% (FIG. 2d). Their tumor-initiating ability was likewise severely impacted when they were xenografted subcutaneously into NSG mice at limiting dilution cell frequencies, or when implanted orthotopically into the lungs when compared to their non-starvation counterparts (FIG. 2e, FIG. 8b). Remarkably, a shorter-term (24 h) starvation of TS cells was also sufficient to disrupt their tumorigenic potential, further underscoring their absolute dependency on methionine as a key substrate for tumor-initiation (FIG. 8c). Consistent with the loss of tumorigenic potential upon methionine starvation, a decrease in surface expression of the TIC marker CD166 was observed upon methionine starvation (FIG. 2d).

Figure 8E:
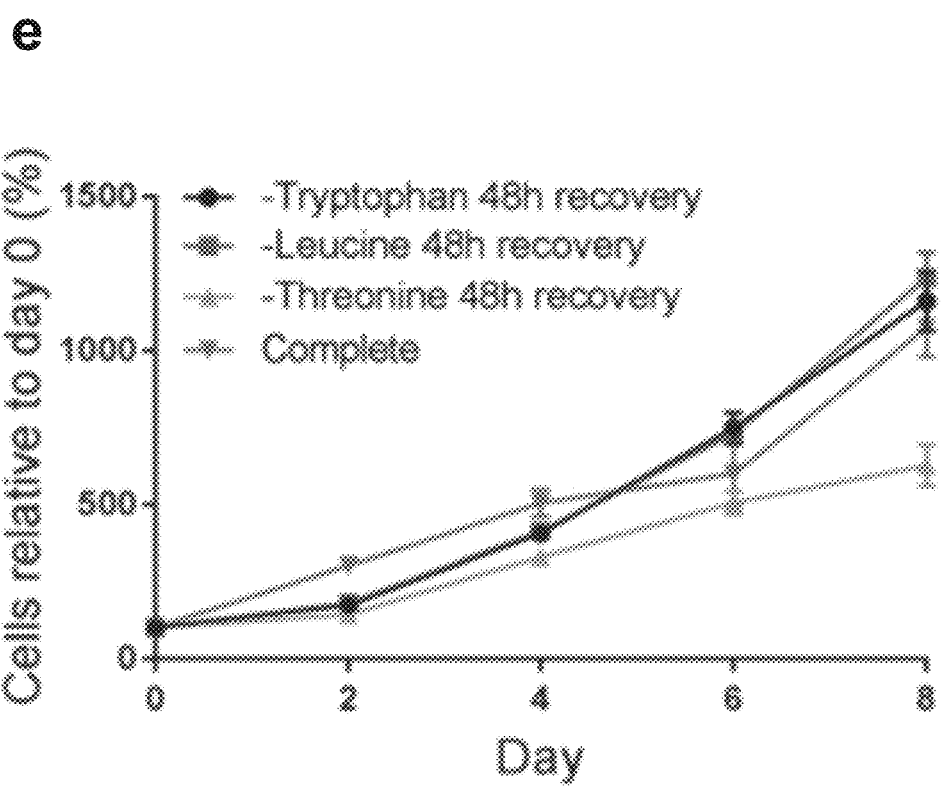
FIG. 8(e) is a graphical representation showing the proliferation of TS cells transiently starved of indicated amino acids for 48 h and then replated into complete media for another 48 h. Cell numbers normalized to starting number were assessed every two days using the CellTiter-Glo (Promega) luminescence reagent. Error bars denote s.d.; n=6.

Methionine is an essential amino acid. Hence, even short-term starvation may result in a general loss of cell viability that may be unrelated to tumor-initiation potential. To address this possibility, TS cells were transiently starved of other essential amino acids that include threonine, leucine or tryptophan, in a manner similar to methionine, prior to xenografting into NSG mice (FIG. 2f). Leucine and tryptophan were selected because they were enriched in TS cells (FIG. 1e), whereas threonine was previously documented to be important in influencing SAM levels in embryonic stem cells. Transient starvation of these essential amino acids did not severely cripple their tumorigenic ability, as the resultant tumor masses were only modestly reduced (on average, 16.4% reduction) when compared to cells cultured in complete nutrient medium, underscoring the strict dependency of TICs on methionine, but not other essential amino acids. Furthermore, these essential amino acid-starved cells remained viable as they regained proliferation when returned to complete media (FIG. 8e).

To further confirm that the defects in colony- and tumor-forming abilities were attributed to a loss of methionine cycle activity, and not a general loss of viability or translation inhibition, an attempt was made to rescue methionine-starved cells through three approaches (FIG. 2g, h). First, methionine starvation media was supplemented with 250 µM homocysteine to determine if TS cells could utilize homocysteine to regenerate methionine. Second, 500 µM SAM was supplemented into methionine starvation media to directly bypass the requirement for methionine for methylation. Third, methionine-starved TS cells were recovered for 48 h in complete medium before functional assessment.

Figure 2H:
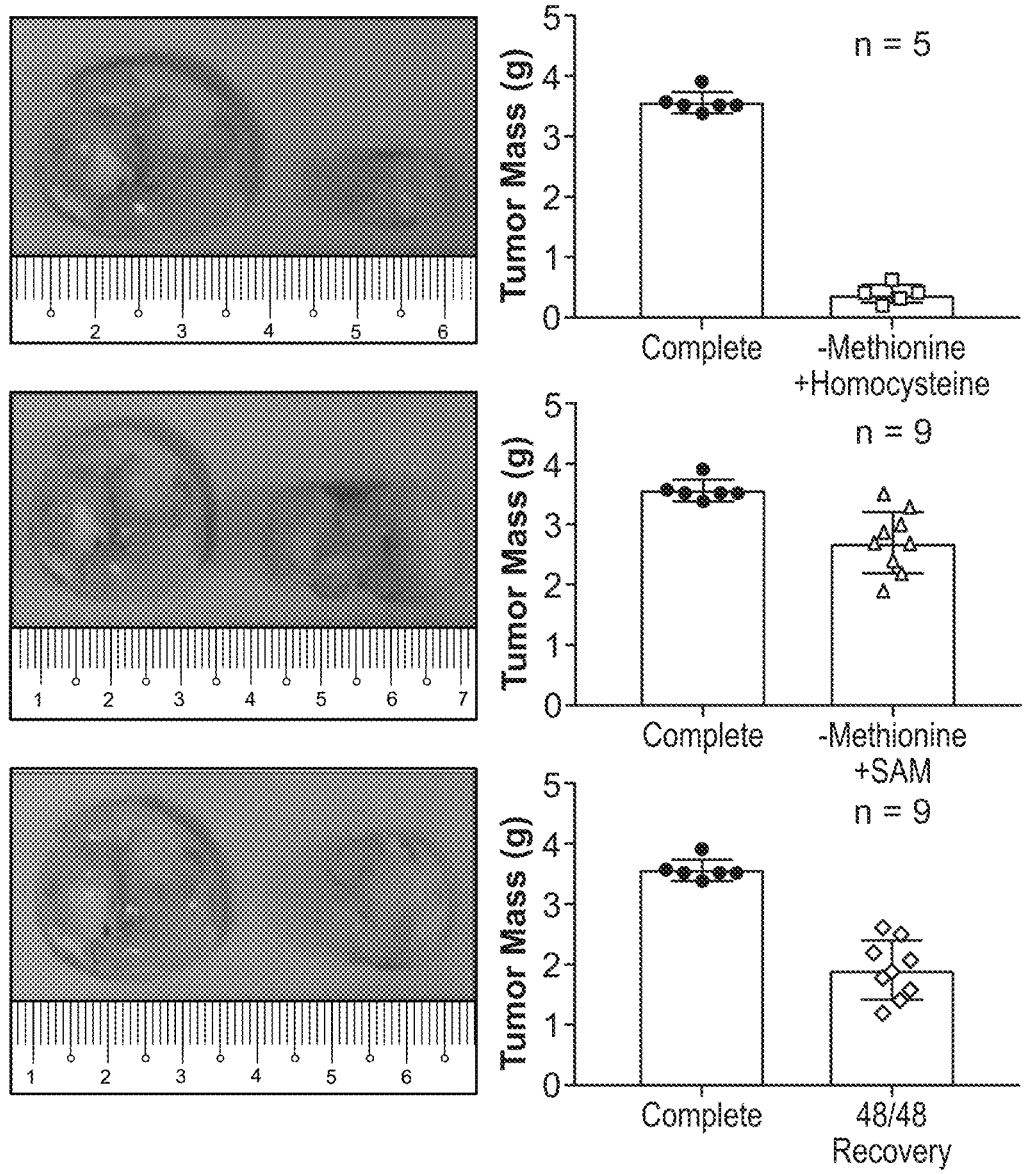

To dissect changes to the methionine cycle activity under these three rescue conditions, cellular histone methylation was first analysed (FIG. 2g). When methionine-starved TS cells were supplemented with SAM or allowed to recover for 48 h in complete medium, histone methylation was restored. Homocysteine supplementation, however, failed to rescue the effects of methionine starvation, indicating that TS cells require exogenous methionine to produce SAM for histone methylation (FIG. 2g.) Similar to changes in methylation, colony- and tumor-forming capabilities under methionine starvation conditions were rescued when SAM was supplemented or when cells were allowed to recover for 48 h in complete medium (FIG. 2h and FIG. 8d). Interestingly, the extent of rescue when cells were recovered for 48 h was not as dramatic as SAM supplementation. This suggests that transient depletion of methionine can impact the tumorigenic capability of TICs, presumably, by imposing long-term epigenetic alterations. These alterations can be averted by concurrent supplementation with SAM (FIG. 2h).

Figure 2I:
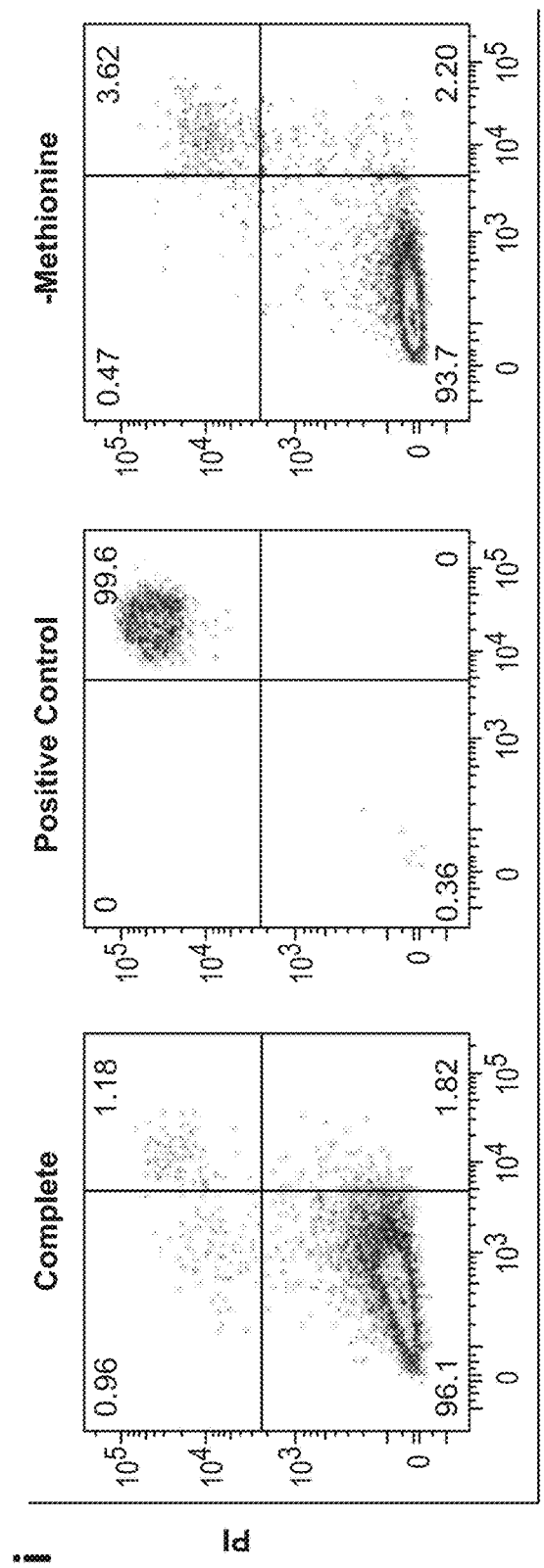
Figure 2I:
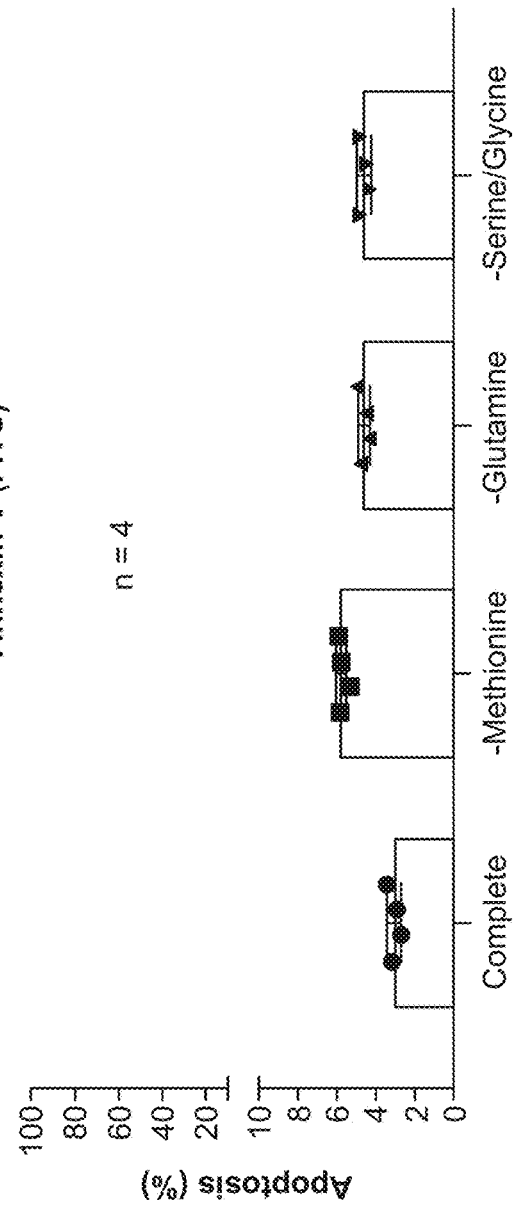
Figure 8I:
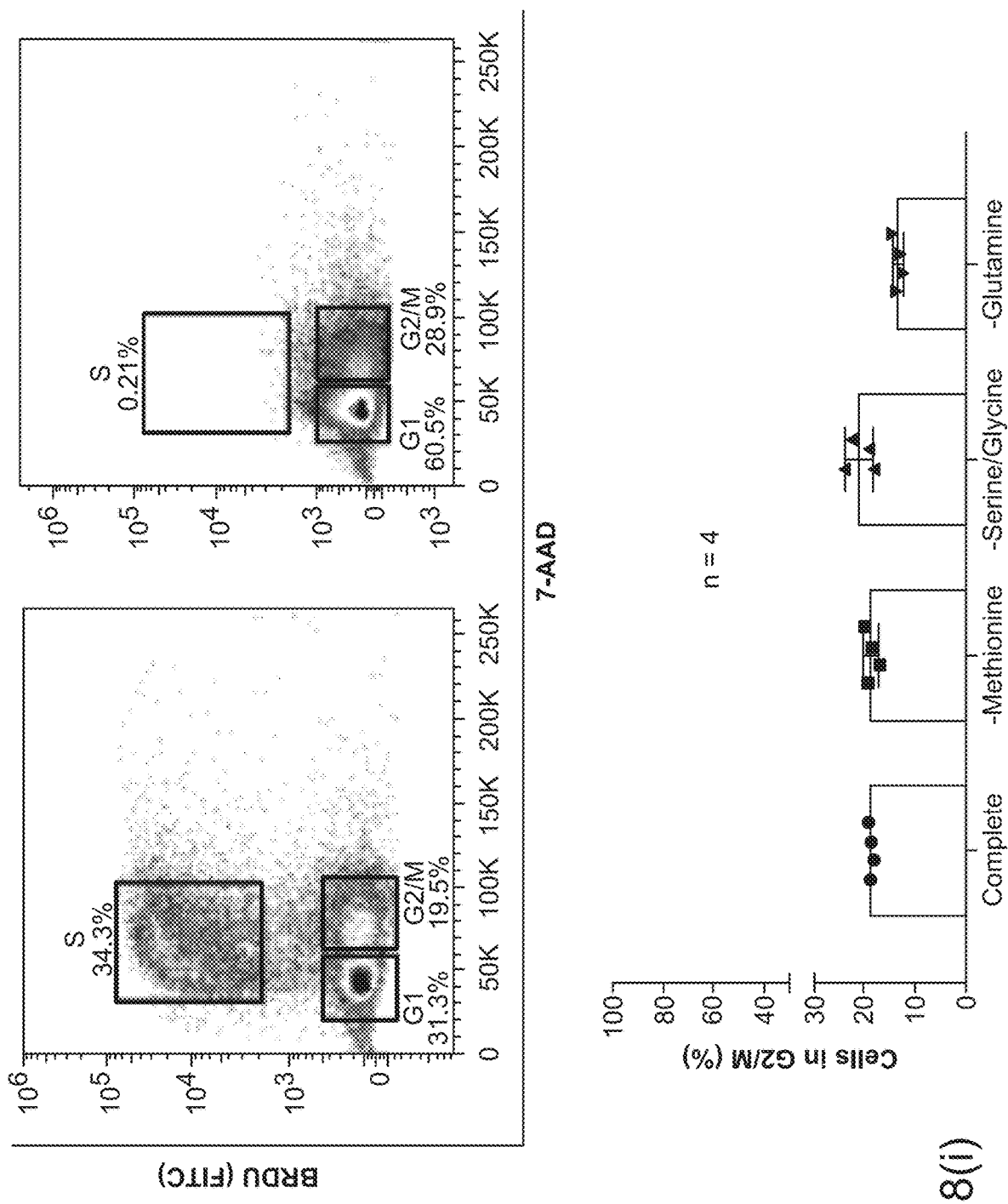
FIG. 8(i) is a graphical representation of the cell cycle analysis of TS cells cultured under amino-acid starvation conditions. TS cells were stained with BrdU and 7AAD. Representative flow cytometry plots of Complete and thymidine treated positive control cells are shown on the top. The proportion of cells in G2/M is shown in bar graphs at the bottom panel. Error bars denote s.d.; n=4.

As a comparison, TS cells were starved of glutamine or both serine and glycine in the same manner to compare the relative importance of methionine in TICs to other known cancer-associated amino acids. Of particular interest, glutamine level was also found to be most abundant in TS cells, relative to Adh and GLDC KD cells (FIG. 1h). Short-term glutamine starvation increased cellular histone methylation as a result of a decrease in α-ketoglutarate/succinate ratio (FIG. 2g), while combined serine and glycine starvation had no impact on bulk histone methylation levels (FIG. 2c). Surprisingly, glutamine or combined serine and glycine starved TS cells were only mildly hampered in their ability to form colonies in soft agar (FIG. 8a) and tumors in NSG mice, indicating they are, at least, transiently dispensable for TIC function (FIG. 2d). To exclude the possibility that transient amino acid starvation led to the loss of cell viability, an analysis was made for apoptosis and it was found that there was no large increase in the proportion of early apoptotic cells (Annexin-5 positive, Propidium Iodide negative) at 48 h (FIG. 2i). There was a slight increase (~2%) in the number of apoptotic cells starved of methionine but the overall proportion remained lower than glutamine or serine and glycine starvation (FIG. 2i). Returning cells that were starved under these conditions to complete media also led to a recovery of proliferation (FIG. 8h), indicating that they remain viable after transient starvation. Contrary to previous reports, methionine starvation did not lead to a block at the G2/M boundary (FIG. 8i).

The viability of cells was tested to determine if the cells were affected during the rescue conditions to ensure that non-viable cells are not subjected to downstream assays. Consistent with the TS cell starvation studies, the viability of cells in all three rescue conditions did not seem to be severely impacted. A slight increase in apoptosis was observed under the 48 h recovery condition, but proliferation rates were partially restored (FIG. 2j, k). These findings reinforced the observation that loss of tumor-forming capability in TICs was likely not the result of apoptosis or cell cycle arrest of viable cells, but mediated directly through the inhibition of methionine cycle activity.

The data, thus far, implicated methionine cycle and SAM production as key determinants in maintaining TIC function, and further highlighting the involvement of an epigenetic program that may be crucial for conferring tumorigenicity to TICs.

Example 2

Figure 3A:
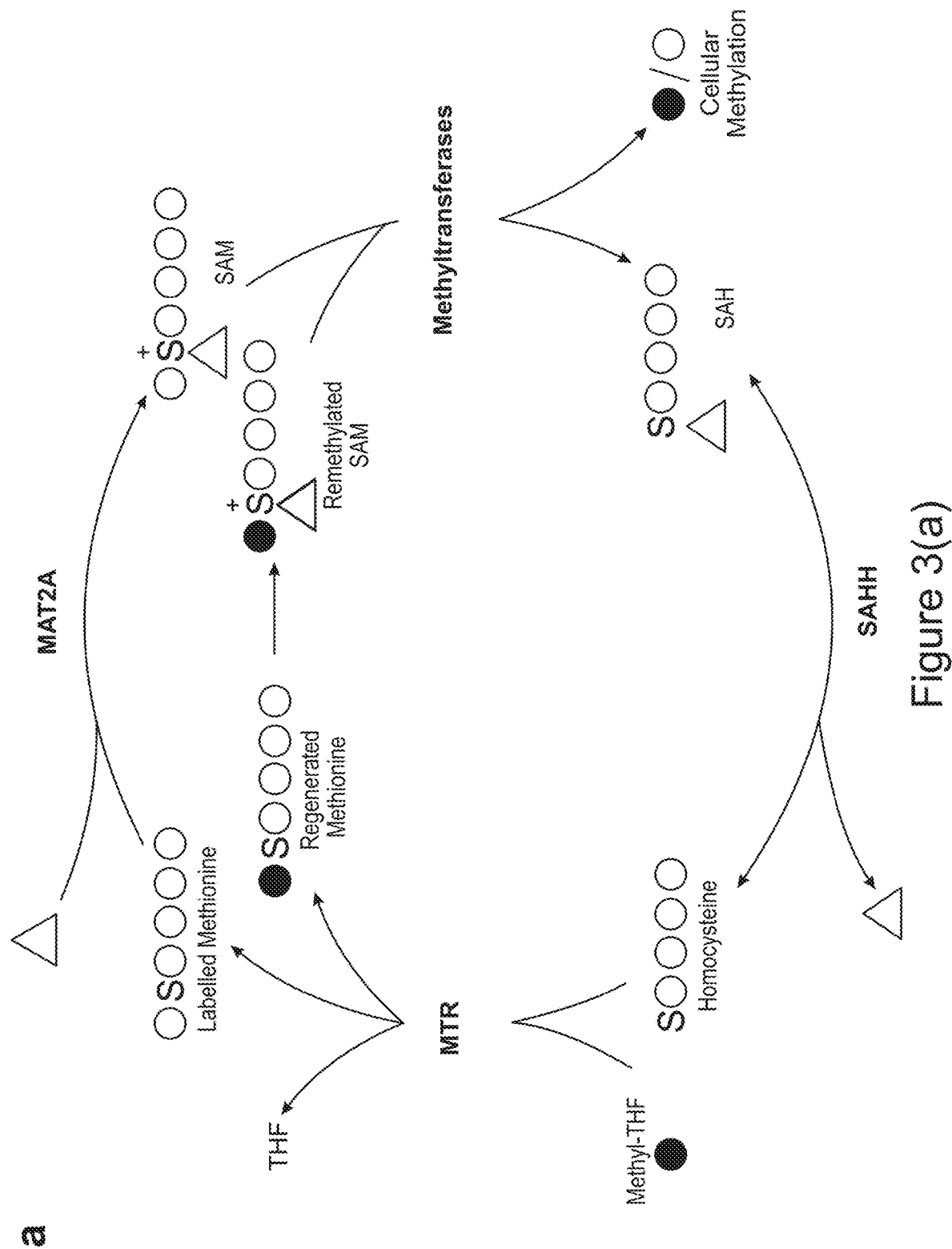
FIG. 3(*a*) is a schematic representation of $^{13}$C-labeled methionine as it progresses through the methionine cycle. Structural changes to $^{13}$C-labeled methionine as it cycles through the pathway. Carbon atoms are represented as circles. $^{13}$C: red circles; adenosine triphosphate (ATP): blue triangle. "+: positive charge. Black circle: unlabeled methyl group. Enzymes regulating each step are shown in block letters.
Figure 3B:
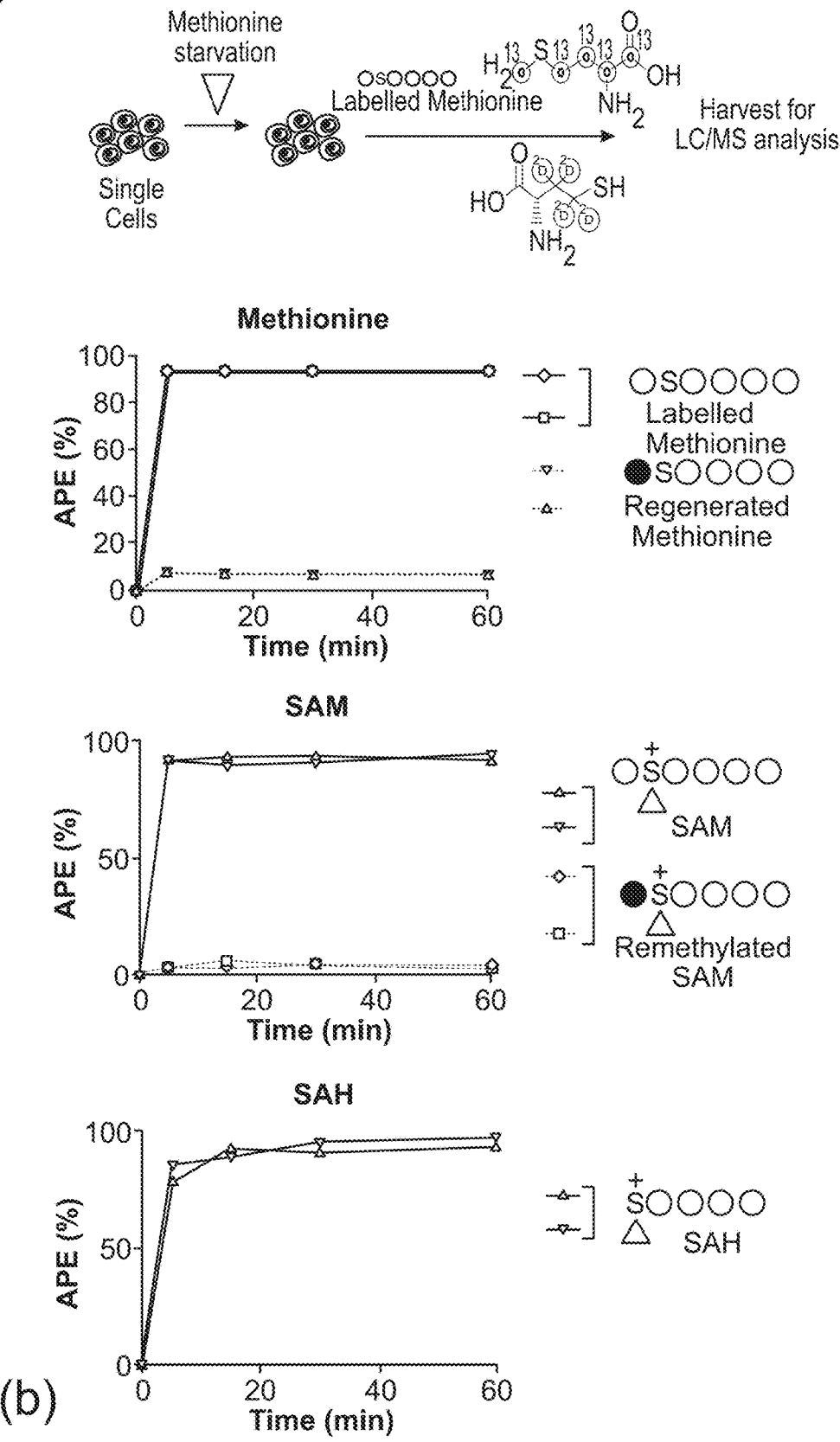
Figure 9A:
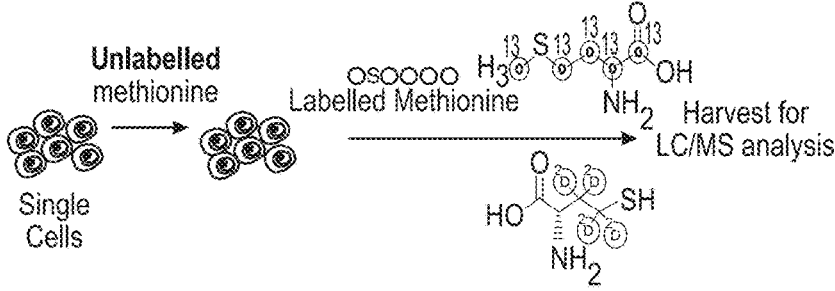
FIG. 9(a) is a schematic and graphical representation showing: Top: Experimental protocol. Cells were grown in media containing unlabeled methionine. Cells were then replated into media containing uniformly $^{13}C$-labeled methionine at t=0 and were analyzed thereafter. Bottom: Labeled methionine pulse-chase experiments. Metabolite species detected are indicated on the right, and proportional abundance (% APE), is indicated on the left. Data represent mean±s.e.m., n=3 technical replicate measurements. Curves for three biological replicates are shown.
Figure 9A:
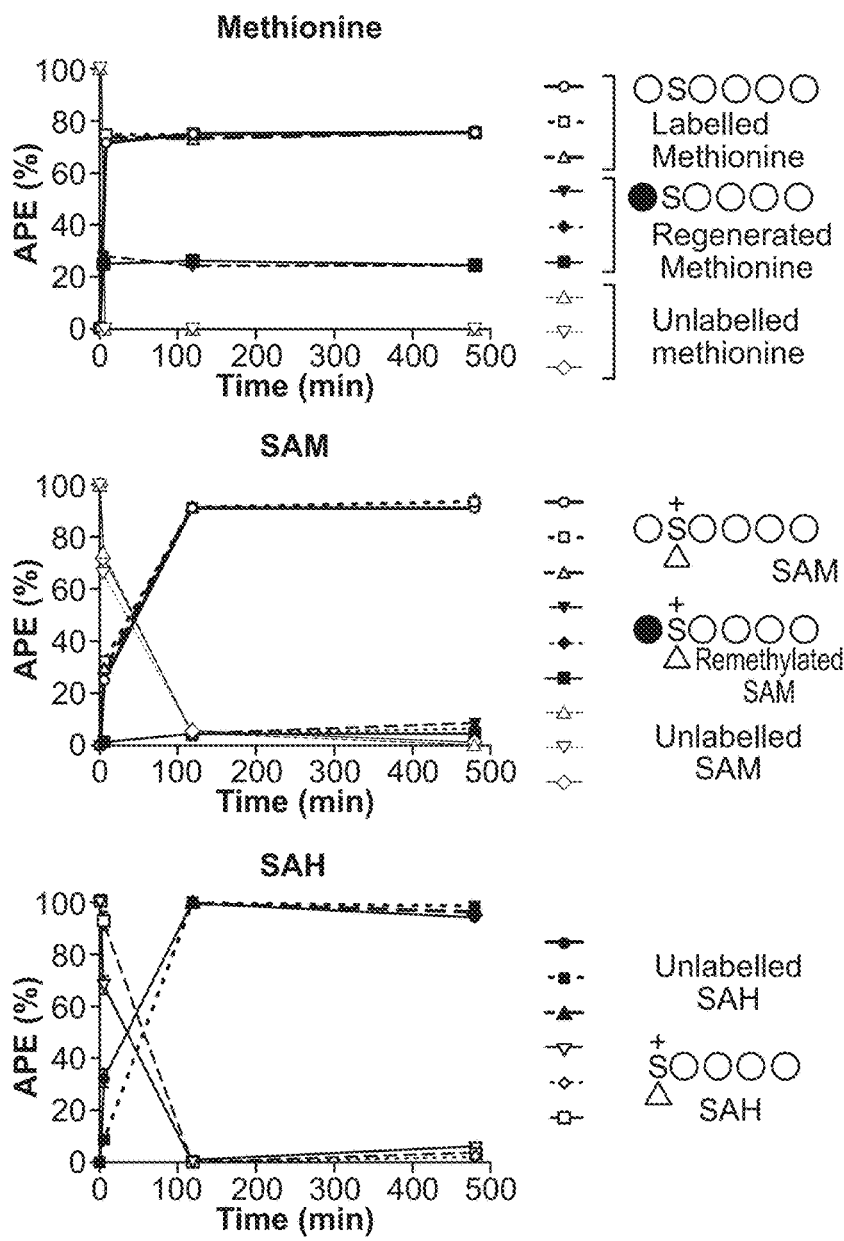

Dependency on Methionine Cycle Flux and SAM Leads to the Addiction of Tumor Initiating Cells to Methionine The failure of exogenous homocysteine to rescue methionine starvation in lung TS cells could indicate that de novo synthesis of methionine was insufficient to meet demands for methionine and SAM utilization. To trace the rate of methionine production and consumption, short-term pulse-chase experiments were first performed using carbon-13 ($^{13}$C) labeled methionine, followed by LC/MS detection and quantification (FIG. 3a). TS cells were initially starved of methionine for 16 h, followed by the addition of $^{13}$C-methionine (FIG. 3b; top). Labeled metabolites produced were tracked by LC/MS at various time points thereafter. Shortly after $^{13}$C-methionine was added, $^{13}$C-labeled methionine and metabolites of the derivative methionine cycle were rapidly detected in TS cells and reached steady state within five minutes (FIG. 3b). Interestingly, across multiple time-points, abundances of regenerated methionine and remethylated SAM (both of which have one less single $^{13}$C atom) remained comparatively low (FIG. 3b; green plot). Since it may be possible that starvation prior to pulse-chase may cause cellular stress and affect the steady state of methionine metabolism, pulse-chase was repeated in complete nutrient condition (FIG. 9a). Consistent with previous observations, labeled methionine levels reached steady state rapidly, and exogeneous methionine was exclusively utilized for SAM production. Taken together, de novo methionine regeneration rate utilizing recycled homocysteine was not sufficient to keep up with the rate of methionine consumption needed by TS cells to produce SAM for homeostasis, thereby resulting in a dependency to exogenously supplied methionine.

Figure 3C:
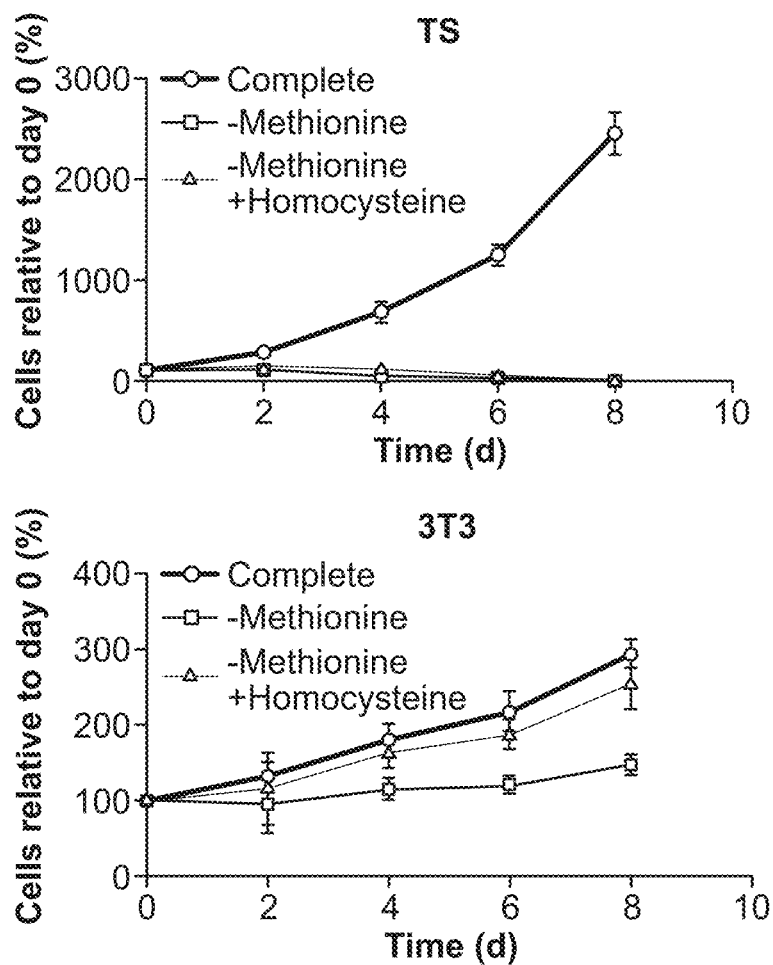
Figure 3D:
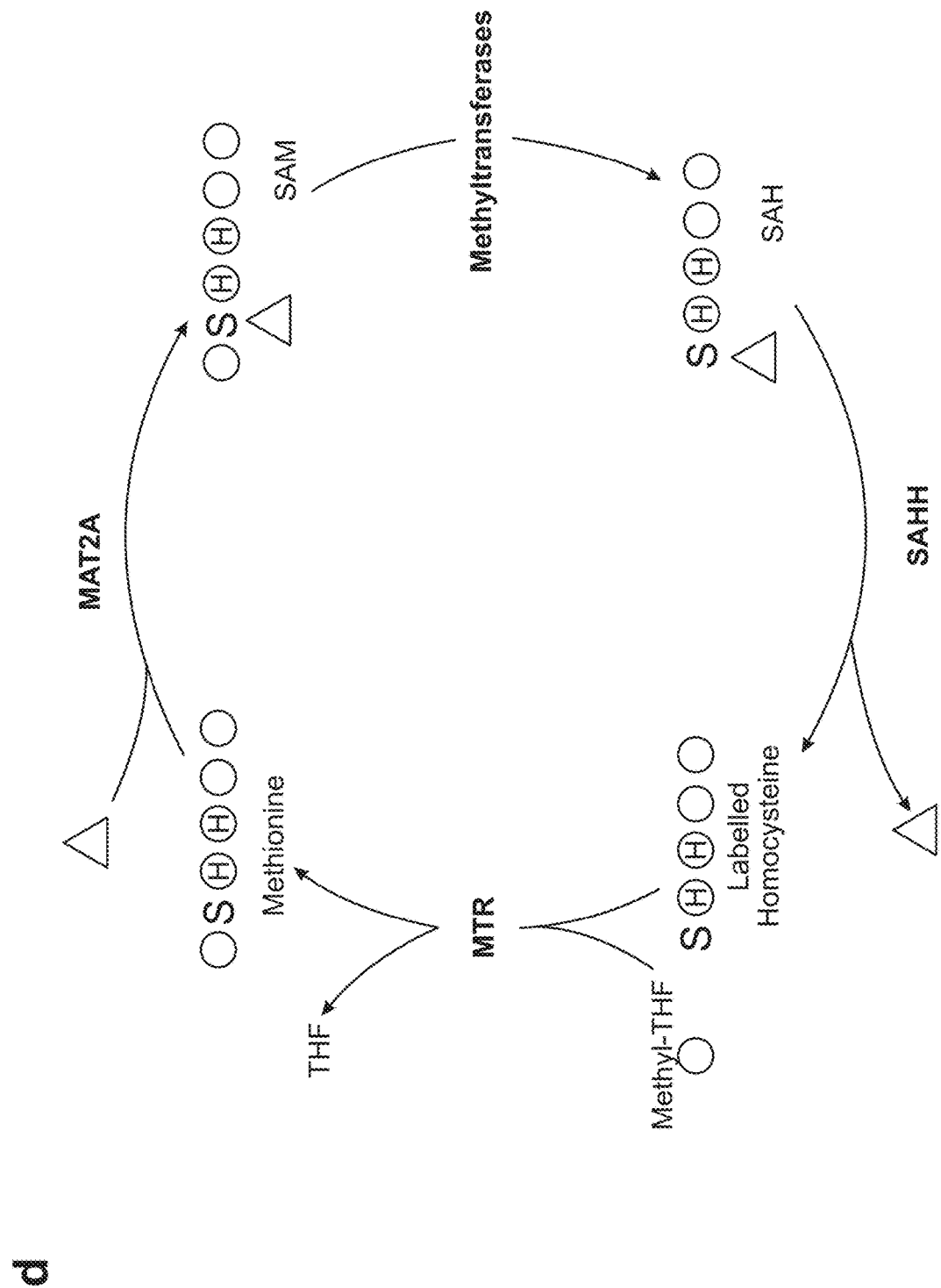
Figure 3E:
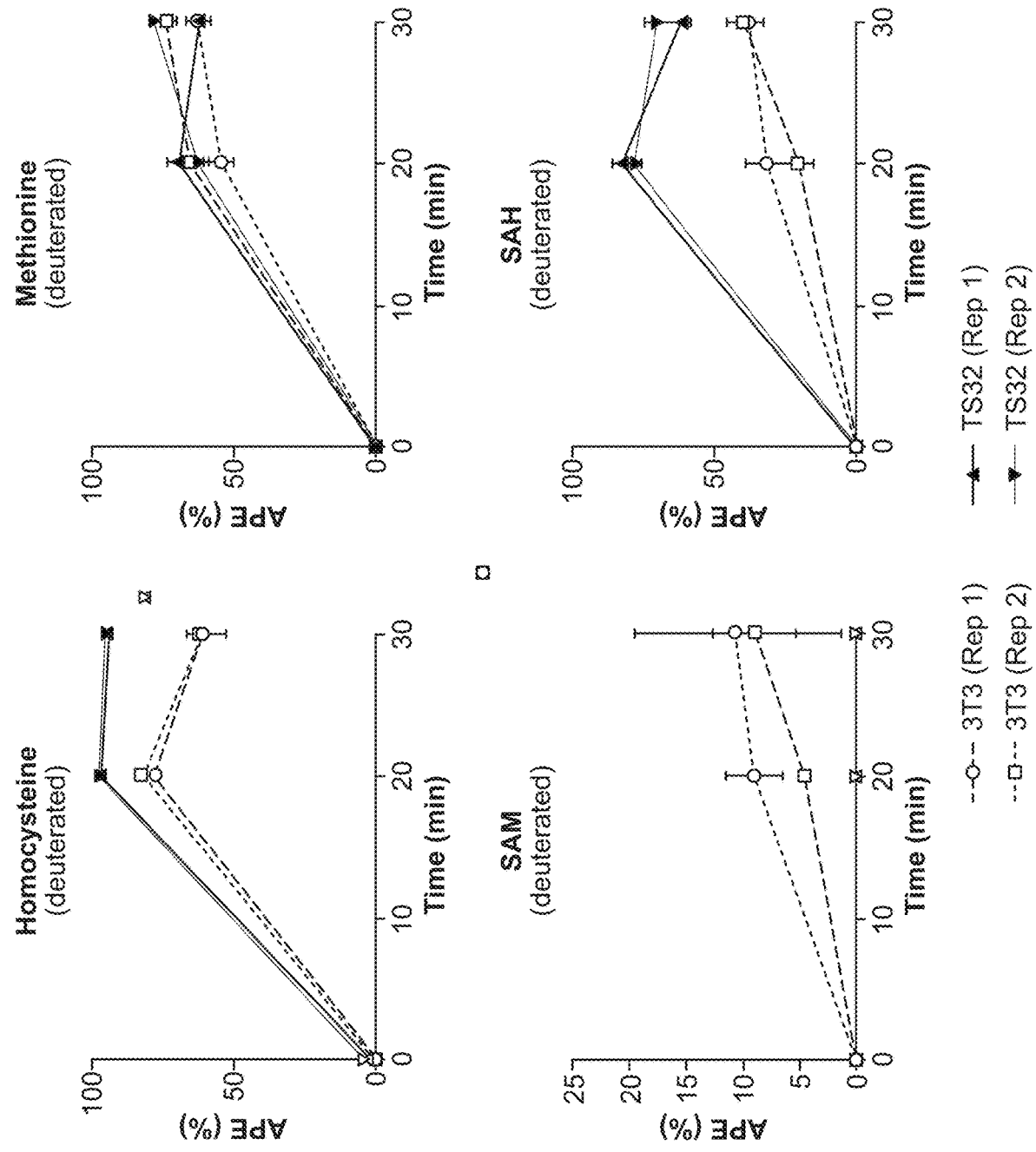

To further support the notion that lung TICs depend on exogenous methionine, it was sought to investigate the basis by which TS cells could not utilize homocysteine as a methionine substitute. As a comparison, NIH 3T3 cells were included because they were able to utilize homocysteine and grow in methionine starvation conditions despite lower relative abundances of all methionine cycle enzymes (FIG. 3c and FIG. 9b). Using deuterium-labeled homocysteine in pulse-chase experiments (FIG. 3d), an abundance of deuterated homocysteine and methionine was observed in TS and NIH 3T3 cells to be comparable at steady state, pointing to comparable rates of homocysteine import and methionine regeneration into both cell types (FIG. 3e, top panel). However in striking contrast to NIH 3T3 cells, deuterated SAM was not detected in TS cells (FIG. 3e, bottom-left), suggesting that SAM was rapidly consumed in TS cells. This is supported by the observation that deuterated SAH, the product of cellular methylation reactions, was produced at higher levels in TS cells compared to NIH 3T3 cells (FIG. 3e; bottom-right). This, despite low amounts of deuterated SAM that were detected from homocysteine in TS cells, clearly points to a prodigiously high rate of methylation reactions in TS cells that can account for the rapid consumption of both deuterated methionine and SAM. Consistent with these observations, a higher abundance of methylated histones was found in TS cells as compared to NIH 3T3 cells under non-starvation conditions (FIG. 9c). Hence, a combination of high methionine and SAM consumption rates in TS cells has led to exogenous methionine dependency.

Example 3

Contribution of the One-Carbon Pathway to the Methionine Cycle

TICs depend on the methionine cycle, which lies downstream of the one-carbon pathway. It was previously demonstrated that GLDC, a key rate-limiting step controlling serine-glycine metabolism, was crucial for TIC function, but its contribution towards the methionine cycle has not been addressed. Here, it was found that TICs, which were depleted of GLDC (GLDC KD), had decreased methionine regeneration and methylated histone levels (FIG. 1g, j). This led to dissection of the biochemical interactions between the methionine cycle and the one-carbon metabolism pathway, since methyl-THF units generated by MTHFR are used to regenerate methionine from homocysteine (FIG. 1f). The contributions of the methionine cycle in GLDC KD cells was first evaluated by supplementation with SAM for 48 hours to rescue cellular methylation prior to xenografting into NSG mice (FIG. 4a). This led to the reestablishment of histone methylation, at least transiently, in GLDC KD cells and an incomplete rescue of their tumorigenic potential (FIG. 4a, b). A recovery of MTHFR abundance was observed in SAM-supplemented cells (FIG. 4c).

One-carbon flux supplies MTHFR-generated methyl-THF units required for methionine remethylation. To understand the impact of GLDC and MTHFR downregulation in methionine cycle flux in TICs, deuterium-labeled homocysteine pulse-chase was performed in GLDC knockdown (GLDC KD) and MTHFR knockdown (MTHFR KD) cells (FIG. 4d and FIG. 10a). As expected, there was a dramatic decrease in the abundance of deuterated methionine despite similar rates of homocysteine import compared to parental TS cells, indicating a defect in the homocysteine remethylation step. In agreement with previous studies, a rapid accumulation of deuterated SAH was observed, thereby confirming that SAHH was driving the reverse reaction (i.e., back-flux) due to homocysteine accumulation. Strikingly, deuterated SAM accumulation stemming from residual homocysteine remethylation in both KD cell lines as a result of rapid SAH accumulation was also observed, thus leading to a competitive SAH binding to methyltransferase and global inhibition of methylation reactions. This underscores the importance of methionine remethylation as a mechanism for clearing homocysteine from cells, and also explains the chronic accumulation and underutilization of SAM in GLDC KD cells (FIG. 1g).

Figure 10C:
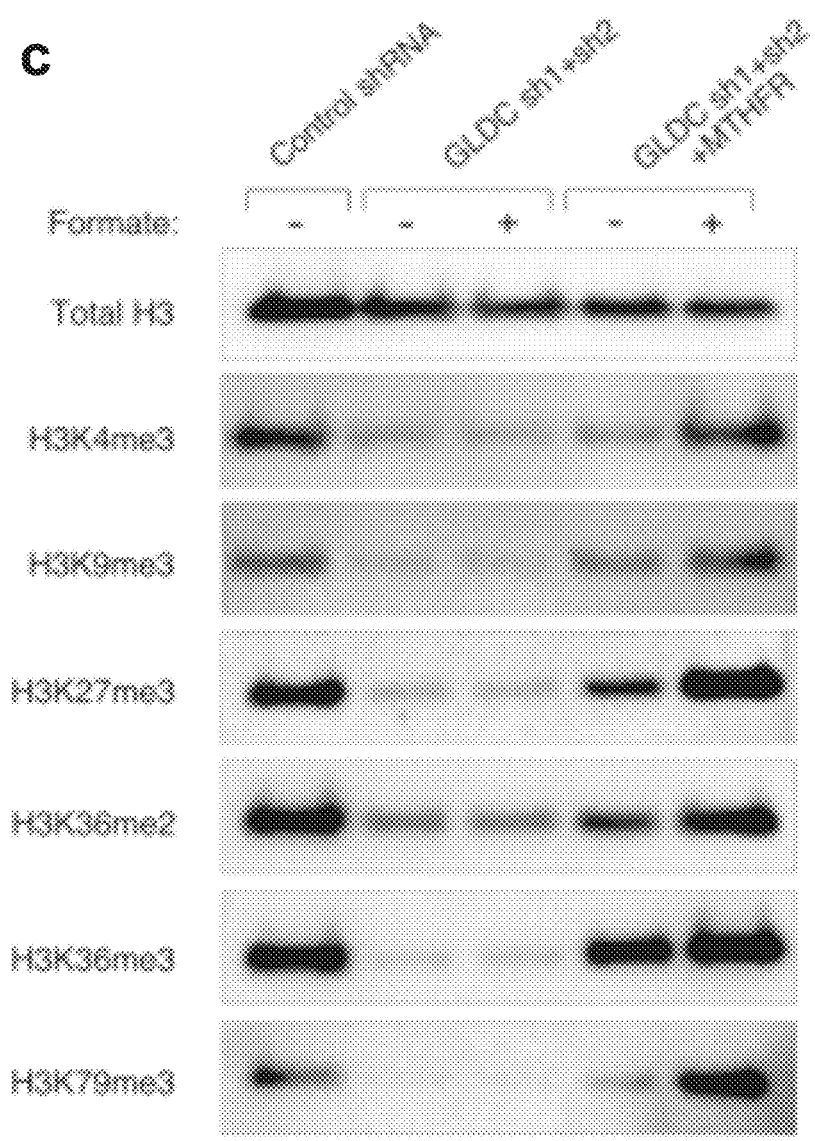
FIG. 10(c) is a photographic representation of the protein expression of methylated histones in Control KD, GLDC KD and MTHFR-overexpressing+GLDC KD cells supplemented with or without formate (0.5 mM). Histone H3 was used as loading control.
Figure 10D:
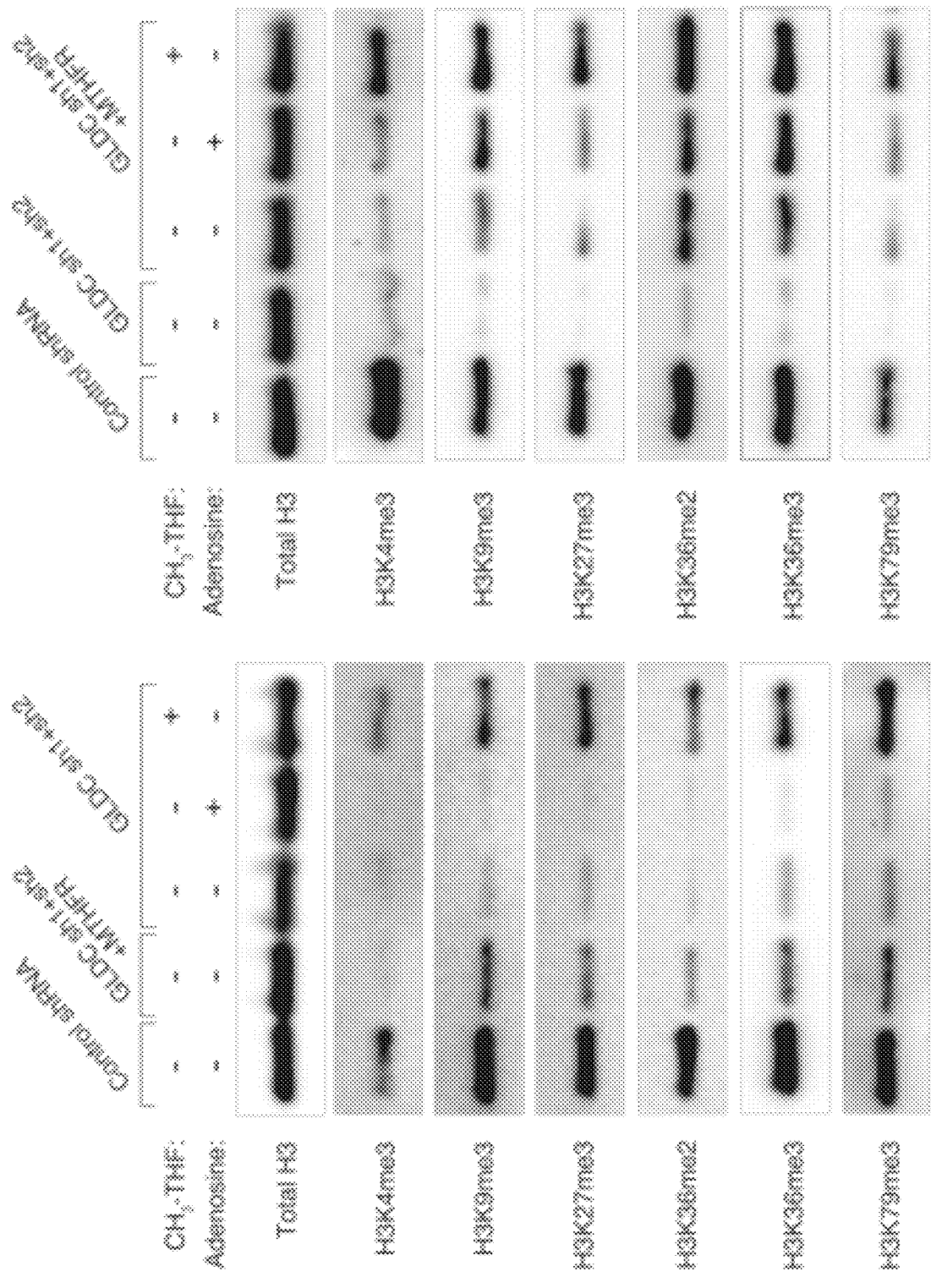
FIG. 10(d) is a photographic representation of the protein expression of methylated histones in Control KD, GLDC KD and MTHFR overexpressing+GLDC KD cells supplemented with or without methyl-THF (20 μM) or Adenosine (200 μM). Histone H3 was used as loading control.
Figure 10G:
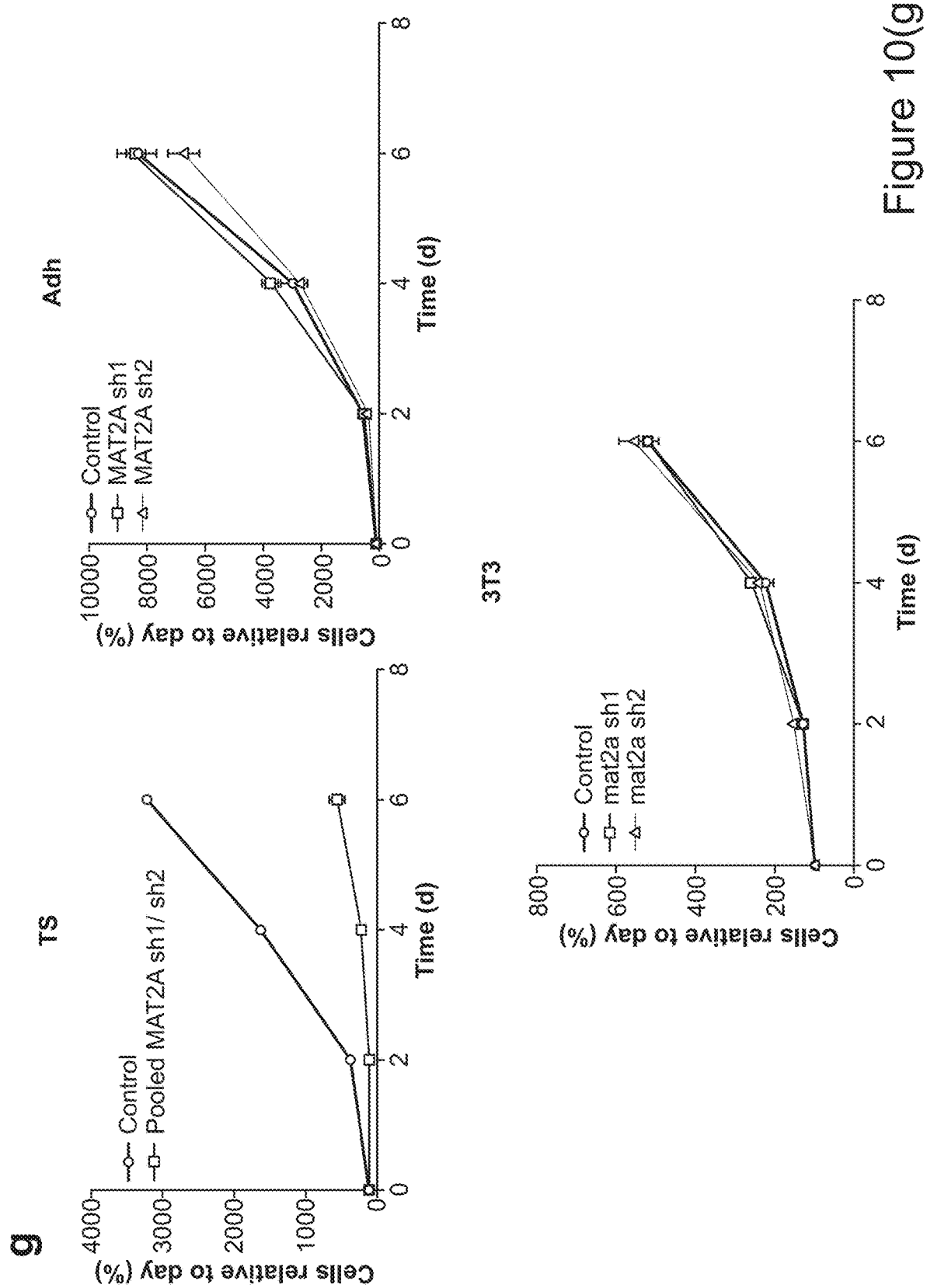
FIG. 10(g) is a graphical representation of the proliferation of TS, NIH 3T3 and Adh32 lines stably expressing MAT2A shRNA or Control shRNA. Cell numbers normalized to starting number were assessed every two days using the CellTiter-Glo luminescence reagent. Error bars denote s.d.; n=10.

Since MTHFR lie downstream of serine-glycine metabolism, and GLDC KD led to MTHFR downregulation, it was reasoned that its reactivation could, to some extent, rescue the phenotype of GLDC KD TICs (FIG. 1b-d). Overexpression of MTHFR in GLDC KD cells, indeed, led to a partial rescue of histone methylation levels and their tumorigenicity (~55%) (FIG. 4e, f). Conversely, depleting MTHFR by shRNA led to large decreases in histone methylation, soft agar colony- and tumor-forming capabilities (FIG. 4g, h; FIG. 10a). MTHFR overexpression in GLDC KD cells could not fully restore histone methylation levels to that of Control shRNA knockdown cells because one-carbon flux remained crippled from GLDC knockdown. To understand the context by which one could elicit a complete rescue in the methylation activity, metabolite supplementation in GLDC KD or MTHFR overexpressing+GLDC KD cells (FIG. 10b-e) was performed. Supplementation of formate in GLDC KD or MTHFR overexpressing+GLDC KD cells only fully rescued histone methylation of the latter, indicating that MTHFR and homocysteine re-methylation was critical in maintaining methylation activity (FIG. 10c). Indeed, only direct supplementation of $CH_3$-THF to bypass the block at the MTHFR step led to a rescue of histone methylation in GLDC KD cells (FIG. 4d). Even though one-carbon flux was also important in maintaining ATP pools[33] (FIG. 7c)—substrates for SAM synthesis—formate or adenosine supplementation did not rescue histone methylation in GLDC KD cells even though they rescued ATP levels (FIG. 4d and FIG. 10e). Taken together, these data indicate that the one-carbon pathway, acting through MTHFR and homocysteine re-methylation, plays a critical role in controlling the flux of methyl-THF units into the methionine cycle thereby preventing the accumulation of homocysteine.

Figure 4H:
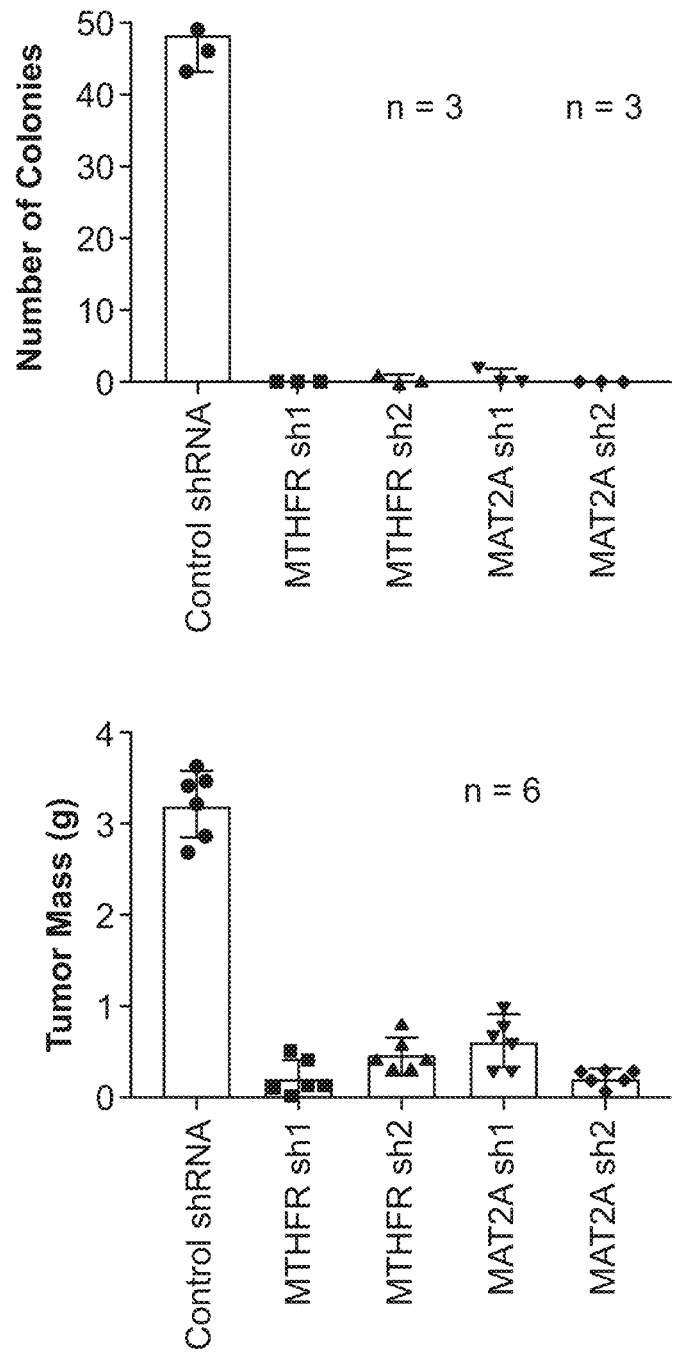
FIG. 4(*a*) is a photographic representation of a Western blot analysis of GLDC KD cells supplemented with SAM. SAM (500 µM) was supplemented to GLDC KD cells for 48 h and then harvested. Histone H3 is used as loading control.
FIG. 4(i) is a photographic and graphical representation of the effect of MTHFR and MAT2A knockdown on tumor formation abilities of TS cells. Top: Number of crystal-violet stained colonies formed from knockdown cells; 5000 cells per well were plated. Error bars denote s.d.; n=3. Bottom: Tumor mass in NSG mice following transplantation of 500,000 TS, MTHFR KD or MAT2A KD cells. Tumors were weighed 6 weeks post-transplantation, or when they reached 2 cm in diameter. Error bars denote s.d.; n=6 for all injections.
FIG. 4(j) is a photographic representation of MAT2A immunohistochemistry of a NSCLC tumor microarray (n=152). Representative images and staining intensity grades (indicated in the upper right corner) shown at the top. A contingency table correlating the staining intensity of MAT2A with grade of NSCLC is shown below. Chi-square p value is indicated at the bottom right.
FIG. 4(k) is a photographic representation of co-immunofluorescence staining of CD166 (cyan) and MAT2A (red) on lung cancer patient tumors, counterstained with DAPI (blue). Representative images of primary NSCLC (left) and metastatic lymph node (right) tumors are shown. White arrows indicate representative cells where CD166 (cyan) and MAT2A (red) staining overlap. White scale bars, 40 μm.

Because SAM is consumed at an exceedingly high rate in TS cells and is generated from exogenous methionine in a rate-limiting reaction by the enzyme MAT2A, it was reasoned MAT2A could be a potential therapeutic target. To assess the contribution of MAT2A in conferring tumorigenic capabilities to TICs, MAT2A was knocked down in TS cells (FIG. 10a). As expected, loss of MAT2A led to a dramatic reduction in histone methylation (FIG. 4g). MAT2A knockdown TS cells also exhibited impaired soft agar colony- and tumor-forming capabilities when xenografted into NSG mice, phenocopying methionine starvation and GLDC knockdown phenotypes shown earlier (FIG. 4h). In contrast, knockdown of MAT2A had little or no effect on the proliferation of differentiated Adh or NIH 3T3 cells, underscoring its functional specificity in tumor-initiating TS cells and as a therapeutically useful drug target in lung cancer (FIG. 10f, g).

Figure 4K:
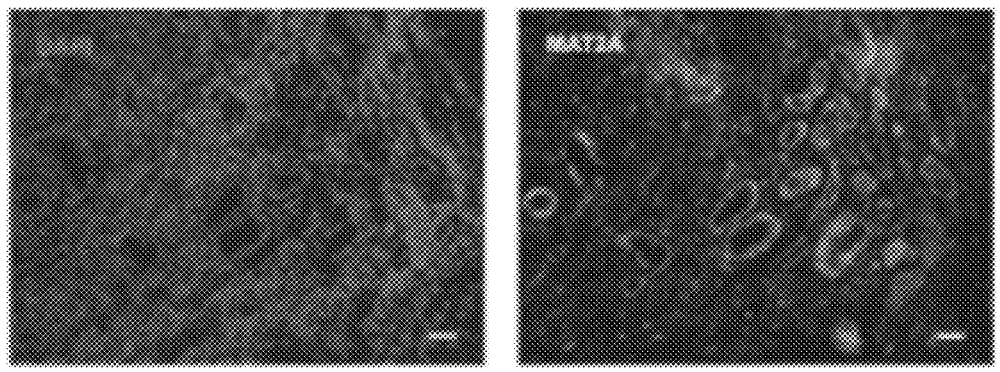
Figure 4K:
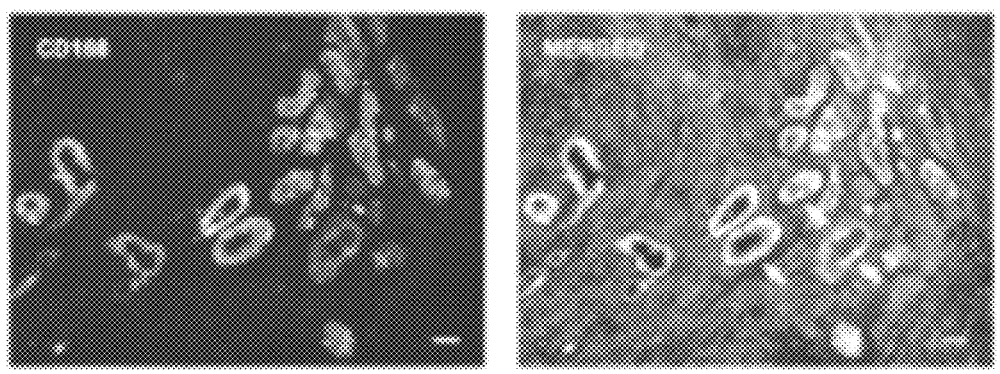
Figure 4K:
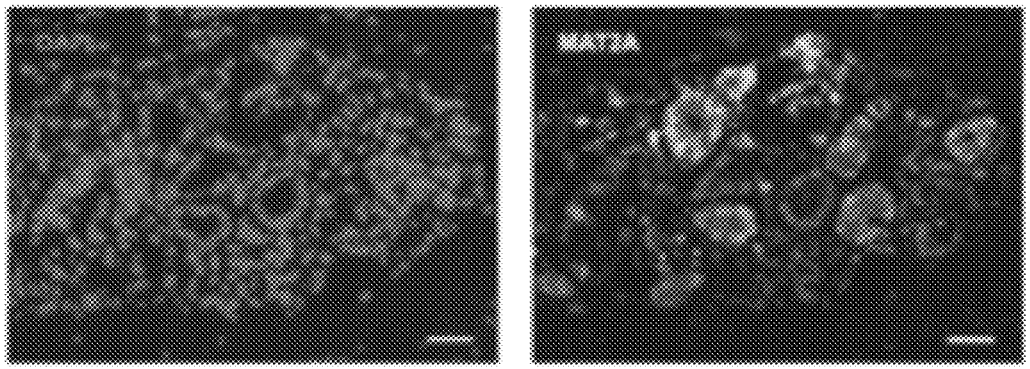
Figure 4K:
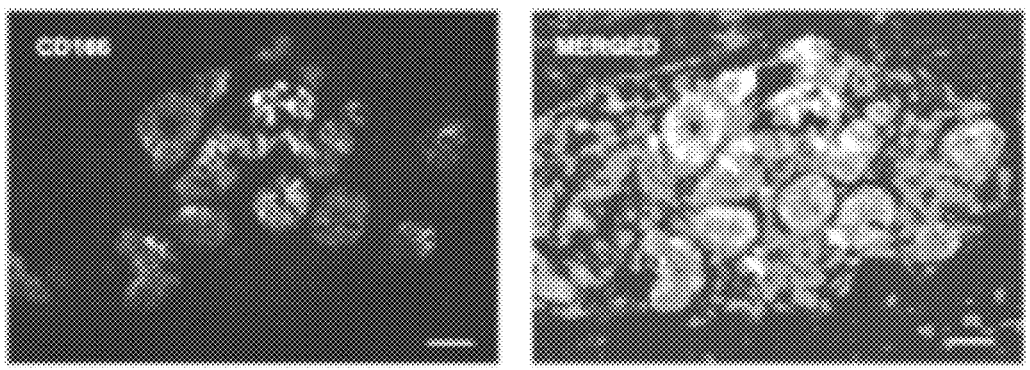
Figure 10H:
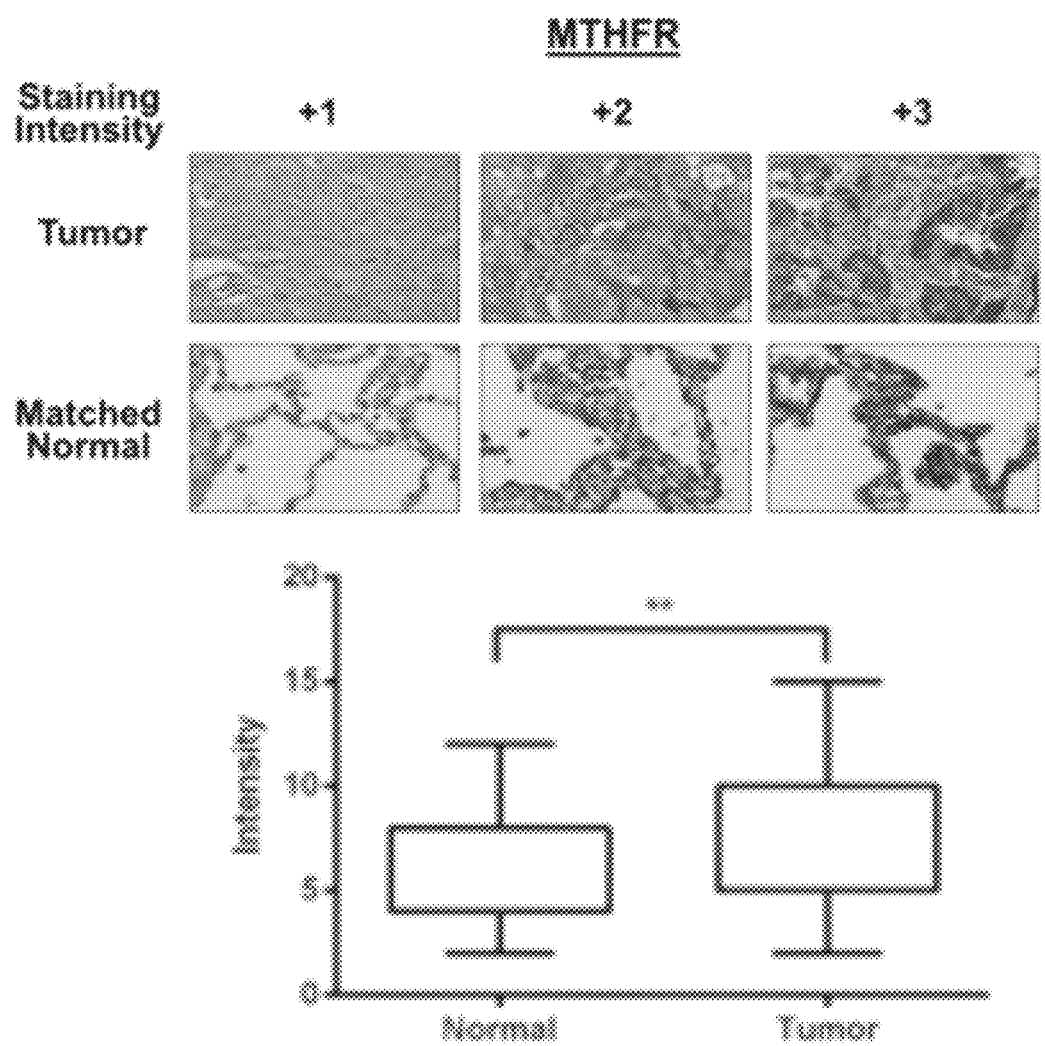
FIG. 10(h) is a photographic representation of MTHFR immunohistochemistry staining performed on 47 paired tumor and adjacent normal sections. Representative staining intensity is shown (top). Tumor samples were classified by intensity (bottom left). Box and whisker plot (bottom right) compares the average staining intensity of tumor and normal sections. Intensity is defined as the product of maximum immunostaining intensity and percentage of tumor cells stained. ** denotes p=0.0005 by paired Student's two-tailed t-test.

To establish the clinical relevance of MAT2A and MTHFR expression in lung adenocarcinoma, MAT2A and MTHFR protein abundance in a panel of patient non-small cell lung cancer (NSCLC) tumors were assessed to determine their association with cancer progression (FIG. 4i; FIG. 10h). Not surprisingly, both proteins were overexpressed in the majority of human lung tumors, but not in normal lung tissues. Using another panel of NSCLC tumors with tumor grading information, it was examined if MTHFR or MAT2A expression was correlated with grade (FIG. 4j). Strikingly, MAT2A expression was strongly expressed in high grade primary tumors or metastases, while such correlations were not seen with MTHFR expression (FIG. 4j; FIG. 10i). It was furthermore, noted that CD166 expression, which was previously demonstrated to be a marker of lung TICs, was co-expressed with MAT2A-expressing cells (FIG. 4k). It was further determined whether TICs differed from normal lung stem cells in MAT2A expression using the CD166 surface marker expression that was previously found enriched in both stem cell types. Interestingly, CD166+ cells isolated from a human tumor expressed MAT2A that was absent from the corresponding counterparts found in normal lung tissues (FIG. 10j).

Example 4

Small Molecule Perturbation of the Methionine Cycle Impacts the Tumorigenicity of TICs To evaluate the methionine cycle as a therapeutic target in lung TICs, small molecule inhibitors that target enzymes within this pathway were employed, mimicking the effects of short-term methionine starvation (FIG. 5a). two inhibitors known to perturb methionine cycle activity and cellular methylation levels: 1) MAT2A inhibitor, FIDAS5; and 2) SAHH inhibitor, D9, which is an analog of DZNep. In a manner similar to amino acid starvation studies, TS cells were exposed transiently to the compounds for 48 h in culture and were immediately used for downstream tumorigenesis assays.

Figure 5D:
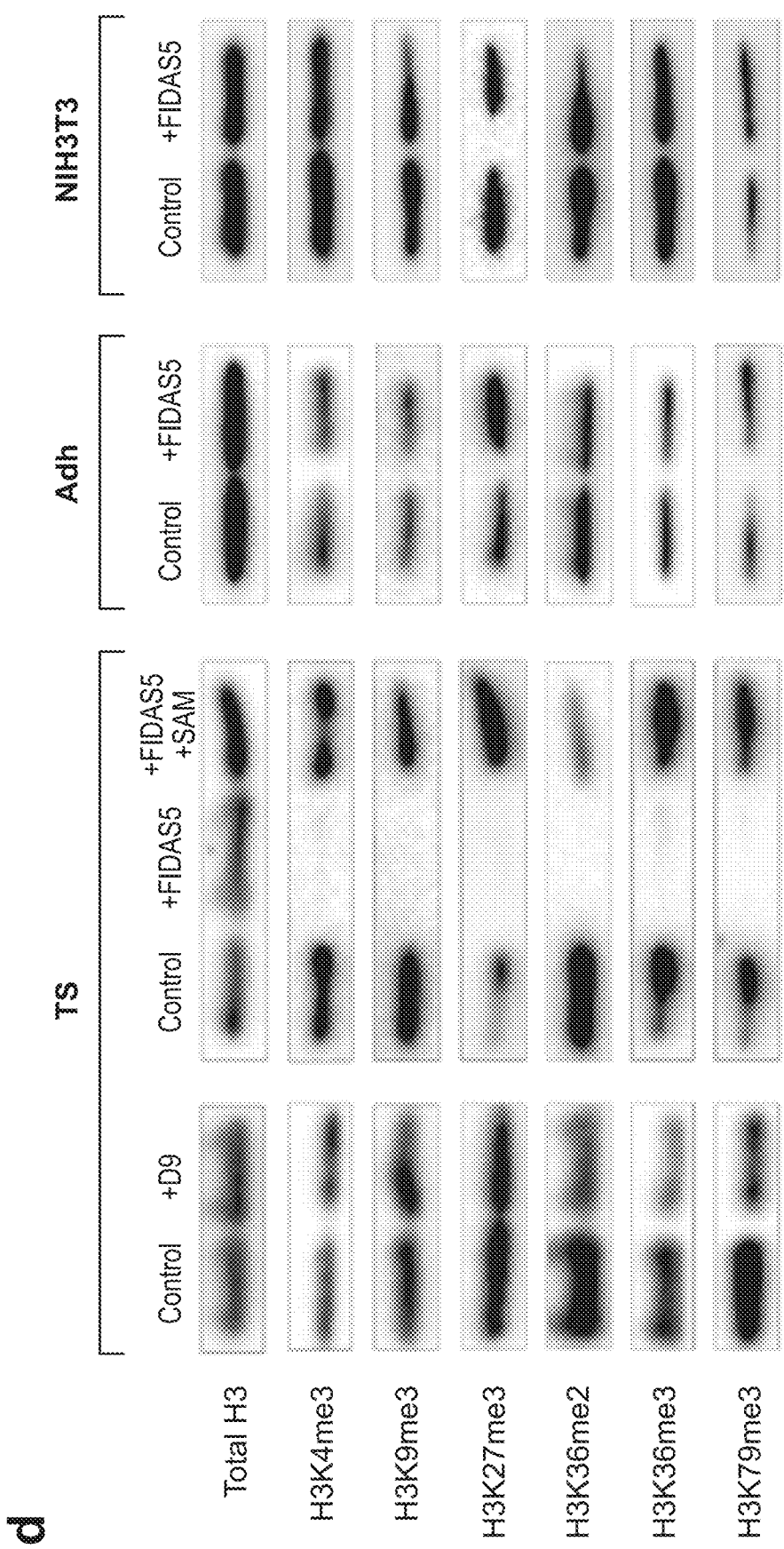
FIG. 5(d) is a photographic representation of a western blot analysis of cell lines treated with specified Inhibitors. Total Histone H3 is used as loading control.
Figure 5G:
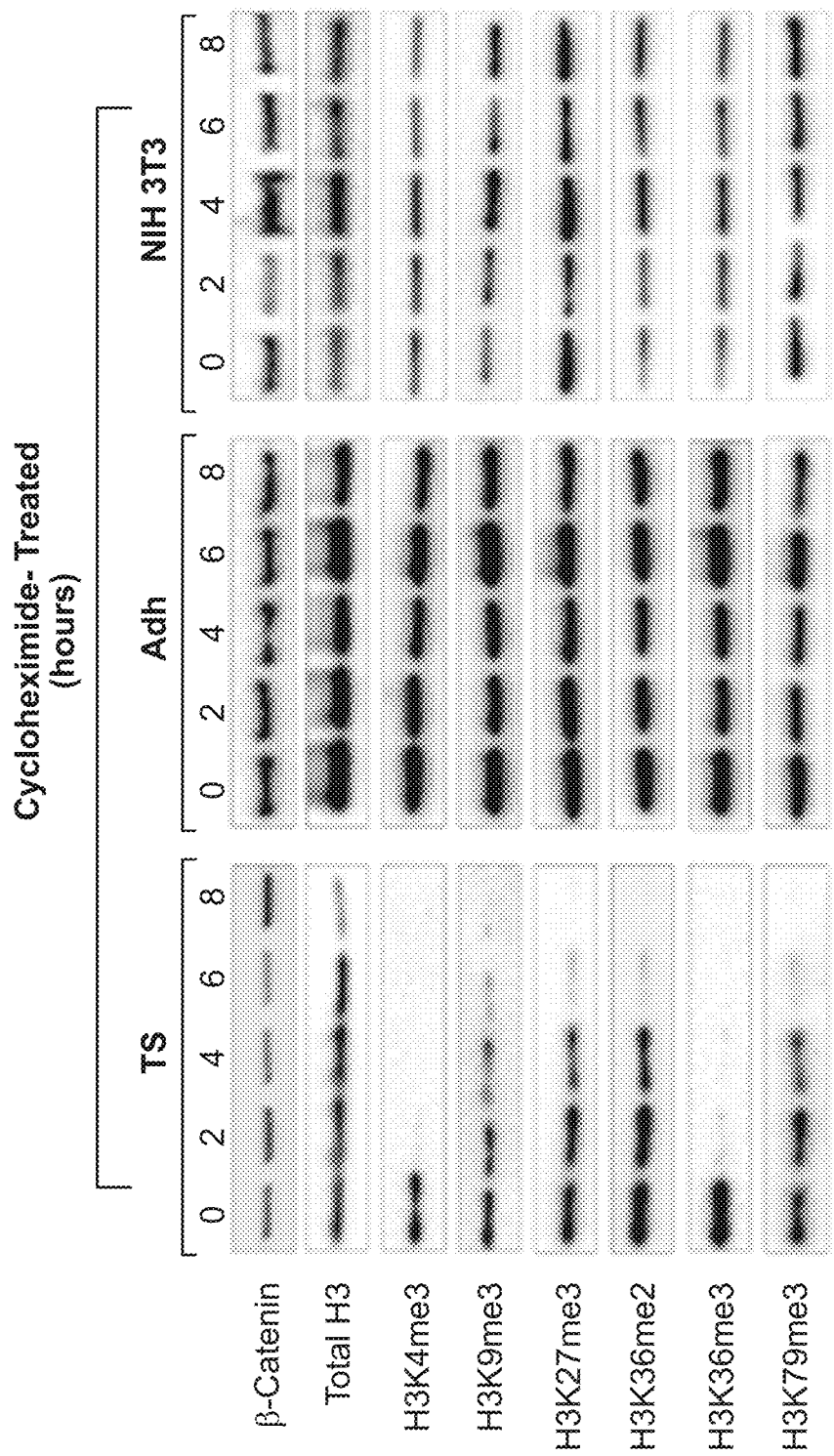
FIG. 5(g) is a photographic representation of western blot analysis of TS and NIH 3T3 cells after cycloheximide treatment. Cells were treated with 20 μg/ml cycloheximide and then harvested at indicated time points. β-catenin was used as loading control.
Figure 5H:
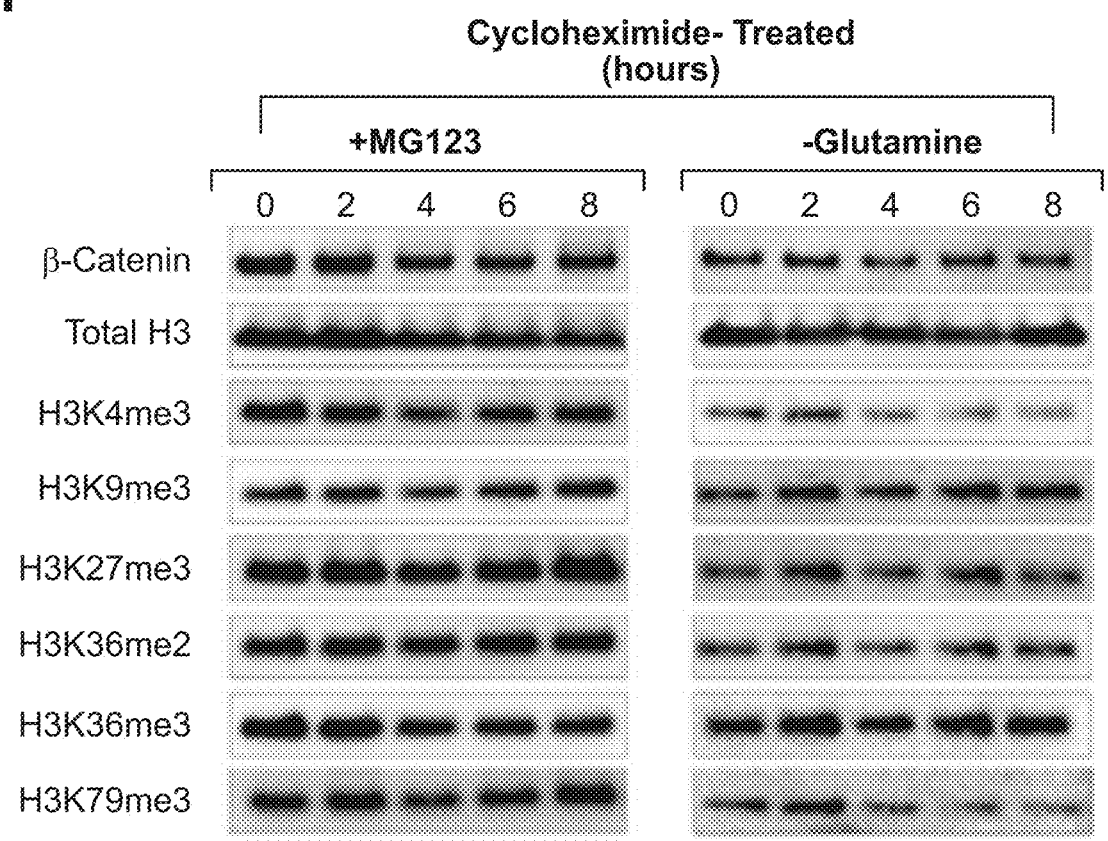
FIG. 5(h) shows a photographic representation of western blot analysis of TS after glutamine starvation or MG132 (10 μM) together with cycloheximide treatment. Cells were treated with 20 μg/ml cycloheximide and then harvested at indicated time points. β-catenin was used as loading control.

Following the treatment of cells with each of these inhibitors, the modes of action of these inhibitors were validated through LC/MS analyses (FIG. 5b). Inhibition by D9 led to an accumulation of intracellular SAH levels (~30 fold), resulting in the competitive inhibition of all SAM-dependent methylation reactions. FIDAS5, however, strongly reduced intracellular levels of SAM and SAH (~10 fold) in TS cells, and more potently inhibited methionine cycle activity (FIG. 5c). Exposure of TS cells transiently to D9 did not result in dramatic overall changes to histone methylation levels (FIG. 5d), but surprisingly, colony- and tumor-forming abilities were partially hampered (FIG. 5e). FIDAS5 treatment, interestingly, resulted in complete ablation of all histone methylation marks analyzed in TS cells (FIG. 5d). Associated colony- and tumor-forming capabilities were severely diminished (FIG. 5f). Consistent with the methionine starvation studies, the loss of CD166 expression in TS cells was observed upon FIDAS treatment (FIG. 11a). In contrast, NIH 3T3 and Adh cells, which were far less dependent on methionine, did not demonstrate reduction in histone methylation marks upon FIDAS5 treatment (FIG. 5d, middle and right). This was because there was no measurable turnover of histones and in particular, methylated histones, over 8 h in NIH 3T3 and Adh cells, as compared to a much higher turnover rate in TS cells (FIG. 5g). This high turnover of methylated histones in TS cells was rescued by the proteasomal inhibitor MG132, or the inhibition of a subset of histone demethylases by glutamine starvation, indicating that histone ubiquitination and demethylation are involved in the destabilization of methylated histones in TS ells (FIG. 5h).

Figure 11C:
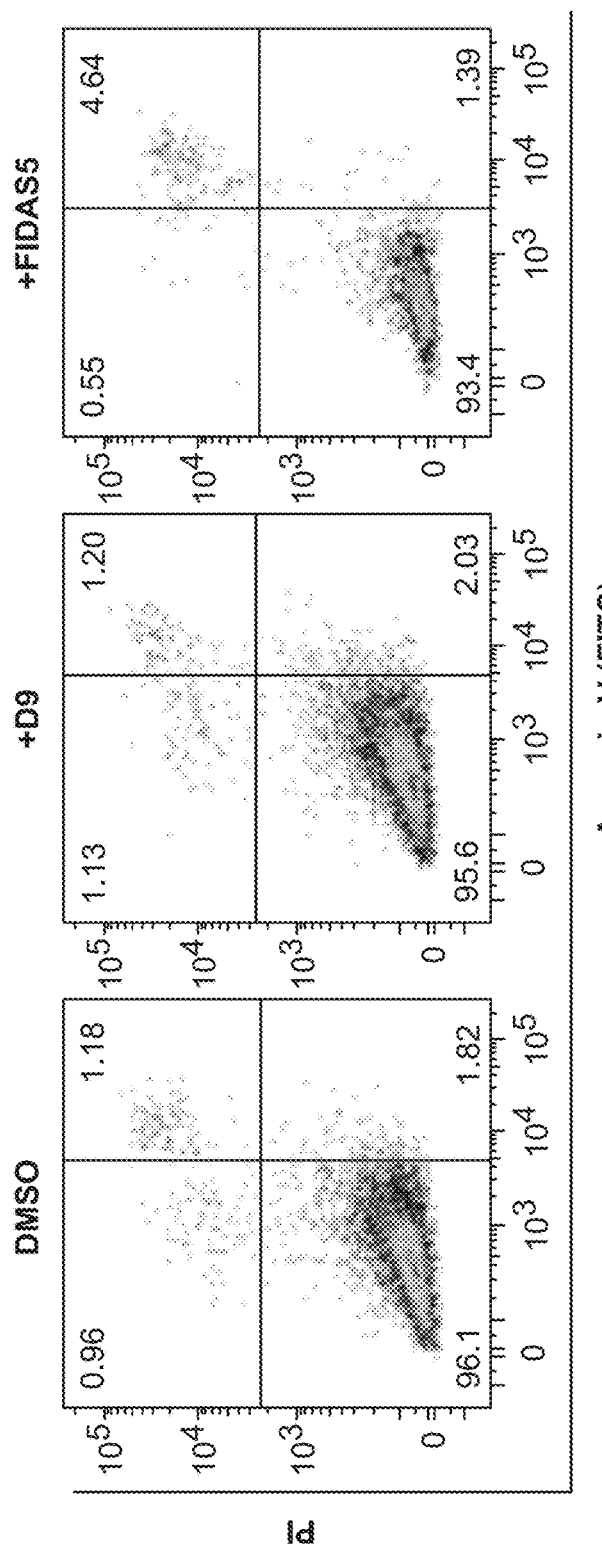
FIGS. 11(c) and (d) are graphical representations of apoptosis in inhibitor treated TS cells. (c) Inhibitor treated cells were stained with PI and Annexin V. Top: Representative plots of Annexin V and PI intensity. Bottom: Percentage of Annexin V positive cells is indicated in histograms. Error bars indicate s.d. n=4 for DMSO and D9 conditions; n=3 for FIDAS5 condition. (d) Percentage of Annexin-V positive cells is indicated in histograms. Error bars indicate s.d. n=4 for all conditions.
Figure 11C:
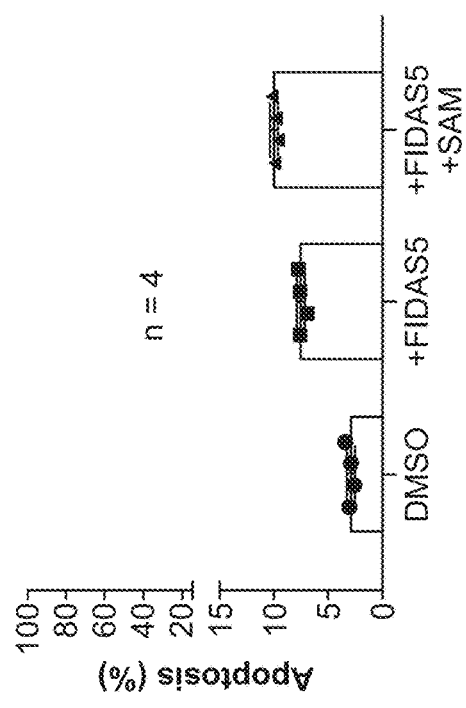
Figure 11F:
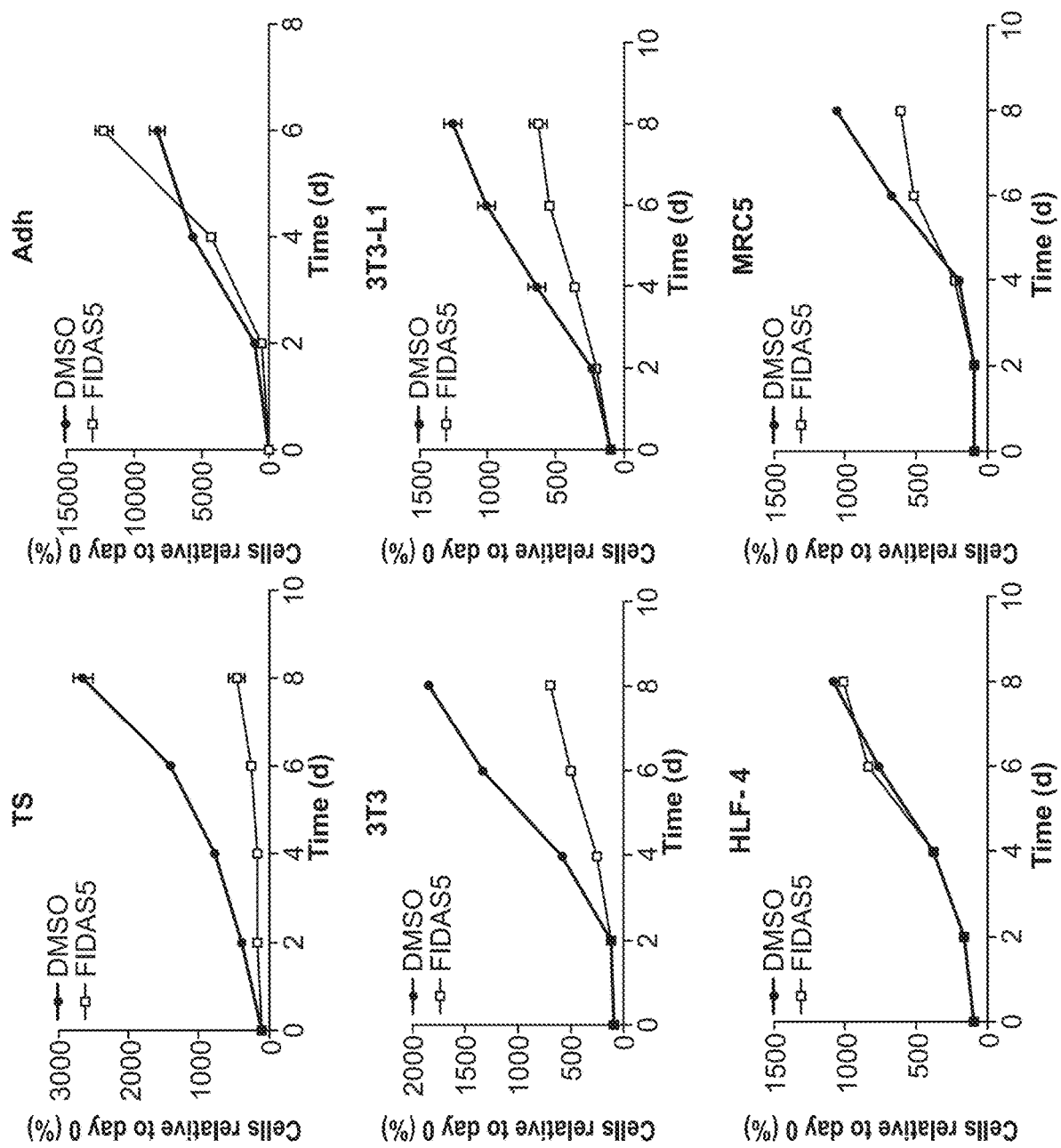
FIG. 11(f) is a graphical representation showing the proliferation of TS, Adh and untransformed cells grown in FIDAS5-containing media. Cell numbers normalized to starting numbers were assessed every two days using CellTiter-Glo. Error bars denote s.d.; n=10.

To exclude the possibility of general cytotoxicity by these inhibitors in TS cells, the transient exposure to D9 or FIDAS5, to a large extent, did not negatively impact their long-term proliferation ability or trigger apoptosis (FIG. 11b-d). Longer term exposure of TS cells to FIDAS5 for six days prior to returning them to medium without FIDAS5, however, completely ablated their growth capacity, as expected (FIG. 11e). Adh and non-neoplastic cell lines, however, were far less affected, thus highlighting the therapeutic potential of FIDAS5 or related molecules (FIG. 11f). Since FIDAS5 treatment reduced SAM necessary for methylation activity and TIC function, it was reasoned that the addition of exogenous SAM could bypass MAT2A inhibition. Supplementation of TS cells with 500 μM SAM in the presence FIDAS5 treatment rescued, to a large extent, histone methylation, as well as colony- and tumor-formation capabilities (FIG. 5d, f).

Figure 11G:
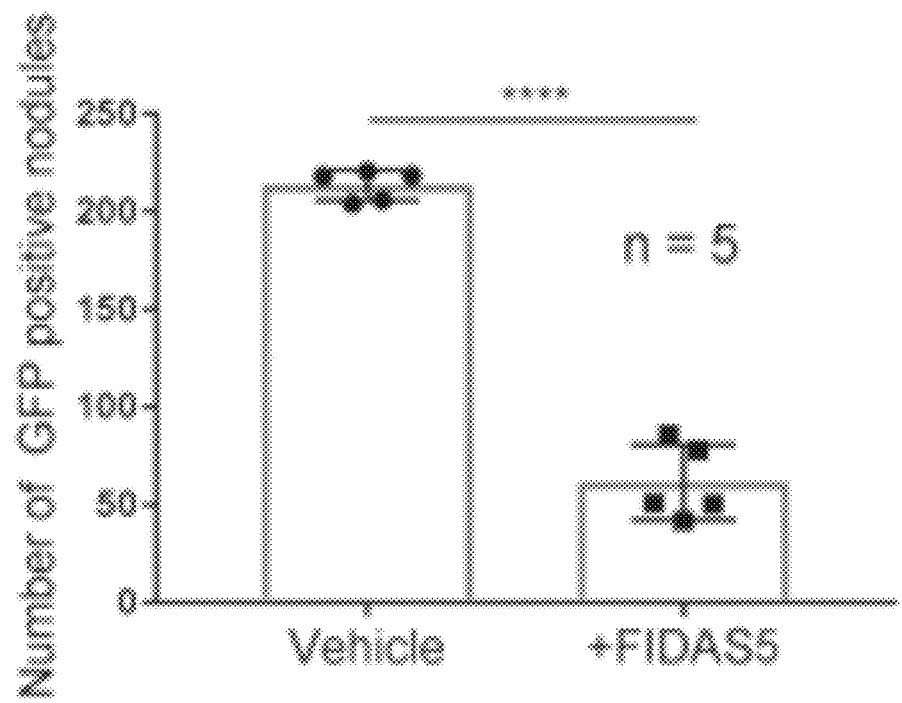
FIG. 11(g) is a graphical representation showing analyses of orthotopically implanted GFP-expressing TS cells in lungs of NSG mice 5 weeks post implantation. Histogram shows the number of GFP+ lesions in mice injected with TS cells grown and then treated with corn oil (vehicle) or FIDAS5 for 3 days. Error bars denote s.d., n=5 for all injections. **** denotes p=0.0001 by Student's t test.

Since FIDAS5 appeared to more specifically disrupt the methionine cycle and inhibit cellular methylation activities compared to D9, it was sought to test whether its systemic delivery could impact the tumorigenic potential of TS cells. These highly tumorigenic cells were first subcutaneously implanted into NSG mice and FIDAS5 (40 mg/kg) or corn oil carrier was immediately administered via intraperitoneal injection for three consecutive days. After 6 weeks, mice transiently treated with FIDAS5 produced tumors that were much smaller than carrier-treated controls. Similarly, a decreased number of pulmonary lesions were found in NSG mice that were orthotopically implanted with TS cells and transiently treated with FIDAS (FIG. 11g). To exclude the possibility of general cytotoxicity associated with the inhibitor on TS cells, TS cell-implanted NSG mice were treated with cisplatin (4 mg/kg), a frontline chemotherapeutic agent that broadly target bulk cancer cells in NSCLC tumors, in the same manner (FIG. 5i). Cisplatin, however, was unable to halt tumor growth, strongly underscoring the resistance of TICs to chemotherapy. To determine whether FIDAS5 treatment could disrupt the growth of patient-derived lung tumor xenografts, NSG mice bearing two different PDX lines were treated with FIDAS5 (40 mg/kg) for three days immediately after implantation (FIG. 5j). The xenograft tumors which formed after six weeks were at least 6-fold smaller in the FIDAS5-treated relative to sham-treated mice (FIG. 5j). The response of the lung PDX to FIDAS5 could, in part, be attributed to its strong expression of MAT2A (FIG. 10j). Taken together, transient treatment with methionine cycle inhibitors, but not chemotherapy, may be sufficient to impact the growth of tumors that is driven by TICs and highlights the need to explore the use of metabolic enzyme inhibitors as a part of cancer treatment.

Example 5

Here, it is demonstrated for the first time that more that just influencing proliferation, methionine consumption via a greatly increased flux into the methionine cycle is critical for driving tumorigenesis of TLCs in lung cancer. While both TICs and their differentiated counterparts depend on exogenous methionine for long term survival, short term starvation of methionine, but not other amino acids, leads to dramatic disruption of tumor initiating ability, largely attributable to a blockade in cellular methylation in TICs. In contrast to their previously characterized roles as oncometabolites in cancer cell proliferation, short-term starvation of glutamine or serine and glycine did not impact methionine cycle flux or tumor formation ability. This underscores the less-appreciated influence of methionine cycle flux programs that are associated with tumor initiation.

Prolonged methionine starvation in immunocompromised mice was previously found to reduce tumor load but it was eventually lethal. Here, it is demonstrated that transient methionine depletion could produce long-term disruption of TIC function and highlight methionine cycle inhibition as a TIC-targeting strategy. As a proof of principle, transient methionine starvation or small molecule inhibition with FIDAS5 could dramatically alter the tumorigenicity of TIC, while having little impact on differentiated cancer. This highlights the therapeutic potential of targeting TIC vulnerability through disruption of the methionine cycle. More broadly, it was also observed that MAT2A expression to be significantly higher in other cancers than their corresponding normal tissues (FIG. 11f). Among cancer cell lines representing a variety of cancers, they can be classified as having either high or low MAT2A expression (FIG. 11g). To test the functional consequence of MAT2A expression, it was found that those expressing high MAT2A to be dramatically hampered in their growth upon FIDAS5 treatment, whereas those that express low MAT2A were largely insensitive, thus implicating MAT2A and the methionine cycle in other cancers (FIG. 5h).

The metabolic basis of methionine dependency was previously unclear. Earlier studies attempting to address this were confounded by the relatively longer time frame (~48 hours) required for radioactive label-transfer experiments, in contrast to the exceedingly rapid rates of methionine consumption and regeneration in cells. Using a LC/MS-based isotopomer method that is highly sensitive for metabolite tracking and detection, it is shown that methionine dependency is a direct consequence of high methionine and SAM consumption rates and not due to a defect in homocysteine re-methylation. Because of the surprisingly high rates of methionine consumption unique to lung TICs, de novo synthesis from homocysteine cannot meet demands for sustaining SAM synthesis, thus creating an addiction to exogenous methionine. This addiction seems to be a result of unusually fast turnover of methylated histones that was only observed in TICs (FIG. 5g). This shows that there is a viable therapeutic window for transient targeting of TIICs in combination with standard-of-care chemotherapy. In agreement, MIAT2A knockdown seems only to affect the viability of TICs and not other differentiated or non-neoplastic lines despite comparable expression of MAT2A.

Figure 11H:
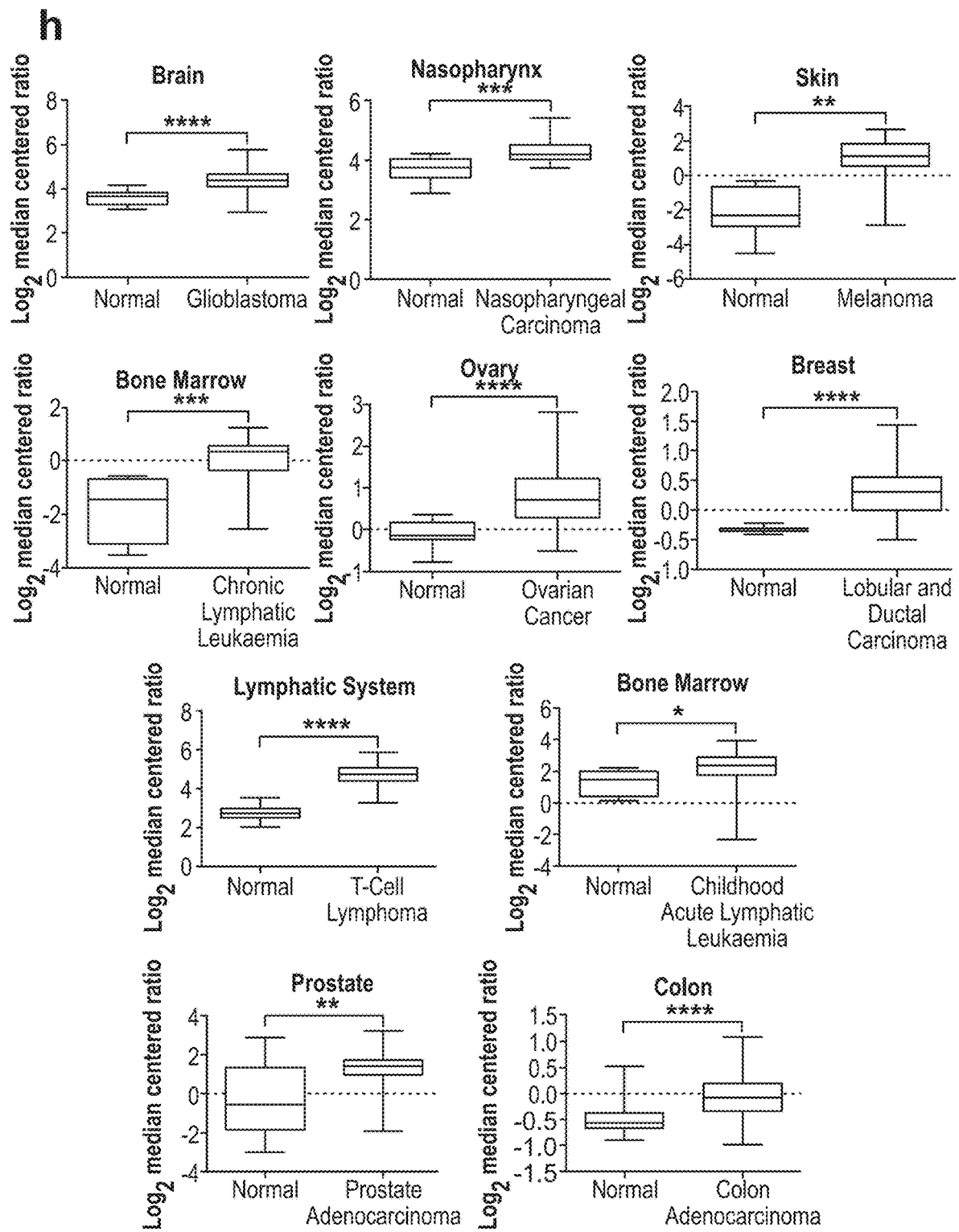
FIG. 11(h) is a graphical representation showing the comparison of MAT2A mRNA levels between normal and tumor tissue in other cancers. Data for glioblastoma (The Cancer Genome Atlas), colorectal cancer (The Cancer Genome Atlas), nasopharyngeal carcinoma, leukaemia, lymphoma, ovarian carcinoma, prostate adenocarcinoma and breast cancer was mined from the Oncomine (ThermoFisher) database. ** denotes $p<0.0001$, * denotes $p \leq S\ 0.0001$, ** denotes $p \leq S0.001$, and * denotes $p \leq 0.05$ using Student's unpaired two-tailed t-test.

Prolonged methionine starvation in immunocompromised mice could reduce tumor load but it was eventually lethal. Here, it was demonstrated that transient methionine depletion could produce long-term disruption of TIC function and highlight methionine cycle inhibition as a TIC-targeting strategy. As proof of principle, transient methionine starvation or small molecule inhibition with FIDAS5 could dramatically alter the tumorigenicity of TIC, while having little impact on differentiated cancer. This highlights the therapeutic potential of targeting TIC vulnerability through disruption of the methionine cycle. More broadly, it was also observed that MAT2A expression to be significantly higher in other cancers than their corresponding normal tissues (FIG. 11h). Furthermore, the elevated expression of MAT2A (but not MTHFR) in high grade lung tumors and metastases indicates the higher dependency on the methionine cycle activity and SAM production by these tumor cells, and could mark them for targeted therapies.

Figure 6A:
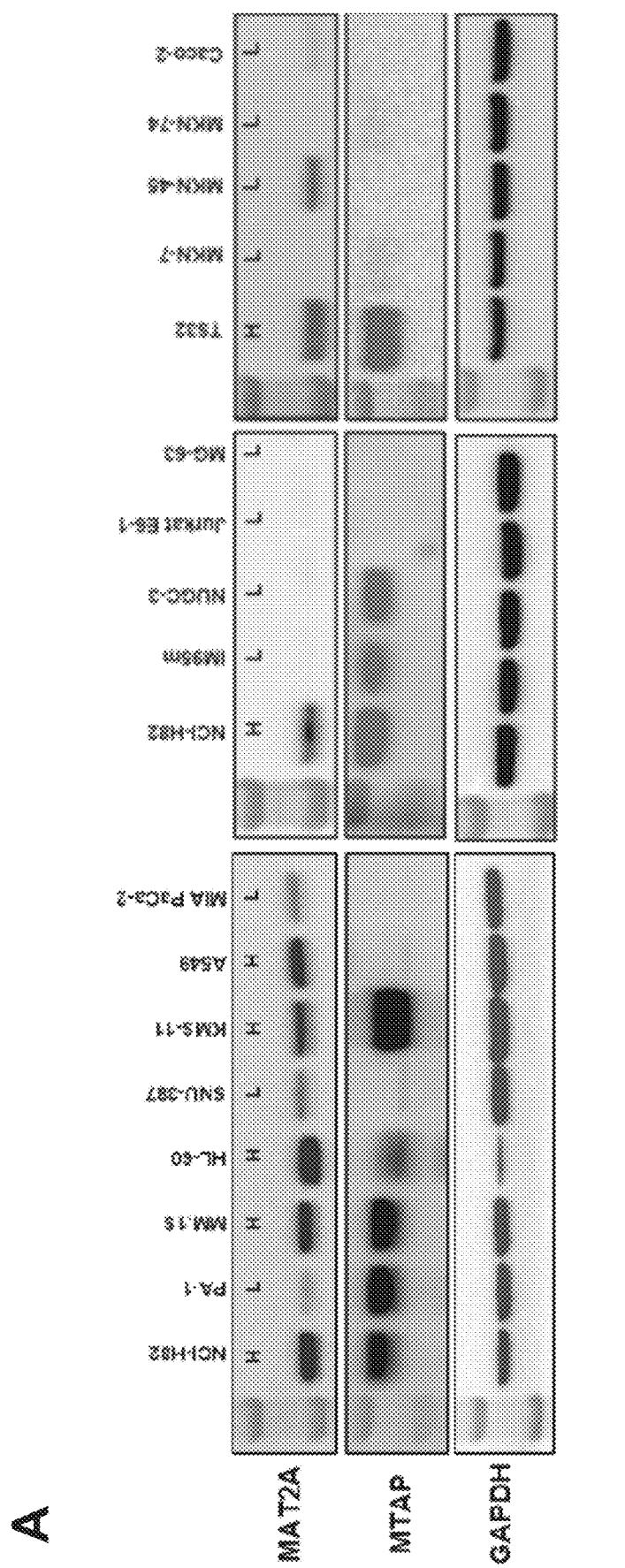
FIG. 6(a) shows a photographic representation of a western blot analysis of indicated cell lines for MAT2A levels and MTAP status. GAPDH is used as loading control.
Figure 11I:
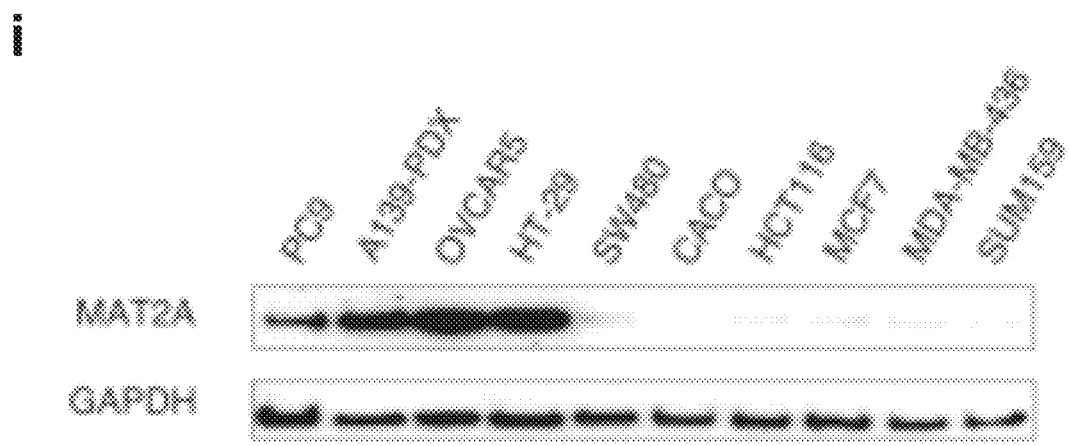
FIG. 11(i) is a photographical representation showing the western blot analysis of MAT2A in a panel of cancer cell lines. GAPDH was used as loading control.
Figure 11J:
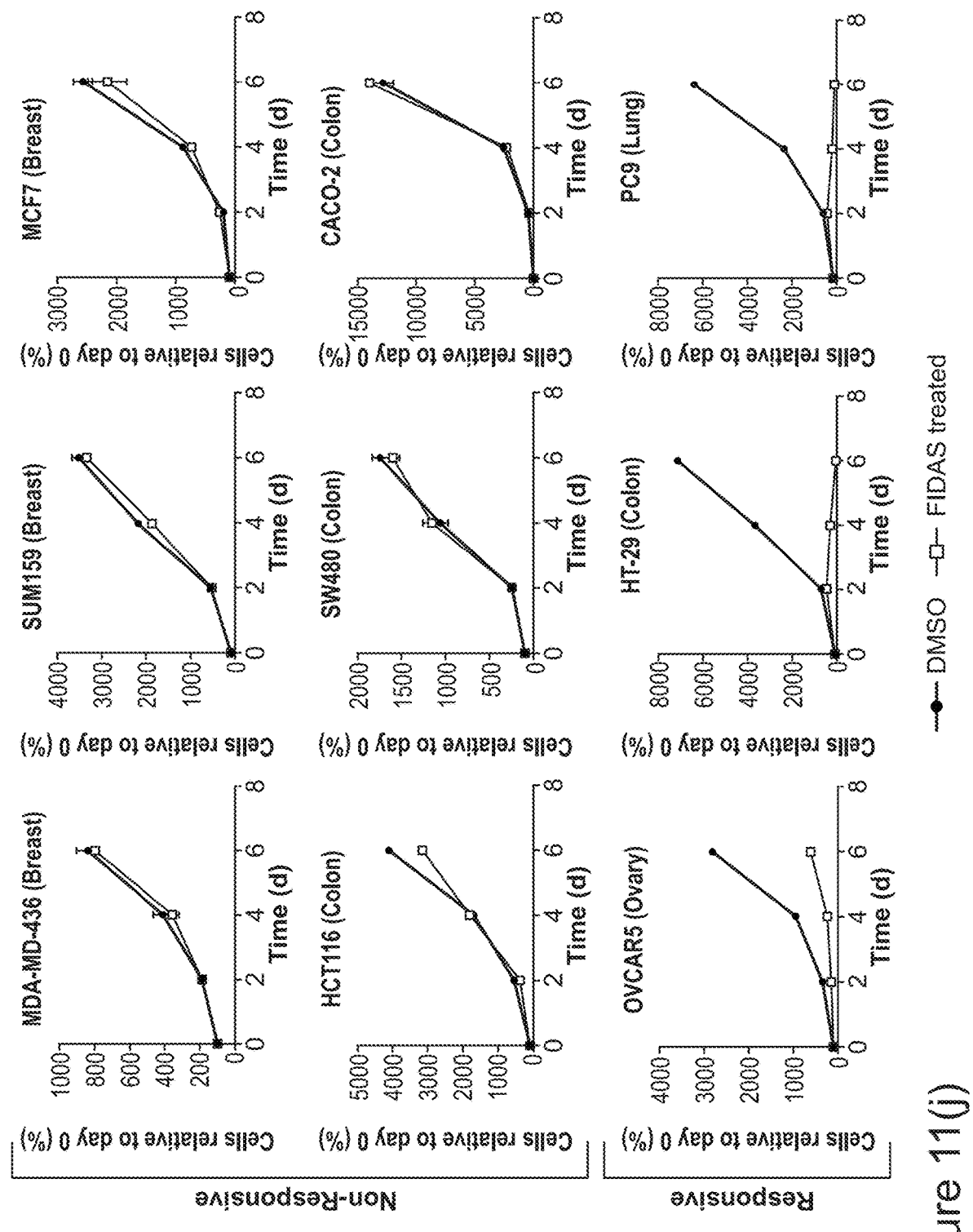
FIG. 11(j) is a graphical representation showing the proliferation of cancer cell lines grown in FIDAS5 containing medium (10 uM final concentration). Cell lines are grouped according to whether FIDAS5 inhibited (responsive) or did not inhibit (non-responsive) growth. Cell numbers normalized to starting conditions were assessed with CellTiter-Glo. Error bars denote s.d.; n=6.
Figure 11K:
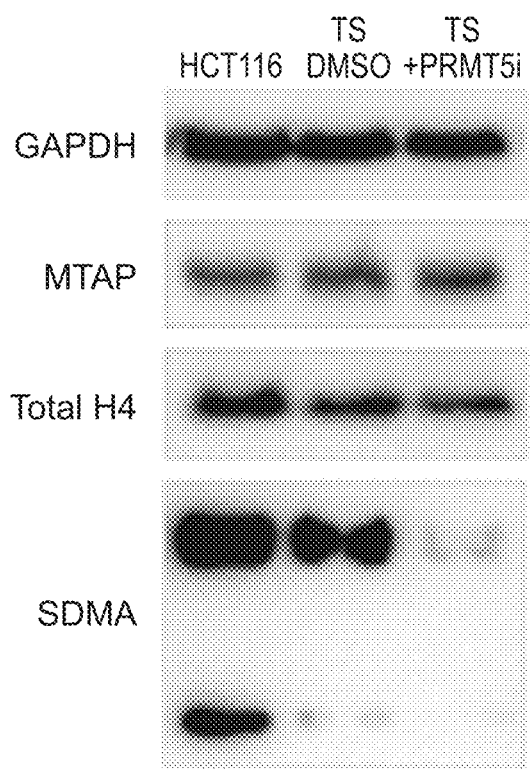
FIG. 11(k) is a photographic representation showing the western blot analyses of HCT116, TS and TS lines treated with the PRMT5 inhibitor EPZ015666.
Figure 12A:
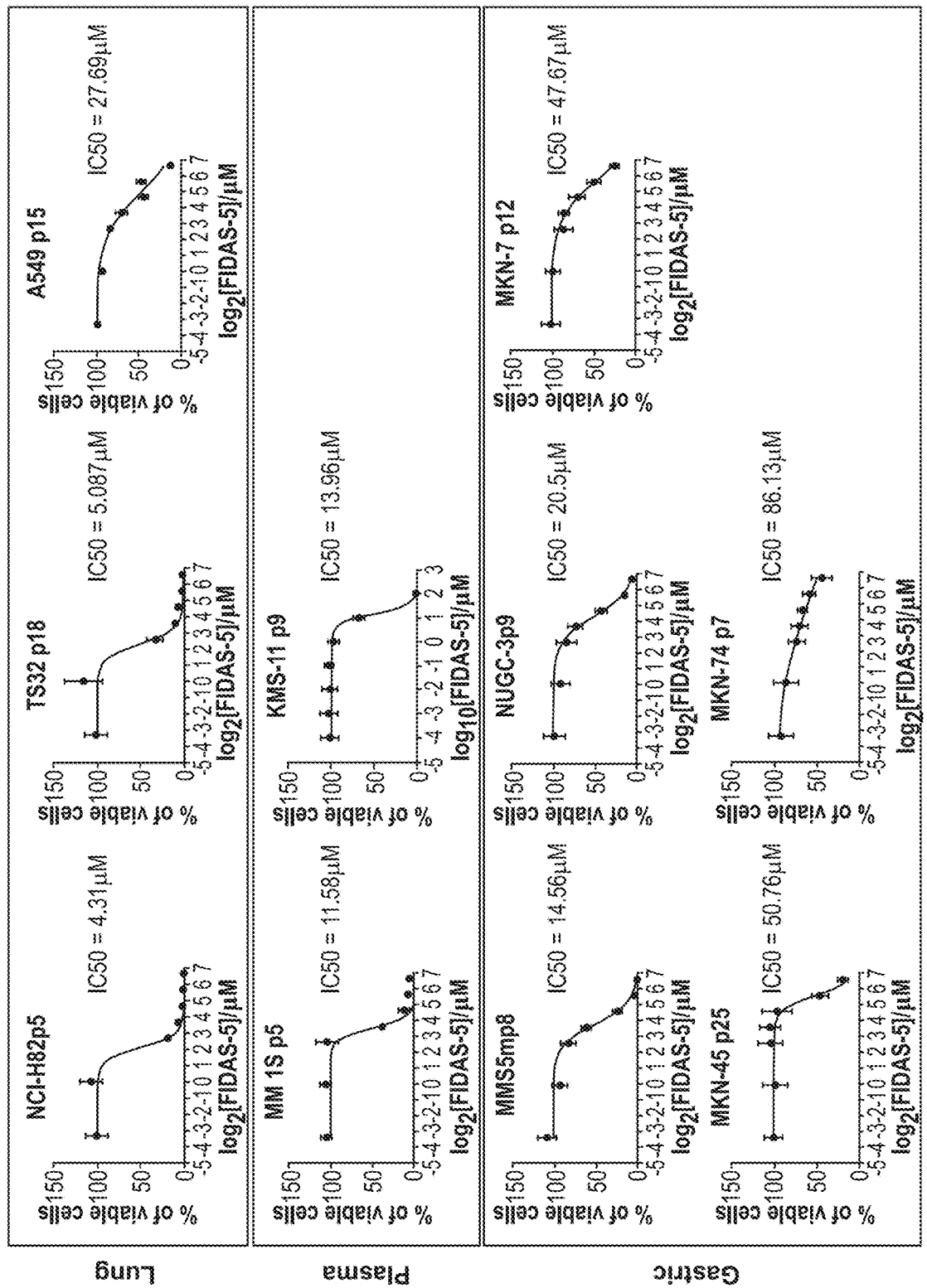
FIGS. 12(a)-12(c) are graphical representations showing the IC50 survival curves of indicated cell lines. Percentages of viable cells were determined 4 days post-incubation with indicated concentrations of FIDAS5. Cell lines were grouped by tissue of origin as indicated on the left.
Figure 12B:
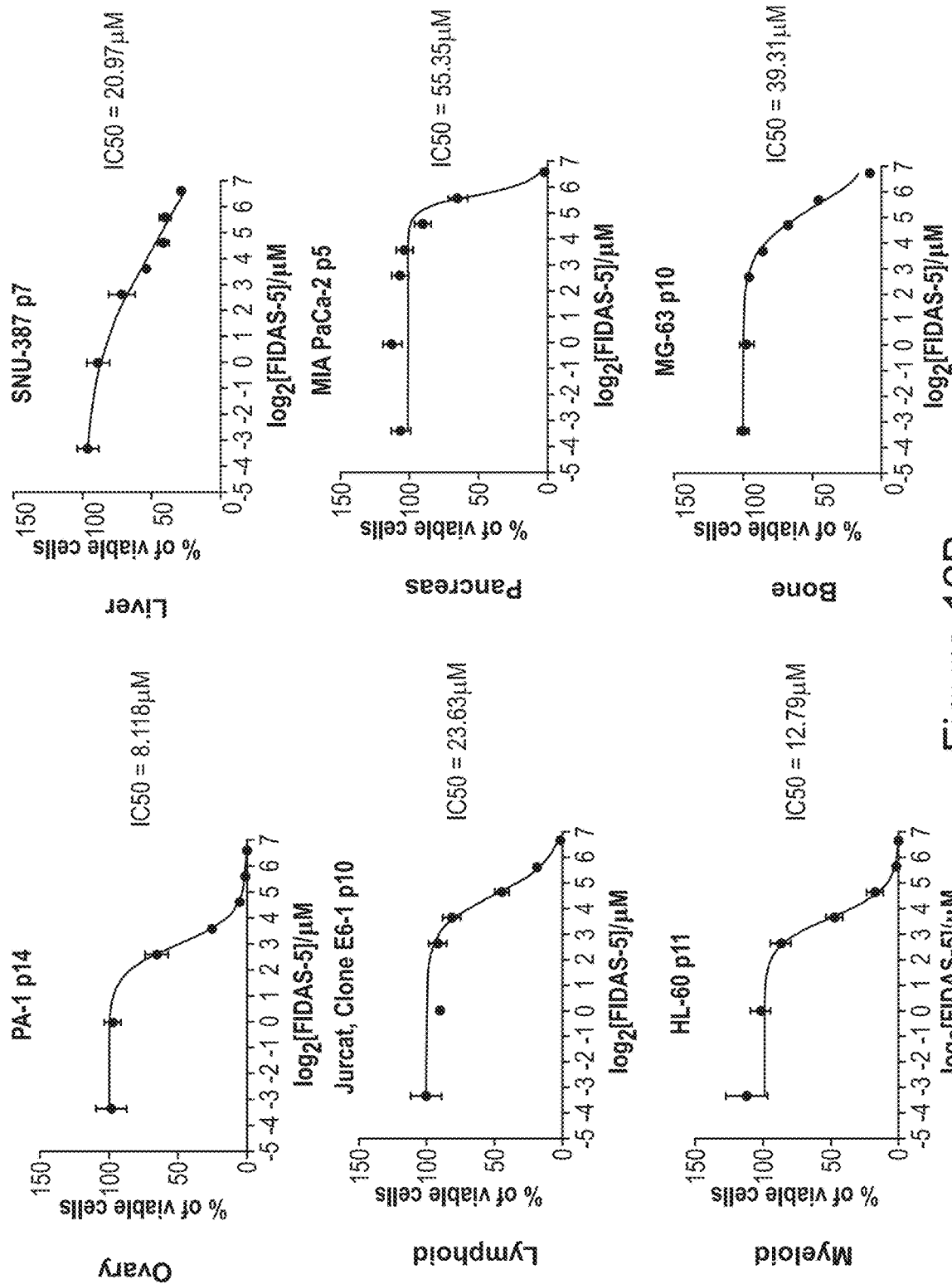
Figure 12C:
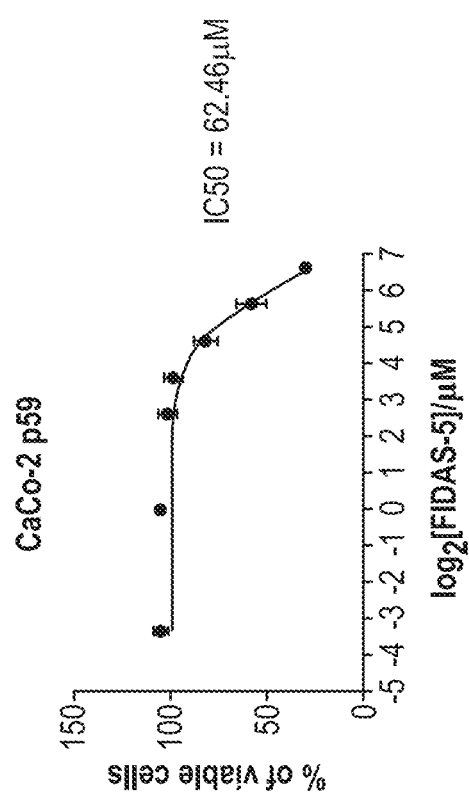

MAT2A expression has been shown to be tuned to SAM metabolite abundance, implying that MAT2A abundance could reflect SAM demand and extent of methionine dependency of a tumor mass. As proof of principle, a collection of cancer cell lines representing a variety of cancers with varying MAT2A expression (FIG. 11i) was examined. Indeed, it was found that those expressing high MAT2A to be dramatically hampered in their growth upon FIDAS5 treatment, whereas those that express low MAT2A were largely insensitive, thus implicating MAT2A and the methionine cycle in other cancers (FIG. 11j). Interestingly, it was recently shown targeting MAT2A flux in MTAP-null cancer lines could be a means to attenuate the oncogenic activity of PRMT5. It was noted that the TIC lines that were used expressed MTAP and have comparable levels of symmetric dimethylarginine, similar to the reference MTAP wildtype HCT116 cells used in that study (FIG. 11k). To further assess whether MAT2A expression and/or MTAP status affects sensitivity to FIDAS5 (i.e., MAT2A inhibition), a panel of cell lines, representing several cancer types, was stratified by MAT2A expression and MTAP status (FIG. 6a). Their corresponding IC50s values for FIDAS5 were generated. Furthermore, an IC50 cut off of less than 15 µM for susceptibility to FIDAS5 inhibition was also determined (FIG. 6b, FIG. 12a-12c). It was noted that the IC50 concentration for determining sensitivity versus resistance to MAT2A inhibitors may change, owing to the efficacy and nature of other compounds that may be synthesized to target MAT2A. It was found that susceptible cancer cell lines tended to have higher MAT2A and/or MTAP expression levels, and tumors bearing these features may be responsive to MAT2A inhibitors (FIG. 6c, d). Thus, the dependency on methionine as a therapeutic vulnerability does not appear to be dependent from the MTAP-MAT2A-PRMT5 axis.

Figure 14:
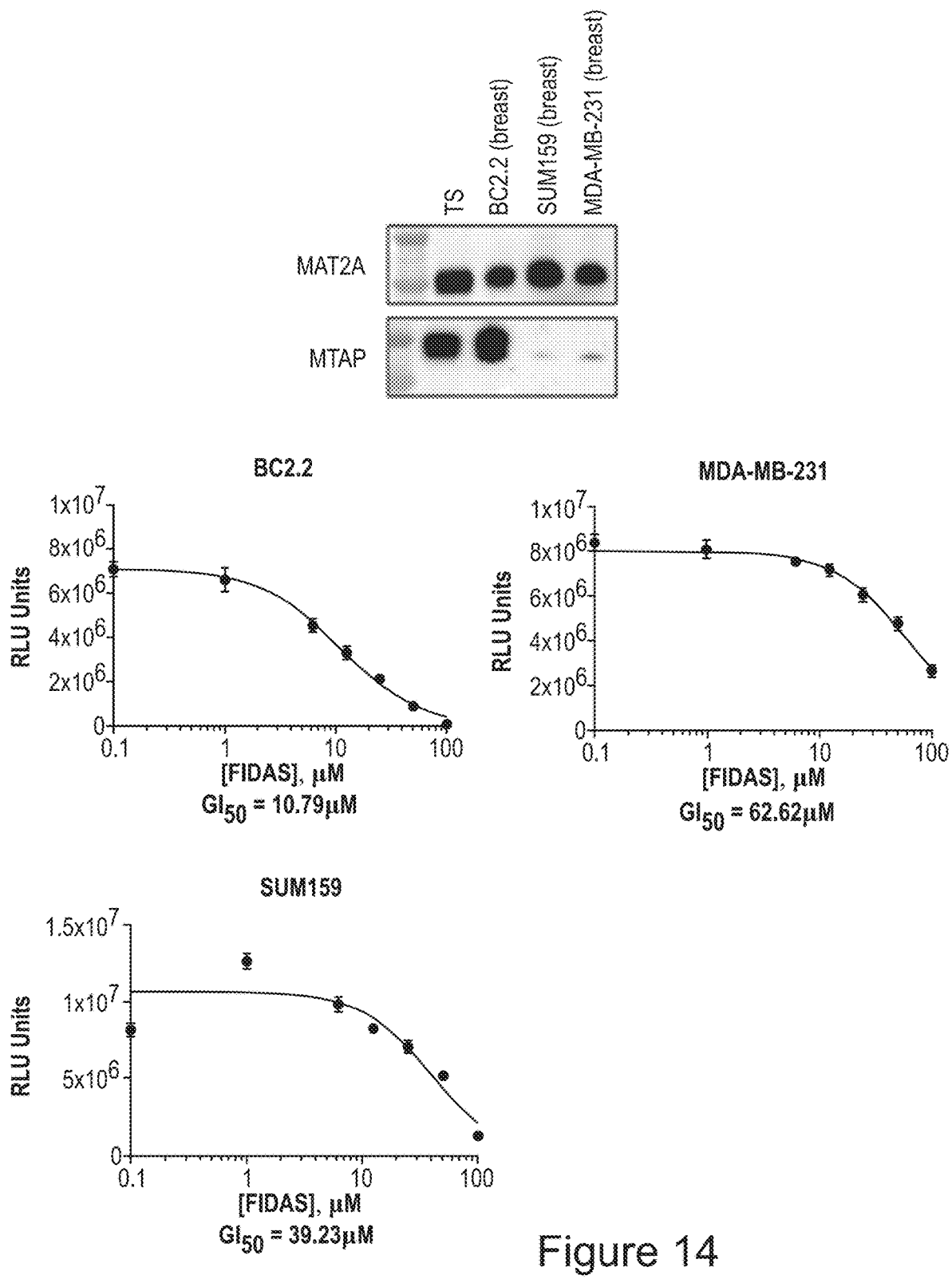
FIG. 14 is a photographic (top) and graphical representation (bottom) showing the inhibition of MAT2A as a useful therapeutic avenue in breast cancer. Triple-negative breast cancer (TNBC) cells, especially highly aggressive chemotherapy resistant cells (BC2.2), displayed sensitivity to MAT2A inhibition, as exemplified through the use of the MAT2A inhibitor, FIDAS5.

MAT2A inhibition, as exemplified through the use of the MAT2A inhibitor, FIDAS5, is shown to be effective against triple-negative breast cancer (TNBC) cells, in particular in highly aggressive chemotherapy resistant cells (BC2.2) (FIG. 14). This indicates the utility of MAT2A inhibitors or inhibition of the methionine cycle in TNBCs, including drug resistant tumors.

The metabolic basis of methionine dependency was previously unclear. Earlier studies attempting to address this were confounded by the relatively longer time frame (~48 hours) required for radioactive label-transfer experiments, in contrast to the exceedingly rapid rates of methionine consumption and regeneration in cells. Using a LC/MS-based isotopomer method that is highly sensitive for metabolite tracking and detection, methionine dependency is now shown to be a direct consequence of high methionine and SAM consumption rates and not due to a defect in homocysteine remethylation. Because of the surprisingly high rates of methionine consumption unique to lung TICs, de novo synthesis from homocysteine cannot meet demands for sustaining SAM synthesis, thus creating an addiction to exogenous methionine. This addiction seems to be a result of unusually fast turnover of methylated histones that was only observed in TICs (FIG. 5g). Potentially, this implies that there is a viable therapeutic window for transient targeting of TICs in combination with standard-of-care chemotherapy.

Notably, sustained MTHFR expression in GLDC KD cells could partially restore the tumorigenicity of GLDC KD cells, once again underlining the importance of MTHFR-driven flux in TICs and histone methylation. Indeed, MTHFR was previously demonstrated to play a key role in regulating the methionine cycle. In particular, somatic MTHFR hypomorphic mutations were also previously shown to decrease methionine cycle flux and transmethylation. However, the inability of MTHFR re-expression to fully restore the tumorigenicity of GLDC KD cells suggests that other branches of the one-carbon pathway might contribute to this phenotype. Of relevance, decreased one-carbon flux leading to a reduced capability to produce NAPDH units for maintaining redox balance might also contribute to the loss of tumorigenicity in GLDC KD cells, since oxidative stress can act as a barrier to tumor re-initiation.

Throughout the specification the aim has been to describe the embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

We claim:

1. A method of treating cancer or reducing the risk of recurrence of cancer in a subject; the method comprising the steps of:
   a) detecting increased expression levels of methionine adenosyltransferase 2A (MAT2A), methylthioadenosine phosphorylase (MTAP) and cluster of differentiation (CD166) biomarkers in a cancer specimen obtained from the subject,
   b) identifying the subject as one who is suitable for treatment with a methionine-cycle inhibitor when the expression levels of the biomarkers in the cancer specimen are increased as compared to the expression levels of the biomarkers in a non-cancerous specimen; and
   c) administering a methionine cycle inhibitor to the subject when the subject is identified as one who is suitable for treatment with the methionine-cycle inhibitor, so as to treat cancer or reduce the risk of recurrence of cancer in the subject,
   wherein the methionine-cycle inhibitor is a MAT2A inhibitor, D9, methotrexate or anti-folate.

2. The method of 1, wherein the subject is one who has previously had an anti-cancer therapy.

3. The method of 1, wherein the cancer is a methionine-dependent cancer.

4. A method of treating cancer or reducing the risk of recurrence of cancer in a subject; the method comprising the steps of:
   a) selecting a subject having increased expression levels of MAT2A, MTAP and CD166 biomarkers in a cancer specimen obtained from the subject,
   b) identifying the subject as one who is suitable for treatment with a methionine-cycle inhibitor when the expression levels of the biomarkers in the cancer specimen are increased as compared to the expression levels of the biomarkers in a non-cancerous specimen; and
   c) administering a methionine cycle inhibitor to the subject when the subject is identified as one who is suitable for treatment with the methionine-cycle inhibitor, so as to treat cancer or reduce the risk of recurrence of cancer in the subject,
wherein the methionine-cycle inhibitor is a MAT2A inhibitor, D9, methotrexate or anti-folate.

* * * * *

SEQUENCE LISTING

<160> NUMBER OF SEQ ID NOS: 11

<210> SEQ ID NO 1
<211> LENGTH: 58
<212> TYPE: DNA
<213> ORGANISM: Artificial Sequence
<220> FEATURE:
<223> OTHER INFORMATION: Control Luciferase shRNA

<400> SEQUENCE: 1
ccggcgctga gtacttcgaa atgtcctcga ggacatttcg aagtactcag cgttttttg    58

<210> SEQ ID NO 2
<211> LENGTH: 58
<212> TYPE: DNA
<213> ORGANISM: Artificial Sequence
<220> FEATURE:
<223> OTHER INFORMATION: SHMT2sh1

<400> SEQUENCE: 2
ccggccggag agttgtggac tttatctcga gataaagtcc acaactctcc ggtttttg     58

<210> SEQ ID NO 3
<211> LENGTH: 58
<212> TYPE: DNA
<213> ORGANISM: Artificial Sequence
<220> FEATURE:
<223> OTHER INFORMATION: SHMT2sh2

<400> SEQUENCE: 3
ccgggtctga cgtcaagcgg atatcctcga ggatatccgc ttgacgtcag acttttttg    58

<210> SEQ ID NO 4
<211> LENGTH: 58
<212> TYPE: DNA
<213> ORGANISM: Artificial Sequence
<220> FEATURE:
<223> OTHER INFORMATION: GLDCsh1

<400> SEQUENCE: 4
ccggcctgcc aacatccgtt tgaaactcga gtttcaaacg gatgttggca ggtttttg     58

<210> SEQ ID NO 5
<211> LENGTH: 58
<212> TYPE: DNA
<213> ORGANISM: Artificial Sequence
<220> FEATURE:
<223> OTHER INFORMATION: GLDCsh2

<400> SEQUENCE: 5
ccggccacgg aaactgcgat attaactcga gttaatatcg cagtttccgt ggtttttg     58

<210> SEQ ID NO 6
<211> LENGTH: 58
<212> TYPE: DNA
<213> ORGANISM: Artificial Sequence
<220> FEATURE:
<223> OTHER INFORMATION: MAT2Ash1

<400> SEQUENCE: 6
ccggagcagt tgtgcctgcg aaatactcga gtatttcgca ggcacaactg ctttttg      58

<210> SEQ ID NO 7
<211> LENGTH: 58
<212> TYPE: DNA
<213> ORGANISM: Artificial Sequence

```
<220> FEATURE:
<223> OTHER INFORMATION: MAT2Ash2

<400> SEQUENCE: 7
ccggccagat aagatttgtg accaactcga gttggtcaca aatcttatct ggtttttg        58

<210> SEQ ID NO 8
<211> LENGTH: 58
<212> TYPE: DNA
<213> ORGANISM: Artificial Sequence
<220> FEATURE:
<223> OTHER INFORMATION: MTHFRsh1

<400> SEQUENCE: 8
ccggatatta gacaggacca ttatgctcga gcataatggt cctgtctaat attttttg        58

<210> SEQ ID NO 9
<211> LENGTH: 57
<212> TYPE: DNA
<213> ORGANISM: Artificial Sequence
<220> FEATURE:
<223> OTHER INFORMATION: MTHFRsh2

<400> SEQUENCE: 9
ccggagagta tccaagacga cattcctcga ggaatgtcgt cttggatact ctttttt        57

<210> SEQ ID NO 10
<211> LENGTH: 58
<212> TYPE: DNA
<213> ORGANISM: Artificial Sequence
<220> FEATURE:
<223> OTHER INFORMATION: mat2ash1

<400> SEQUENCE: 10
ccggtttgga ggacgtacgt aataactcga gttattacgt acgtcctcca aatttttg        58

<210> SEQ ID NO 11
<211> LENGTH: 58
<212> TYPE: DNA
<213> ORGANISM: Artificial Sequence
<220> FEATURE:
<223> OTHER INFORMATION: mat2ash2

<400> SEQUENCE: 11
ccggaccgga atgaggaaga tattgctcga gcaatatctt cctcattccg gtttttg        58
```